United States Patent
Li et al.

(10) Patent No.: US 7,579,360 B2
(45) Date of Patent: Aug. 25, 2009

(54) TRIAZOLOPYRIDINE 11-BETA HYDROXYSTEROID DEHYDROGENASE TYPE I INHIBITORS

(75) Inventors: James J. Li, Pennington, NJ (US); Lawrence G. Hamann, North Grafton, MA (US); Haixia Wang, Princeton, NJ (US); Zheming Ruan, Dayton, NJ (US); Christopher B. Cooper, Lawrenceville, NJ (US); Jun Li, Princeton, NJ (US); Jeffrey A. Robl, Newtown, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 162 days.

(21) Appl. No.: 11/448,947

(22) Filed: Jun. 7, 2006

(65) Prior Publication Data
US 2006/0287357 A1    Dec. 21, 2006

Related U.S. Application Data

(60) Provisional application No. 60/688,993, filed on Jun. 9, 2005.

(51) Int. Cl.
*A01N 43/42* (2006.01)
*A61K 31/44* (2006.01)
*C07D 513/02* (2006.01)
*C07D 515/02* (2006.01)

(52) U.S. Cl. ........................ 514/303; 546/119
(58) Field of Classification Search .................. 546/119; 514/303
See application file for complete search history.

(56) References Cited

U.S. PATENT DOCUMENTS

| | | | |
|---|---|---|---|
| 3,597,423 | A | 8/1971 | Wiedemann et al. |
| 4,358,453 | A | 11/1982 | Bristol et al. |
| 5,236,917 | A | 8/1993 | Dunlap et al. |
| 6,696,464 | B2 | 2/2004 | McClure et al. |
| 6,730,690 | B2 | 5/2004 | Olson et al. |
| 7,144,907 | B2 | 12/2006 | Wallace et al. |
| 7,230,099 | B2 | 6/2007 | Wallace et al. |
| 2004/0053959 | A1 | 3/2004 | Buzon, Sr. et al. |
| 2004/0133011 | A1 | 7/2004 | Waddell et al. |
| 2004/0147568 | A1* | 7/2004 | Yu et al. .................... 514/357 |
| 2005/0049276 | A1 | 3/2005 | Kaufman et al. |
| 2005/0049419 | A1 | 3/2005 | Wallace et al. |
| 2005/0054701 | A1 | 3/2005 | Wallace et al. |
| 2005/0075365 | A1 | 4/2005 | Braganza et al. |
| 2005/0113283 | A1 | 5/2005 | Solow-Cordero et al. |
| 2005/0229333 | A1 | 10/2005 | Glenn, Jr. et al. |
| 2006/0030610 | A1 | 2/2006 | Koch et al. |
| 2006/0035922 | A1 | 2/2006 | Mathias et al. |
| 2006/0247245 | A1 | 11/2006 | Xu |

FOREIGN PATENT DOCUMENTS

| | | |
|---|---|---|
| EP | 0430385 | 6/1991 |
| JP | 47047396 | 11/1972 |
| JP | 200319277 | 11/2000 |
| WO | WO 97/47601 | 12/1997 |
| WO | WO 00/66572 | 11/2000 |
| WO | WO 03/065983 | 8/2003 |
| WO | WO 03/104207 | 12/2003 |
| WO | WO 03/104208 | 12/2003 |
| WO | WO 2004/056744 | 7/2004 |
| WO | WO 2004/058730 | 7/2004 |
| WO | WO 2004/058741 | 7/2004 |
| WO | WO 2004/065351 | 8/2004 |
| WO | WO 2004/089380 | 10/2004 |
| WO | WO 2004/106294 | 12/2004 |
| WO | WO 2005/046685 | 5/2005 |
| WO | WO 2005/047250 | 5/2005 |
| WO | WO 2005/073200 | 8/2005 |
| WO | WO 2005/097052 | 10/2005 |
| WO | WO 2006/015737 | 2/2006 |
| WO | WO 2006/018727 | 2/2006 |
| WO | WO 2006/018735 | 2/2006 |
| WO | WO 2006/026754 | 3/2006 |
| WO | WO 2006/030805 | 3/2006 |
| WO | WO 2006/034804 | 4/2006 |
| WO | WO 2006/036816 | 4/2006 |
| WO | WO 2006/036932 | 4/2006 |
| WO | WO 2006/038116 | 4/2006 |
| WO | WO 2006/038738 | 4/2006 |
| WO | WO 2006/040039 | 4/2006 |
| WO | WO 2006/042599 | 4/2006 |
| WO | WO 2006/044687 | 4/2006 |
| WO | WO 2006/044821 | 4/2006 |

(Continued)

OTHER PUBLICATIONS

Low et al., Journal of Neuroendocrinology (1994), 6(3), pp. 285-90.*

*Primary Examiner*—D. Margaret Seaman
*Assistant Examiner*—Niloofar Rahmani
(74) *Attorney, Agent, or Firm*—Terence J. Bogie

(57) ABSTRACT

Novel compounds are provided which are 11-beta-hydroxysteroid dehydrogenase type I inhibitors. 11-beta-hydroxysteroid dehydrogenase type I inhibitors are useful in treating, preventing, or slowing the progression of diseases requiring 11-beta-hydroxysteroid dehydrogenase type I inhibitor therapy. These novel compounds have the structure:

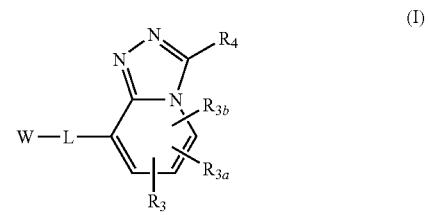

(I)

or stereoisomers or prodrugs or pharmaceutically acceptable salts thereof, wherein W, L, $R_3$, $R_{3a}$, $R_{3b}$ and $R_4$ are defined herein.

49 Claims, No Drawings

FOREIGN PATENT DOCUMENTS

| | | |
|---|---|---|
| WO | WO 2006/044958 | 4/2006 |
| WO | WO 2006/047317 | 5/2006 |
| WO | WO 2006/047631 | 5/2006 |
| WO | WO 2006/048330 | 5/2006 |
| WO | WO 2006/048331 | 5/2006 |
| WO | WO 2006/049952 | 5/2006 |
| WO | WO 2006/058752 | 6/2006 |
| WO | WO 2006/080533 | 8/2006 |
| WO | WO 2007/007688 | 1/2007 |
| WO | WO 2007/113226 | 10/2007 |

* cited by examiner

TRIAZOLOPYRIDINE 11-BETA HYDROXYSTEROID DEHYDROGENASE TYPE I INHIBITORS

This application claims the benefit of U.S. Provisional Application No. 60/688,993, filed Jun. 9, 2005, incorporated herein by reference in its entirety.

BACKGROUND OF THE INVENTION

The steroid hormone cortisol is a key regulator of many physiological processes. However, an excess of cortisol, as occurs in Cushing's Disease, provokes severe metabolic abnormalities including: type 2 diabetes, cardiovascular disease, obesity, and osteoporosis. Many patients with these diseases, however, do not show significant increases in plasma cortisol levels. In addition to plasma cortisol, individual tissues can regulate their glucocorticoid tone via the in situ conversion of inactive cortisone to the active hormone cortisol. Indeed, the normally high plasma concentration of cortisone provides a ready supply of precursor for conversion to cortisol via the intracellular enzyme 11-beta-hydroxysteroid dehydrogenase type I (11beta-HSD1).

11beta-HSD1 is a member of the short chain dehydrogenase superfamily of enzymes. By catalyzing the conversion of cortisone to cortisol, 11beta-HSD1 controls the intracellular glucocorticoid tone according to its expression and activity levels. In this manner, 11beta-HSD1 can determine the overall metabolic status of the organ. 11beta-HSD1 is expressed at high levels in the liver and at lower levels in many metabolically active tissues including the adipose, the CNS, the pancreas, and the pituitary. Taking the example of the liver, it is predicted that high levels of 11beta-HSD1 activity will stimulate gluconeogenesis and overall glucose output. Conversely, reduction of 11beta-HSD1 activity will downregulate gluconeogenesis resulting in lower plasma glucose levels.

Various studies have been conducted that support this hypothesis. For example, transgenic mice expressing 2× the normal level of 11beta-HSD1 in only the adipose tissue show abdominal obesity, hyperglycemia, and insulin resistance. (H. Masuzaki, J. Paterson, H. Shinyama, N. M. Morton, J. J. Mullins, J. R. Seckl, J. S. Flier, A Transgenic Model of Visceral Obesity and the Metabolic Syndrome, *Science* 294: 2166-2170 (2001). Conversely, when the 11beta-HSD1 gene is ablated by homologous recombination, the resulting mice are resistant to diet induced obesity and the accompanying dysregulation of glucose metabolism (N. M. Morton, J. M. Paterson, H. Masuzaki, M. C. Holmes, B. Staels, C. Fievet, B. R. Walker, J. S. Flier, J. J. Mullings, J. R. Seckl, Novel Adipose Tissue-Mediated Resistance to Diet-induced Visceral Obesity in 11β-Hydroxysteroid Dehydrogenase Type 1-Deficient Mice. *Diabetes* 53: 931-938 (2004). In addition, treatment of genetic mouse models of obesity and diabetes (ob/ob, db/db and KKAy mice) with a specific inhibitor of 11beta-HSD1 causes a decrease in glucose output from the liver and an overall increase in insulin sensitivity (P. Alberts, C. Nilsson, G. Selen, L. O. M. Engblom, N. H. M. Edling, S. Norling, G. Klingstrom, C. Larsson, M. Forsgren, M. Ashkzari, C. E. Nilsson, M. Fiedler, E. Bergqvist, B. Ohman, E. Bjorkstrand, L. B. Abrahmsen, Selective Inhibition of 11β-Hydroxysteroid Dehydrogenase Type I Improves Hepatic Insuling Sensuitivity in Hyperglycemic Mice Strains, *Endocrinology* 144: 4755-4762 (2003)). Furthermore, inhibitors of 11beta-HSD1 have been shown to be effective in treating metabolic syndrome and atherosclerosis in high fat fed mice (Hermanowoki-Vosetka et. al., *J. Eg. Med.*, 2002, 202(4), 517-527). Based in part on these studies, it is believed that local control of cortisol levels is important in metabolic diseases in these model systems. In addition, the results of these studies also suggest that inhibition of 11beta-HSD1 will be a viable strategy for treating metabolic diseases such as type 2 diabetes, obesity, and the metabolic syndrome.

Lending further support to this idea are the results of a series of preliminary clinical studies. For example, several reports have shown that adipose tissue from obese individuals has elevated levels of 11beta-HSD1 activity. In addition, studies with carbenoxolone, a natural product derived from licorice that inhibits both 11beta-HSD1 and 11beta-HSD2 (converts cortisol to cortisone in kidney) have shown promising results. A seven day, double blind, placebo controlled, cross over study with carbenoxolone in mildly overweight individuals with type 2 diabetes showed that patients treated with the inhibitor, but not the placebo group, displayed a decrease in hepatic glucose production (R. C. Andrews, O. Rooyackers, B. R. Walker, *J. Clin. Endocrinol. Metab.* 88: 285-291 (2003)). This observation is consistent with the inhibition of 11beta-HSD1 in the liver. The results of these preclinical and early clinical studies strongly support the concept that treatment with a potent and selective inhibitor of 11beta-HSD1 will be an efficacious therapy in patients afflicted with type 2 diabetes, obesity, and the metabolic syndrome.

SUMMARY OF THE INVENTION

In accordance with the present invention, aryl and heteroaryl and related compounds are provided that have the general structure of formula I:

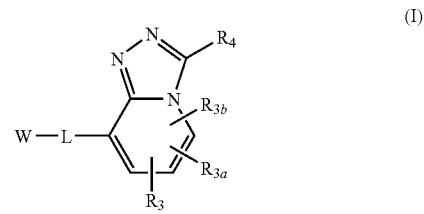

(I)

wherein W, L, $R_3$, $R_{3a}$, $R_{3b}$ and $R_4$ are defined below.

The compounds of the present invention inhibit the activity of the enzyme 11-beta-hydroxysteroid dehydrogenase type I. Consequently, the compounds of the present invention may be used in the treatment of multiple diseases or disorders associated with 11-beta-hydroxysteroid dehydrogenase type I, such as diabetes and related conditions, microvascular complications associated with diabetes, the macrovascular complications associated with diabetes, cardiovascular diseases, Metabolic Syndrome and its component conditions, inflammatory diseases and other maladies. Examples of diseases or disorders associated with the activity of the enzyme 11-beta-hydroxysteroid dehydrogenase type I that can be prevented, inhibited, or treated according to the present invention include, but are not limited to, diabetes, hyperglycemia, impaired glucose tolerance, insulin resistance, hyperinsulinemia, retinopathy, neuropathy, nephropathy, delayed wound healing, atherosclerosis and its sequelae (acute coronary syndrome, myocardial infarction, angina pectoris, peripheral vascular disease, intermittent claudication), abnormal heart function, myocardial ischemia, stroke, Metabolic Syndrome, hypertension, obesity, dyslipidemia, hyperlipidemia, hypertriglyceridemia, hypercholesterolemia, low HDL, high LDL, non-cardiac ischemia, infection, cancer, vascular restenosis, pancreatitis, neurodegenerative disease, lipid disorders, cognitive impairment and dementia, bone disease, HIV protease associated lipodystrophy, glaucoma and inflammatory diseases, such as, rheumatoid arthritis and osteoarthritis.

Inhibitors of 11beta-HSD1 are also described in U.S. patent application Ser. No. 11/448,946 titled "Heteroaryl 11-Beta Hydroxysteroid Dehydrogenase Type I Inhibitors", having the same assignee as the present invention and filed concomitantly herewith.

The present invention provides for compounds of formula I, pharmaceutical compositions employing such compounds, and for methods of using such compounds. In particular, the present invention provides a pharmaceutical composition comprising a therapeutically effective amount of a compound of formula I, alone or in combination with a pharmaceutically acceptable carrier.

Further, in accordance with the present invention, a method is provided for preventing, inhibiting, or treating the progression or onset of diseases or disorders associated with the activity of the enzyme 11-beta-hydroxysteroid dehydrogenase type I, such as defined above and hereinafter, wherein a therapeutically effective amount of a compound of formula I is administered to a mammalian, i.e., human, patient in need of treatment.

The compounds of the invention can be used alone, in combination with other compounds of the present invention, or in combination with one or more other agent(s).

Further, the present invention provides a method for preventing, inhibiting, or treating the diseases as defined above and hereinafter, wherein a therapeutically effective amount of a combination of a compound of formula I and another compound of formula I and/or at least one other type of therapeutic agent, is administered to a mammalian, i.e., human, patient in need of treatment.

DESCRIPTION OF THE INVENTION

In accordance with the present invention, compounds of formula I are provided

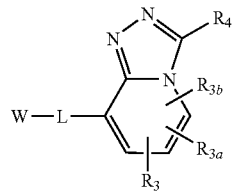

(I)

enantiomers, diastereomers, solvates, salts or prodrugs thereof wherein:

W is aryl, cycloalkyl, heteroaryl or heterocyclyl, all of which may be optionally substituted with $R_1$, $R_{1a}$, $R_{1b}$, $R_{1c}$, and $R_{1d}$;

$R_1$, $R_{1a}$, $R_{1b}$, $R_{1c}$ and $R_{1d}$ are independently hydrogen, halogen, —OH, —CN, —NO$_2$, —CO$_2$R$_{2a}$, —CONR$_2$R$_{2a}$, —SO$_2$NR$_2$R$_{2a}$, —SOR$_{2a}$, SO$_2$R$_{2a}$, —NR$_2$SO$_2$R$_6$, —NR$_2$CO$_2$R$_6$, alkyl, haloalkyl, cycloalkyl, alkoxy, aryloxy, alkenyl, haloalkoxy, alkylthio, arylthio, arylsulfonyl, alkylamino, aminoalkyl, arylamino, heteroarylamino, aryl, heteroaryl or heterocyclyl, wherein the aryl, heteroaryl or heterocyclyl may be optionally substituted with $R_7$, $R_{7a}$, $R_{7b}$, and $R_{7c}$;

or alternatively any two $R_1$, $R_{1a}$, $R_{1b}$, $R_{1c}$ and $R_{1d}$ can be taken together to form a fused aryl, heteroaryl, heterocyclyl ring or spiro heterocyclyl ring;

L is a bond, O, S, SO, SO$_2$, alkenyl, cycloalkyl, NR$_5$, CR$_2$R$_{2a}$, CR$_2$R$_{2a}$CR$_{2b}$R$_{2c}$, SO$_2$NR$_2$, OCR$_2$R$_{2a}$, OCR$_2$R$_{2a}$CR$_{2b}$R$_{2c}$, CR$_2$R$_{2a}$O, CR$_{2b}$R$_{2c}$, CR$_2$R$_{2a}$O, N(R$_5$) CR$_2$R$_{2a}$, CR$_2$R$_{2a}$N(R$_5$), SCR$_2$R$_{2a}$, CR$_2$R$_{2a}$S, CR$_2$R$_{2a}$SO, CR$_2$R$_{2a}$SO$_2$, SOCR$_2$R$_{2a}$, SO$_2$CR$_2$R$_{2a}$, CR$_2$R$_{2a}$OCR$_{2b}$R$_{2c}$, CR$_2$R$_{2a}$SCR$_{2b}$R$_{2c}$, CR$_2$R$_{2a}$SO$_2$CR$_{2b}$R$_{2c}$, SO$_2$NR$_{2c}$R$_{2a}$R$_{2b}$, COCR$_2$R$_{2a}$, CR$_2$R$_{2a}$CO, CONR$_5$CR$_{2a}$R$_{2b}$, CR$_2$R$_{2a}$CR$_{2b}$R$_{2c}$S, CR$_2$R$_{2a}$CR$_{2b}$R$_{2c}$SO, CR$_2$R$_{2a}$CR$_{2b}$R$_{2c}$SO$_2$, provided that L is not a bond when W is phenyl;

$R_2$, $R_{2a}$, $R_{2b}$ and $R_{2c}$ are independently hydrogen, halogen, alkyl or haloalkyl;

or alternatively any two $R_2$, $R_{2a}$, $R_{2b}$, and $R_{2c}$ can be taken together to which the atom they are attached to form a cycloalkyl, halogen substituted cycloalkyl or heterocyclyl ring;

$R_3$, $R_{3a}$ and $R_{3b}$ are independently hydrogen, halogen, —OH, —CN, —NO$_2$, —CO$_2$R$_{2a}$, —CONR$_2$R$_{2a}$, —SO$_2$NR$_2$R$_{2a}$, —SOR$_{2a}$, —SO$_2$R$_{2a}$, —NR$_2$SO$_2$R$_6$, —NR$_2$CO$_2$R$_6$, alkyl, haloalkyl, cycloalkyl, alkoxy, aryloxy, alkenyl, haloalkoxy, alkylthio, arylthio, arylsulfonyl, alkylamino, aminoalkyl, arylamino, heteroarylamino, aryl, heteroaryl or heterocyclyl, wherein the aryl, heteroaryl or heterocyclyl may be optionally substituted with $R_7$, $R_{7a}$, $R_{7b}$, and $R_{7c}$;

$R_4$ is bicyclo[2,2,2]octyl or bicyclo[2,2,1]heptyl, both of which may be optionally substituted with one or more substituents selected from halogen, —OH, —OR$_6$, —SR$_6$, —OCOR$_6$, —CN, —NR$_5$COR$_6$, —NR$_5$SO$_2$R$_6$, —COR$_6$, —CO$_2$R$_6$, —CO$_2$H, —OCONR$_2$R$_{2a}$, —CONR$_2$R$_{2a}$, —NR$_5$CO$_2$R$_6$, —SO$_2$R$_6$, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$; or $R_4$ is cycloalkyl, other than bicyclo[2,2,2]octyl or bicyclo [2,2,1]heptyl, which may be optionally substituted with one or more substituents selected from halogen, —OH, —OR$_6$, —SR$_6$, —OCOR$_6$, —CN, —NR$_5$COR$_6$, —NR$_5$SO$_2$R$_6$, —COR$_6$, —CO$_2$R$_6$, —CO$_2$H, —OCONR$_2$R$_{2a}$, —CONR$_2$R$_{2a}$, —NR$_5$CO$_2$R$_6$, —SO$_2$R$_6$, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$; or $R_4$ is heterocyclyl, which may be optionally substituted with one or more substituents selected from halogen, —OH, —OR$_6$, —SR$_6$, —OCOR$_6$, —CN, —NR$_5$COR$_6$, —NR$_5$SO$_2$R$_6$, —COR$_6$, —CO$_2$R$_6$, —CO$_2$H, —OCONR$_2$R$_{2a}$, —CONR$_2$R$_{2a}$, —NR$_5$CO$_2$R$_6$, —SO$_2$R$_6$, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$;

$R_5$, at each occurrence, is independently hydrogen, alkyl, cycloalkyl, aryl, haloalkyl, COR$_{2a}$, CO$_2$R$_{2a}$, SO$_2$NR$_2$R$_{2a}$, or SO$_2$R$_{2a}$;

$R_6$, at each occurrence, is independently alkyl, cycloalkyl, aryl or heteroaryl, all of which may be optionally substituted with $R_7$, $R_{7a}$, $R_{7b}$, and $R_{7c}$; and $R_7$, $R_{7a}$, $R_{7b}$, and $R_{7c}$, at each occurrence, are independently halo, alkyl, haloalkyl, alkoxy, aryl, aryloxy, arylaryl, arylalkyl, arylalkyloxy, alkenyl, cycloalkyl, cycloalkylalkyl, cycloalkylalkyloxy, amino, —OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —NO$_2$, —CN or thiol.

In another embodiment, compounds of formula I are those in which W is aryl, which is optionally substituted with $R_1$, $R_{1a}$, $R_{1b}$, $R_{1c}$ and $R_{1d}$.

In another embodiment, compounds of formula I are those in which W is phenyl, which is optionally substituted with $R_1$, $R_{1a}$, $R_{1b}$, $R_{1c}$ and $R_{1d}$.

In another embodiment, compounds of formula I are those in which:

W is aryl, cycloalkyl or heteroaryl, all of which may be optionally substituted with $R_1$, $R_{1a}$, $R_{1b}$, $R_{1c}$, and $R_{1d}$;

$R_1$, $R_{1a}$, $R_{1b}$, $R_{1c}$ and $R_{1d}$ are independently hydrogen, halogen, —OH, —CN, —$NO_2$, —$CO_2R_{2a}$, —$CONR_2R_{2a}$, —$SO_2NR_2R_{2a}$, $SOR_{2a}$, $SO_2R_{2a}$, —$NR_2SO_2R_6$, —$NR_2CO_2R_6$, alkyl, haloalkyl, cycloalkyl, alkoxy, aryloxy, alkenyl, haloalkoxy, alkylthio, arylthio, arylsulfonyl, alkylamino, aminoalkyl, arylamino, heteroarylamino, aryl, heteroaryl or heterocyclyl, wherein the aryl, heteroaryl or heterocyclyl may be optionally substituted with $R_7$, $R_{7a}$, $R_{7b}$, and $R_{7c}$;

L is a bond, O, S, SO, $SO_2$, $NR_2$, $CR_2R_{2a}$, $CR_2R_{2a}CR_{2b}R_{2c}$, $SO_2NR_2$, $OCR_2R_{2a}$, $CR_2R_{2a}O$, $SCR_2R_{2a}$, $CR_2R_{2a}S$, $SOCR_2R_{2a}$, $SO_2CR_2R_{2a}$, $CR_2R_{2a}OCR_{2b}R_{2c}$, $CR_2R_{2a}SCR_{2b}R_{2c}$, $CR_2R_{2a}SO_2CR_{2b}R_{2c}$, $SO_2NR_{2c}R_{2a}R_{2b}$ or $CONR_5CR_{2a}R_{2b}$;

$R_2$, $R_{2a}$, $R_{2b}$ and $R_{2c}$ are independently hydrogen, halogen, alkyl or haloalkyl;

$R_3$, $R_{3a}$ and $R_{3b}$ are independently hydrogen, halogen, —OH, —CN, —$NO_2$, —$CO_2R_{2a}$, —$CONR_2R_{2a}$, —$SO_2NR_2R_{2a}$, —$SOR_{2a}$, —$SO_2R_{2a}$, —$NR_2SO_2R_6$, —$NR_2CO_2R_6$, alkyl, haloalkyl, cycloalkyl, alkoxy, aryloxy, alkenyl, haloalkoxy, alkylthio, arylthio, arylsulfonyl, alkylamino, aminoalkyl, arylamino, heteroarylamino, aryl, heteroaryl or heterocyclyl, wherein the aryl, heteroaryl or heterocyclyl may be optionally substituted with $R_7$, $R_{7a}$, $R_{7b}$, and $R_{7c}$;

$R_4$ is bicyclo[2,2,2]octyl or bicyclo[2,2,1]heptyl, both of which may be optionally substituted with one or more substituents selected from halogen, —OH, —$OR_6$, —$SR_6$, —$OCOR_6$, —CN, —$NR_5COR_6$, —$NR_5SO_2R_6$, —$COR_6$, —$CO_2R_6$, —$CO_2H$, —$OCONR_2R_{2a}$, —$CONR_2R_{2a}$, —$NR_5CO_2R_6$, —$SO_2R_6$, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$; or $R_4$ is cycloalkyl, other than bicyclo[2,2,2]octyl or bicyclo[2,2,1]heptyl, which may be optionally substituted with one or more substituents selected from halogen, —OH, —$OR_6$, —$SR_6$, —$OCOR_6$, —CN, —$NR_5COR_6$, —$NR_5SO_2R_6$, —$COR_6$, —$CO_2R_6$, —$CO_2H$, —$OCONR_2R_{2a}$, —$CONR_2R_{2a}$, —$NR_5CO_2R_6$, —$SO_2R_6$, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$; or $R_4$ is heterocyclyl, which may be optionally substituted with one or more substituents selected from halogen, —OH, —$OR_6$, —$SR_6$, —$OCOR_6$, —CN, —$NR_5COR_6$, —$NR_5SO_2R_6$, —$COR_6$, —$CO_2R_6$, —$CO_2H$, —$OCONR_2R_{2a}$, —$CONR_2R_{2a}$, —$NR_5CO_2R_6$, —$SO_2R_6$, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$;

$R_5$, at each occurrence, is independently hydrogen, alkyl, cycloalkyl, aryl, haloalkyl, $COR_{2a}$ or $CO_2R_{2a}$;

$R_6$, at each occurrence, is independently alkyl, cycloalkyl, aryl or heteroaryl, all of which may be optionally substituted with $R_7$, $R_{7a}$, $R_{7b}$, and $R_{7c}$; and $R_7$, $R_{7a}$, $R_{7b}$, and $R_{7c}$, at each occurrence, are independently halo, alkyl, haloalkyl, alkoxy, aryl, aryloxy, arylaryl, arylalkyl, arylalkyloxy, alkenyl, cycloalkyl, cycloalkylalkyl, cycloalkylalkyloxy, amino, —OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —$NO_2$, —CN or thiol.

In another embodiment, compounds of formula I are those in which:

W is aryl, cycloalkyl or heteroaryl, all of which may be optionally substituted with $R_1$, $R_{1a}$, $R_{1b}$, $R_{1c}$ and $R_{1d}$;

$R_1$, $R_{1a}$, $R_{1b}$, $R_{1c}$ and $R_{1d}$ are independently hydrogen, halogen, —OH, —CN, —$NO_2$, —$CO_2R_{2a}$, —$CONR_2R_{2a}$, —$SO_2NR_2R_{2a}$, —$SOR_{2a}$, —$SO_2R_{2a}$, alkyl, haloalkyl, cycloalkyl, alkoxy, aryloxy, haloalkoxy, alkylthio, arylthio, arylsulfonyl, alkylamino, aminoalkyl, arylamino, heteroarylamino, aryl, heteroaryl or heterocyclyl, wherein the aryl, heteroaryl or heterocyclyl may be optionally substituted with $R_7$, $R_{7a}$, $R_{7b}$, and $R_{7c}$;

L is a bond, O, S, SO, $SO_2$, $NR_2$, $CR_2R_{2a}$, $CR_2R_{2a}CR_{2b}R_{2c}$, $OCR_2R_{2a}$, $CR_2R_{2a}O$, $SCR_2R_{2a}$, $CR_2R_{2a}S$, $CR_2R_{2a}OCR_{2b}R_{2c}$, $CR_2R_{2a}SCR_{2b}R_{2c}$, $CR_2R_{2a}SO_2CR_{2b}R_{2c}$ or $SO_2NR_{2c}R_{2a}R_{2b}$;

$R_2$, $R_{2a}$, $R_{2b}$ and $R_{2c}$ are independently hydrogen, halogen, alkyl or haloalkyl;

$R_3$, $R_{3a}$ and $R_{3b}$ are independently hydrogen, halogen, —OH, —CN, —$NO_2$, —$CO_2R_{2a}$, —$CONR_2R_{2a}$, —$SO_2NR_2R_{2a}$, —$SOR_{2a}$, —$SO_2R_{2a}$, alkyl, haloalkyl, cycloalkyl, alkoxy, aryloxy, haloalkoxy, alkylthio, arylthio, arylsulfonyl, alkylamino, aminoalkyl, arylamino, heteroarylamino, aryl, heteroaryl or heterocyclyl, wherein the aryl, heteroaryl or heterocyclyl may be optionally substituted with $R_7$, $R_{7a}$, $R_{7b}$, and $R_{7c}$;

$R_4$ is bicyclo[2,2,2]octyl or bicyclo[2,2,1]heptyl, both of which may be optionally substituted with one or more substituents selected from halogen, —OH, —$OR_6$, —$SR_6$, —$OCOR_6$, —CN, —$COR_6$, —$CO_2R_6$, —$CO_2H$, —$OCONR_2R_{2a}$, —$CONR_2R_{2a}$, —$SO_2R_6$, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$; or $R_4$ is cycloalkyl, other than bicyclo[2,2,2]octyl or bicyclo[2,2,1]heptyl, which may be optionally substituted with one or more substituents selected from halogen, —OH, —$OR_6$, —$SR_6$, —$OCOR_6$, —CN, —$COR_6$, —$CO_2R_6$, —$CO_2H$, $OCONR_2R_{2a}$, $CONR_2R_{2a}$, —$SO_2R_6$, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$; or $R_4$ is heterocyclyl, which may be optionally substituted with one or more substituents selected from halogen, —OH, —$OR_6$, —$SR_6$, —$OCOR_6$, —CN, —$COR_6$, —$CO_2R_6$, —$CO_2H$, —$OCONR_2R_{2a}$, —$CONR_2R_{2a}$, —$SO_2R_6$, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$;

$R_6$, at each occurrence, is independently alkyl, cycloalkyl, aryl or heteroaryl, all of which may be optionally substituted with $R_7$, $R_{7a}$, $R_{7b}$, and $R_{7c}$; and $R_7$, $R_{7a}$, $R_{7b}$, and $R_{7c}$, at each occurrence, are independently halo, alkyl, haloalkyl, alkoxy, aryl, aryloxy, arylaryl, arylalkyl, arylalkyloxy, alkenyl, cycloalkyl, cycloalkylalkyl, cycloalkylalkyloxy, amino, —OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —$NO_2$, —CN or thiol.

In yet another embodiment, compounds of formula I are those in which:

W is aryl or heteroaryl, both of which may be optionally substituted with $R_1$, $R_{1a}$, $R_{1b}$, $R_{1c}$, and $R_{1d}$;

$R_1$, $R_{1a}$, $R_{1b}$, $R_{1c}$ and $R_{1d}$ are independently hydrogen, halogen, —OH, —CN, —$NO_2$, —$CO_2R_{2a}$, —$CONR_2R_{2a}$, —$SO_2NR_2R_{2a}$, alkyl, haloalkyl, cycloalkyl, alkoxy, aryloxy, haloalkoxy, alkylthio, arylthio, arylsulfonyl, alkylamino, aminoalkyl, arylamino, heteroarylamino, aryl, heteroaryl or heterocyclyl, wherein the aryl, heteroaryl or heterocyclyl may be optionally substituted with $R_7$, $R_{7a}$, $R_{7b}$, and $R_{7c}$;

L is a bond, O, S, SO, $SO_2$, $CR_2R_{2a}$, $OCR_2R_{2a}$, $CR_2R_{2a}O$, $SO_2NR_2R_{2a}R_{2b}$ or $CR_2R_{2a}OCR_{2b}R_{2c}$;

$R_2$, $R_{2a}$, $R_{2b}$ and $R_{2c}$ are independently hydrogen, halogen, alkyl or haloalkyl;

$R_3$, $R_{3a}$ and $R_{3b}$ are independently hydrogen, halogen, —OH, —CN, —$NO_2$, —$CO_2R_{2a}$, —$CONR_2R_{2a}$, —$SO_2NR_2R_{2a}$, alkyl, haloalkyl, cycloalkyl, alkoxy, aryloxy, haloalkoxy, alkylthio, arylthio, arylsulfonyl, alkylamino, aminoalkyl, arylamino, heteroarylamino, aryl, heteroaryl or heterocyclyl, wherein the aryl, heteroaryl or heterocyclyl may be optionally substituted with $R_7$, $R_{7a}$, $R_{7b}$, and $R_{7c}$;

$R_4$ is bicyclo[2,2,2]octyl or bicyclo[2,2,1]heptyl, both of which may be optionally substituted with one or more substituents selected from halogen, —OH, —$OR_6$, —$SR_6$, —$OCOR_6$, —CN, —$COR_6$, —$CO_2R_6$, —$CO_2H$, —$OCONR_2R_{2a}$, —$CONR_2R_{2a}$, —$SO_2R_6$, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$; or $R_4$ is cycloalkyl, other than bicyclo[2,2,2]octyl or bicyclo[2,2,1]heptyl, which may be optionally substituted with one or more substituents selected from halogen, —OH, —$OR_6$, —$SR_6$, —$OCOR_6$, —CN, —$COR_6$, —$CO_2R_6$, —$CO_2H$, —$OCONR_2R_{2a}$, —$CONR_2R_{2a}$, —$SO_2R_6$, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$; or $R_4$ is heterocyclyl, which may be optionally substituted with one or more substituents selected from halogen, —OH, —$OR_6$, —$SR_6$, —$OCOR_6$, —CN, —$COR_6$, —$CO_2R_6$, —$CO_2H$, —$OCONR_2R_{2a}$, —$CONR_2R_{2a}$, —$SO_2R_6$, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$;

$R_6$, at each occurrence, is independently alkyl, cycloalkyl, aryl or heteroaryl, all of which may be optionally substituted with $R_7$, $R_{7a}$, $R_{7b}$, and $R_{7c}$; and $R_7$, $R_{7a}$, $R_{7b}$, and $R_{7c}$, at each occurrence, are independently halo, alkyl, haloalkyl, alkoxy, aryl, aryloxy, arylaryl, arylalkyl, arylalkyloxy, alkenyl, cycloalkyl, cycloalkylalkyl, cycloalkylalkyloxy, amino, —OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —$NO_2$, —CN or thiol.

In another embodiment, compounds of formula I are those in which:

W is aryl or heteroaryl, both of which may be optionally substituted with $R_1$, $R_{1a}$, $R_{1b}$, $R_{1c}$ and $R_{1d}$;

$R_1$, $R_{1a}$, $R_{1b}$, $R_{1c}$ and $R_{1d}$ are independently hydrogen, halogen, —OH, —CN, —$NO_2$, —$CO_2R_{2a}$, alkyl, haloalkyl, cycloalkyl, alkoxy, aryloxy, haloalkoxy, alkylthio, arylthio, arylsulfonyl, alkylamino, aminoalkyl, arylamino, heteroarylamino, aryl, heteroaryl or heterocyclyl, wherein the aryl, heteroaryl or heterocyclyl may be optionally substituted with $R_7$, $R_{7a}$, $R_{7b}$, and $R_{7c}$;

L is a bond, O, S, SO, $SO_2$, $CR_2R_{2a}$, $OCR_2R_{2a}$, $CR_2R_{2a}O$, $SO_2NR_2R_{2a}R_{2b}$ or $CR_2R_{2a}OCR_{2b}R_{2c}$;

$R_2$, $R_{2a}$, $R_{2b}$ and $R_{2c}$ are independently hydrogen, halogen, alkyl or haloalkyl;

$R_3$, $R_{3a}$ and $R_{3b}$ are independently hydrogen, halogen, —OH, —CN, —$NO_2$, —$CO_2R_{2a}$, alkyl, haloalkyl, cycloalkyl, alkoxy, aryloxy, haloalkoxy, alkylthio, arylthio, arylsulfonyl, alkylamino, aminoalkyl, arylamino, heteroarylamino, aryl, heteroaryl or heterocyclyl, wherein the aryl, heteroaryl or heterocyclyl may be optionally substituted with $R_7$, $R_{7a}$, $R_{7b}$, and $R_{7c}$;

$R_4$ is bicyclo[2,2,2]octyl or bicyclo[2,2,1]heptyl, both of which may be optionally substituted with one or more substituents selected from halogen, —OH, —$OR_6$, —$SR_6$, —CN, —$COR_6$, —$CO_2R_6$, —$CO_2H$, —$CONR_2R_{2a}$, —$SO_2R_6$, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$; or $R_4$ is cycloalkyl, other than bicyclo[2,2,2]octyl or bicyclo[2,2,1]heptyl, which may be optionally substituted with one or more substituents selected from halogen, —OH, —$OR_6$, —$SR_6$, —CN, —$COR_6$, —$CO_2R_6$, —$CO_2H$, —$CONR_2R_{2a}$, —$SO_2R_6$, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$; or $R_4$ is heterocyclyl, which may be optionally substituted with one or more substituents selected from halogen, —OH, —$OR_6$, —$SR_6$, —CN, —$COR_6$, —$CO_2R_6$, —$CO_2H$, —$CONR_2R_{2a}$, —$SO_2R_6$, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$;

$R_6$, at each occurrence, is independently alkyl, cycloalkyl, aryl or heteroaryl, all of which may be optionally substituted with $R_7$, $R_{7a}$, $R_{7b}$, and $R_{7c}$; and $R_7$, $R_{7a}$, $R_{7b}$, and $R_{7c}$, at each occurrence, are independently halo, alkyl, haloalkyl, alkoxy, aryl, aryloxy, arylaryl, arylalkyl, arylalkyloxy, alkenyl, cycloalkyl, cycloalkylalkyl, cycloalkylalkyloxy, amino, —OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —$NO_2$, —CN or thiol.

In still yet another embodiment, compounds of formula I are those in which:

W is aryl, which is optionally substituted with $R_1$, $R_{1a}$, $R_{1b}$, $R_{1c}$ and $R_{1d}$;

$R_1$, $R_{1a}$, $R_{1b}$, $R_{1c}$ and $R_{1d}$ are independently hydrogen, halogen, —OH, —CN, —$NO_2$, alkyl, haloalkyl, cycloalkyl, alkoxy, aryloxy, haloalkoxy, alkylthio, arylthio, arylsulfonyl, alkylamino, aminoalkyl, arylamino, heteroarylamino, aryl, heteroaryl or heterocyclyl, wherein the aryl, heteroaryl or heterocyclyl may be optionally substituted with $R_7$, $R_{7a}$, $R_{7b}$, and $R_{7c}$;

L is a bond, O, S, SO, $SO_2$, $CR_2R_{2a}$, $OCR_2R_{2a}$, $CR_2R_{2a}O$, $SO_2NR_2R_{2a}R_{2b}$ or $CR_2R_{2a}OCR_{2b}R_{2c}$;

$R_2$, $R_{2a}$, $R_{2b}$ and $R_{2c}$ are independently hydrogen, halogen, alkyl or haloalkyl;

$R_3$, $R_{3a}$ and $R_{3b}$ are independently hydrogen, halogen, —OH, —CN, —$NO_2$, alkyl, haloalkyl, cycloalkyl, alkoxy, aryloxy, haloalkoxy, alkylthio, arylthio, arylsulfonyl, alkylamino, aminoalkyl, arylamino, heteroarylamino, aryl, heteroaryl or heterocyclyl, wherein the aryl, heteroaryl or heterocyclyl may be optionally substituted with $R_7$, $R_{7a}$, $R_{7b}$, and $R_{7c}$;

$R_4$ is bicyclo[2,2,2]octyl or bicyclo[2,2,1]heptyl, both of which may be optionally substituted with one or more substituents selected from halogen, —OH, —$OR_6$, —$SR_6$, —CN, —$COR_6$, —$CO_2R_6$, —$CO_2H$, —$CONR_2R_{2a}$, —$SO_2R_6$, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$; or $R_4$ is cycloalkyl, other than bicyclo[2,2,2]octyl or bicyclo[2,2,1]heptyl, which may be optionally substituted with one or more substituents selected from halogen, —OH, —$OR_6$, —$SR_6$, —CN, —$COR_6$, —$CO_2R_6$, —$CO_2H$, $CONR_2R_{2a}$, —$SO_2R_6$, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$;

$R_6$, at each occurrence, is independently alkyl, cycloalkyl, aryl or heteroaryl, all of which may be optionally substituted with $R_7$, $R_{7a}$, $R_{7b}$, and $R_{7c}$; and $R_7$, $R_{7a}$, $R_{7b}$, and $R_{7c}$, at each occurrence, are independently halo, alkyl, haloalkyl, alkoxy, aryl, aryloxy, arylaryl, arylalkyl, arylalkyloxy, alkenyl, cycloalkyl, cycloalkylalkyl, cycloalkylalkyloxy, amino, —OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —$NO_2$, —CN or thiol.

In one embodiment, compounds of formula I are those in which:

W is aryl, which is optionally substituted with $R_1$, $R_{1a}$, $R_{1b}$, $R_{1c}$ and $R_{1d}$;

$R_1$, $R_{1a}$, $R_{1b}$, $R_{1c}$ and $R_{1d}$ are hydrogen, halogen, —OH, —CN, —$NO_2$, alkyl, haloalkyl, cycloalkyl, alkoxy, aryloxy, haloalkoxy, alkylthio, arylthio, arylsulfonyl, alkylamino, aminoalkyl, aryl, heteroaryl or heterocyclyl, wherein the aryl, heteroaryl or heterocyclyl may be optionally substituted with $R_7$, $R_{7a}$, $R_{7b}$, and $R_{7c}$;

L is a bond, O, S, $CR_2R_{2a}$, $OCR_2R_{2a}$, $CR_2R_{2a}O$ or $CR_2R_{2a}OCR_{2b}R_{2c}$;

$R_2$, $R_{2a}$, $R_{2b}$ and $R_{2c}$ are independently hydrogen, halogen, alkyl or haloalkyl;

$R_3$, $R_{3a}$ and $R_{3b}$ are independently hydrogen, halogen, —OH, —CN, —$NO_2$, alkyl, haloalkyl, cycloalkyl, alkoxy, aryloxy, haloalkoxy, alkylthio, arylthio, arylsulfonyl, alkylamino, aminoalkyl, aryl, heteroaryl or heterocyclyl, wherein the aryl, heteroaryl or heterocyclyl may be optionally substituted with $R_7$, $R_{7a}$, $R_{7b}$, and $R_{7c}$;

$R_4$ is bicyclo[2,2,2]octyl or bicyclo[2,2,1]heptyl, both of which may be optionally substituted with one or more substituents selected from halogen, —OH, —$OR_6$, —$SR_6$, —CN, —$COR_6$, —$CO_2R_6$, —$CO_2H$, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$; or $R_4$ is cycloalkyl, other than bicyclo[2,2,2]octyl or bicyclo[2,2,1]heptyl, which may be optionally substituted with one or more substituents selected from halogen, —OH, —$OR_6$, —$SR_6$, —CN, —$COR_6$, —$CO_2R_6$, —$CO_2H$, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$;

$R_6$, at each occurrence, is independently alkyl, cycloalkyl, aryl or heteroaryl; and $R_7$, $R_{7a}$, $R_{7b}$, and $R_{7c}$, at each occurrence, are independently halo, alkyl, haloalkyl, alkoxy, aryl, aryloxy, arylaryl, arylalkyl, arylalkyloxy, alkenyl, cycloalkyl, cycloalkylalkyl, cycloalkylalkyloxy, amino, —OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —$NO_2$, —CN or thiol.

In still yet another embodiment, compounds of formula I are those in which:

W is phenyl, which is optionally substituted with $R_1$, $R_{1a}$, $R_{1b}$, $R_{1c}$ and $R_{1d}$;

$R_1$, $R_{1a}$, $R_{1b}$, $R_{1c}$ and $R_{1d}$ are independently hydrogen, halogen, —OH, —CN, —$NO_2$, alkyl, haloalkyl, cycloalkyl, alkoxy, aryloxy, haloalkoxy, alkylthio, arylthio, arylsulfonyl, alkylamino, aminoalkyl, aryl, heteroaryl or heterocyclyl;

L is O, S, $SCH_2$, $OCH_2$, $CH_2O$ or $CH_2OCH_2$;

$R_3$, $R_{3a}$ and $R_{3b}$ are independently hydrogen, halogen, —OH, —CN, —$NO_2$, alkyl, haloalkyl, cycloalkyl, alkoxy, aryloxy, haloalkoxy, alkylthio, arylthio, arylsulfonyl, alkylamino, aminoalkyl, aryl, heteroaryl or heterocyclyl;

$R_4$ is bicyclo[2,2,2]octyl or bicyclo[2,2,1]heptyl, all which may be optionally substituted with one or more substituents selected from halogen, —OH, —$OR_6$, —$SR_6$, —CN, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$;

$R_6$, at each occurrence, is independently alkyl, cycloalkyl, aryl or heteroaryl; and $R_7$, $R_{7a}$, $R_{7b}$, and $R_{7c}$, at each occurrence, are independently halo, alkyl, haloalkyl, alkoxy, aryl, aryloxy, arylalkyl, cycloalkyl, amino, —OH, hydroxyalkyl, heteroaryl, heteroaryloxy, heteroarylalkyl, alkylthio, arylalkylthio, —$NO_2$, or —CN.

In still yet another embodiment, compounds of formula I are those in which L is O.

In still yet another embodiment, compounds of formula I are those in which $R_4$ is bicyclo[2,2,2]octyl or bicyclo[2,2,1]heptyl, both of which may be optionally substituted with one or more substituents selected from halogen, —OH, —$OR_6$, —$SR_6$, —$OCOR_6$, —CN, —$NR_5COR_6$, —$NR_5SO_2R_6$, —$COR_6$, —$CO_2R_6$, —$CO_2H$, —$OCONR_2R_{2a}$, —$CONR_2R_{2a}$, —$NR_5CO_2R_6$, —$SO_2R_6$, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$.

In another embodiment, compounds of formula I are those compounds having formula IA:

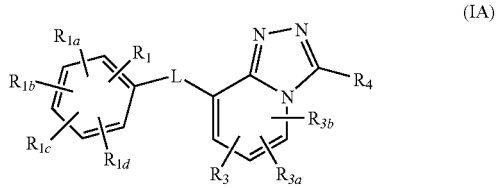

(IA)

wherein:

L is selected from O, S, $OCH_2$, $CH_2OCH_2$ and $SO_2NHCH_2$; and $R_3$, $R_{3a}$ and $R_{3b}$ are independently selected from hydrogen, halogen, $CF_3$, $OCF_3$, alkyl or alkoxyl.

In another embodiment, compounds of formula I are those compounds having formula IA in which:

$R_1$, $R_{1a}$, $R_{1b}$, $R_{1c}$, and $R_{1d}$ are independently hydrogen, halogen, alkyl, haloalkyl, cycloalkyl, alkoxy, alkenyl, haloalkoxy, aryl, heteroaryl or heterocyclyl;

L is O;

$R_3$, $R_{3a}$ and $R_{3b}$ are independently selected from hydrogen or halogen; and $R_4$ is bicyclo[2,2,2]octyl or bicyclo[2,2,1]heptyl, both of which may be optionally substituted with one or more substituents selected from halogen, OH, $OR_6$, $OCOR_6$, haloalkyl, haloalkoxy, ary, heterocyclyl; and $R_6$ is alkyl, or cycloalkyl.

In another embodiment, compounds of formula I are those compounds having formula IA in which:

L is selected from 0, $OCH_2$ and $CH_2OCH_2$;

$R_4$ is bicyclo[2,2,2]octyl or bicyclo[2,2,1]heptyl, both of which may be optionally substituted with one or more substituents selected from halogen, —OH, —$OR_6$, —$SR_6$, —$OCOR_6$, —CN, —$NR_5COR_6$, —$NR_5SO_2R_6$, —$COR_6$, —$CO_2R_6$, —$CO_2H$, —$OCONR_2R_{2a}$, —$CONR_2R_{2a}$, —$NR_5CO_2R_6$, —$SO_2R_6$, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$; or $R_4$ is cycloalkyl, other than bicyclo[2,2,2]octyl or bicyclo[2,2,1]heptyl, which may be optionally substituted with one or more substituents selected from halogen, —OH, —$OR_6$, —$SR_6$, —$OCOR_6$, —CN, —$NR_5COR_6$, —$NR_5SO_2R_6$, —$COR^r$, —$CO_2R_6$, —$CO_2H$, —$OCONR_2R_{2a}$, —$CONR_2R_{2a}$, —$NR_5CO_2R_6$, —$SO_2R_6$, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$; and $R_6$, at each occurrence, is independently alkyl or cycloalkyl.

In another embodiment, compounds of formula I are those compounds having formula IA in which:

L is selected from 0, $OCH_2$ and $CH_2OCH_2$;

$R_4$ is a fused or bridged cycloalkyl, other than bicyclo[2,2,2]octyl or bicyclo[2,2,1]heptyl, which may be optionally substituted with one or more substituents selected from halogen, —OH, —$OR_6$, —$SR_6$, —$OCOR_6$, —CN, —$NR_5COR_6$, —$NR_5SO_2R_6$, —$COR_6$, —$CO_2R_6$, —$CO_2H$, —$OCONR_2R_{2a}$, —$CONR_2R_{2a}$, —$NR_5CO_2R_6$, —$SO_2R_6$, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$; and $R_6$, at each occurrence, is independently alkyl or cycloalkyl.

In another embodiment, compounds of the present invention are selected from the compounds exemplified in the examples, such as, Examples 9, 11 and 100-113.

In another embodiment, the present invention relates to pharmaceutical compositions comprised of a therapeutically effective amount of a compound of the present invention, alone or, optionally, in combination with a pharmaceutically acceptable carrier and/or one or more other agent(s).

In another embodiment, the present invention relates to methods of inhibiting the activity of the enzyme 11-beta-hydroxysteroid dehydrogenase type I comprising administering to a mammalian patient, for example, a human patient, in need thereof a therapeutically effective amount of a compound of the present invention, alone, or optionally, in combination with another compound of the present invention and/or at least one other type of therapeutic agent.

In another embodiment, the present invention relates to a method for preventing, inhibiting, or treating the progression or onset of diseases or disorders associated with the activity of the enzyme 11-beta-hydroxysteroid dehydrogenase type I comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

Examples of diseases or disorders associated with the activity of the enzyme 11-beta-hydroxysteroid dehydrogenase type I that can be prevented, inhibited, or treated according to the present invention include, but are not limited to, diabetes, hyperglycemia, impaired glucose tolerance, insulin resistance, hyperinsulinemia, retinopathy, neuropathy, nephropathy, delayed wound healing, atherosclerosis, acute coronary syndrome, myocardial infarction, angina pectoris, peripheral vascular disease, intermittent claudication, abnormal heart function, myocardial ischemia, stroke, Metabolic Syndrome, hypertension, obesity, dyslipidemia, hyperlipidemia, hypertriglyceridemia, hypercholesterolemia, low HDL, high LDL, non-cardiac ischemia, infection, cancer, vascular restenosis, pancreatitis, neurodegenerative disease, lipid disorders, cognitive impairment and dementia, bone disease, HIV protease associated lipodystrophy, glaucoma, rheumatoid arthritis and osteoarthritis.

In another embodiment, the present invention relates to a method for preventing, inhibiting, or treating the progression or onset of diabetes, hyperglycemia, obesity, dyslipidemia, hypertension, cognitive impairment, rheumatoid arthritis, osteoarthritis, glaucoma and Metabolic Syndrome comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In still another embodiment, the present invention relates to a method for preventing, inhibiting, or treating the progression or onset of diabetes, comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In yet still another embodiment, the present invention relates to a method for preventing, inhibiting, or treating the progression or onset of hyperglycemia comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In another embodiment, the present invention relates to a method for preventing, inhibiting, or treating the progression or onset of obesity comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In one embodiment, the present invention relates to a method for preventing, inhibiting, or treating the progression or onset of dyslipidemia comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In another embodiment, the present invention relates to a method for preventing, inhibiting, or treating the progression or onset of hypertension comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In another embodiment, the present invention relates to a method for preventing, inhibiting, or treating the progression or onset of cognitive impairment comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In another embodiment, the present invention relates to a method for preventing, inhibiting, or treating the progression or onset of rheumatoid arthritis comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In another embodiment, the present invention relates to a method for preventing, inhibiting, or treating the progression or onset of osteoarthritis comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In another embodiment, the present invention relates to a method for preventing, inhibiting, or treating the progression or onset of Metabolic Syndrome comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In another embodiment, the present invention relates to a method for preventing, inhibiting, or treating the progression or onset of glaucoma comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms, and all geometric isomeric forms of a structure are intended, unless the specific stereochemistry or isomeric form is specifically indicated.

The term "substituted," as used herein, means that any one or more hydrogens on the designated atom or ring is replaced with a selection from the indicated group, provided that the designated atom's normal valency is not exceeded, and that the substitution results in a stable compound. When a substituent is keto (i.e., =O), then 2 hydrogens on the atom are replaced.

When any variable (e.g., $R^a$) occurs more than one time in any constituent or formula for a compound, its definition at each occurrence is independent of its definition at every other occurrence. Thus, for example, if a group is shown to be substituted with 0-2 $R^a$, then said group may optionally be substituted with up to two $R^a$ groups and $R^a$ at each occurrence is selected independently from the definition of $R^a$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

Unless otherwise indicated, the term "lower alkyl," "alkyl," or "alk" as employed herein alone or as part of another group includes both straight and branched chain hydrocarbons, containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like as well as such groups may optionally include 1 to 4 substituents such as halo, for example F, Br, Cl, or I, or $CF_3$, alkyl, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol, haloalkyl, trihaloalkyl, and/or alkylthio.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclic alkyl, bicyclic alkyl (or bicycloalkyl) and tricyclic alkyl, containing a total of 3 to 20 carbons forming the ring, preferably 3 to 10 carbons, forming the ring and which may be fused to 1 or 2 aromatic rings as described for aryl, which includes cyclopropyl, cyclobutyl, cyclopentyl, cyclohexyl, cycloheptyl, cyclooctyl, cyclodecyl and cyclododecyl, cyclohexenyl,

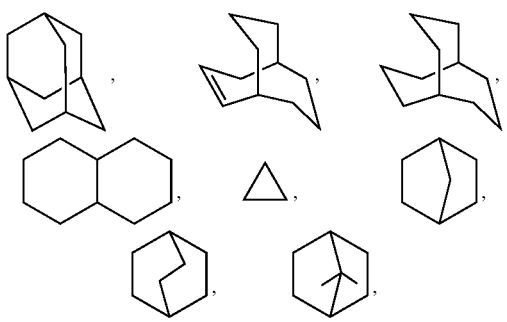

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol, and/or alkylthio, and/or any of the substituents for alkyl.

Unless otherwise indicated, the term "lower alkenyl" or "alkenyl" as used herein by itself or as part of another group refers to straight or branched chain radicals of 2 to 20 carbons, preferably 2 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonyl-amino, nitro, cyano, thiol, alkylthio, and/or any of the alkyl substituents set out herein.

Unless otherwise indicated, the term "lower alkynyl" or "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl, and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, and/or any of the alkyl substituents set out herein.

Where alkyl groups as defined above have single bonds for attachment to other groups at two different carbon atoms, they are termed "alkylene" groups and may optionally be substituted as defined above for "alkyl".

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

The term "halogen" or "halo" as used herein alone or as part of another group refers to chlorine, bromine, fluorine, and iodine as well as $CF_3$, with chlorine or fluorine being preferred.

Unless otherwise indicated, the term "aryl" as employed herein alone or as part of another group refers to monocyclic and bicyclic aromatic groups containing 6 to 10 carbons in the ring portion (such as phenyl or naphthyl, including 1-naphthyl and 2-naphthyl) and may optionally include 1 to 3 additional rings fused to a carbocyclic ring or a heterocyclic ring (such as aryl, cycloalkyl, heteroaryl, or cycloheteroalkyl rings for example

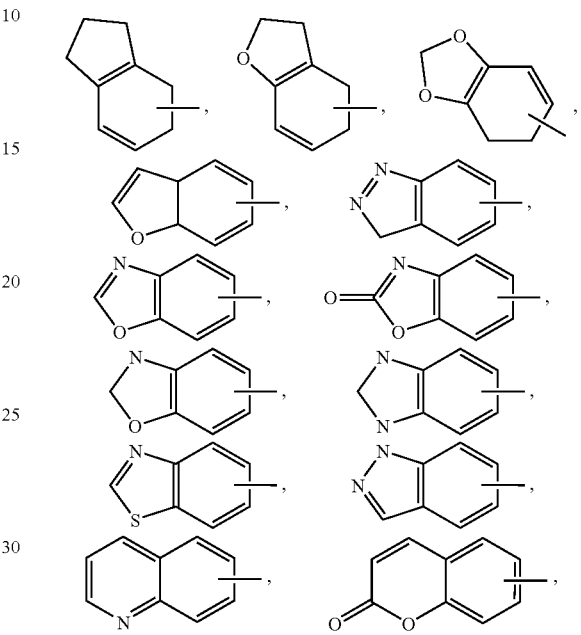

and may be optionally substituted through available carbon atoms with 1, 2, or 3 substituents, for example, hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl, or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino, or arylsulfonaminocarbonyl, and/or any of the alkyl substituents set out herein.

Unless otherwise indicated, the term "lower alkoxy", "alkoxy", "aryloxy" or "aralkoxy" as employed herein alone or as part of another group includes any of the above alkyl, aralkyl, or aryl groups linked to an oxygen atom.

Unless otherwise indicated, the term "amino" as employed herein alone or as part of another group refers to amino that may be substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl, or thioalkyl. These substituents may be further substituted with a carboxylic acid and/or any of the $R^1$ groups or substituents for $R^1$ as set out above. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, alkoxy, alkylthio, halo, trifluoromethyl, or hydroxy.

Unless otherwise indicated, the term "lower alkylthio," "alkylthio," "arylthio," or "aralkylthio" as employed herein alone or as part of another group includes any of the above alkyl, aralkyl, or aryl groups linked to a sulfur atom.

Unless otherwise indicated, the term "lower alkylamino," "alkylamino," "arylamino," or "arylalkylamino" as employed herein alone or as part of another group includes any of the above alkyl, aryl, or arylalkyl groups linked to a nitrogen atom.

As used herein, the term "heterocyclyl" or "heterocyclic system" is intended to mean a stable 4- to 12-membered monocyclic or bicyclic heterocyclic ring which is saturated, or partially unsaturated, and which consists of carbon atoms and 1, 2, 3, or 4 heteroatoms independently selected from the group consisting of N, NH, O, and S, and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another.

Unless otherwise indicated, the term "heteroaryl" as used herein alone or as part of another group refers to a 5- or 12-membered aromatic ring, prefereably, a 5- or 6-membered aromatic ring, which includes 1, 2, 3, or 4 hetero atoms such as nitrogen, oxygen, or sulfur, and such rings fused to an aryl, cycloalkyl, heteroaryl, or cycloheteroalkyl ring (e.g. benzothiophenyl, indolyl), and includes possible N-oxides. The heteroaryl group may optionally include 1 to 4 substituents such as any of the substituents set out above for alkyl. Examples of heteroaryl groups include the following:

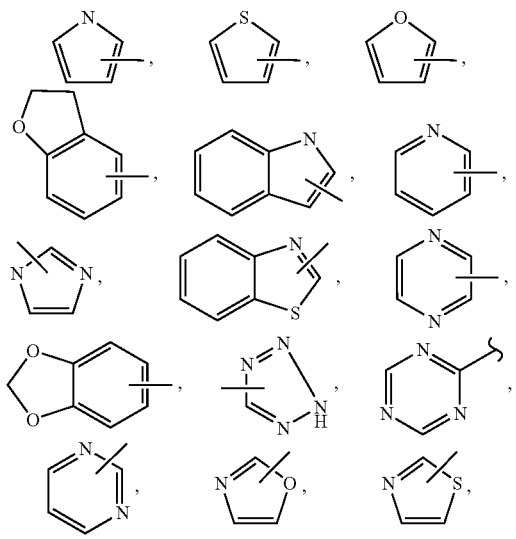

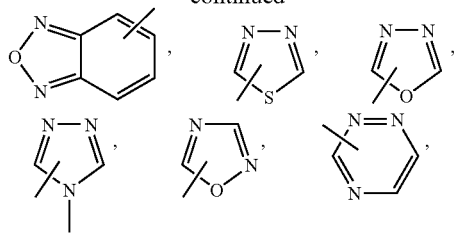

-continued and the like.

The term "heterocyclylalkyl" or "heterocyclyl" as used herein alone or as part of another group refers to heterocyclyl groups as defined above linked through a C atom or heteroatom to an alkyl chain.

The term "heteroarylalkyl" or "heteroarylalkenyl" as used herein alone or as part of another group refers to a heteroaryl group as defined above linked through a C atom or heteroatom to an alkyl chain, alkylene, or alkenylene as defined above.

The term "cyano" as used herein, refers to a —CN group.

The term "nitro" as used herein, refers to an —NO₂ group.

The term "hydroxy" as used herein, refers to an —OH group.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

Any compound that can be converted in vivo to provide the bioactive agent (i.e., the compound of formula I) is a prodrug within the scope and spirit of the invention.

The term "prodrugs" as employed herein includes phosphates, esters and carbonates formed by reacting one or more hydroxyls of compounds of formula I with alkyl, alkoxy, or aryl substituted acylating or phosphorylating agents employing procedures known to those skilled in the art to generate phosphates, acetates, pivalates, methylcarbonates, benzoates, and the like.

Various forms of prodrugs are well known in the art and are described in:

a) *The Practice of Medicinal Chemistry*, Camille G. Wermuth et al., Ch. 31, (Academic Press, 1996);

b) *Design of Prodrugs*, edited by H. Bundgaard, (Elsevier, 1985);

c) *A Textbook of Drug Design and Development*, P. Krogsgaard-Larson and H. Bundgaard, eds. Ch. 5, pp. 113-191 (Harwood Academic Publishers, 1991); and d) *Hydrolysis in Drug and Prodrug Metabolism*, Bernard Testa and Joachim M. Mayer, (Wiley-VCH, 2003).

Said references are incorporated herein by reference.

In addition, compounds of the formula I are, subsequent to their preparation, preferably isolated and purified to obtain a composition containing an amount by weight equal to or greater than 99% formula I compound ("substantially pure" compound I), which is then used or formulated as described herein. Such "substantially pure" compounds of the formula I are also contemplated herein as part of the present invention.

All stereoisomers of the compounds of the instant invention are contemplated, either in admixture or in pure or substantially pure form. The compounds of the present invention can have asymmetric centers at any of the carbon atoms including any one of the R substituents and/or exhibit polymorphism. Consequently, compounds of formula I can exist in enantiomeric, or diastereomeric forms, or in mixtures thereof. The processes for preparation can utilize racemates, enantiomers, or diastereomers as starting materials. When diastereomeric or enantiomeric products are prepared, they can be separated by conventional methods for example, chromatographic or fractional crystallization.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to inhibit 11beta-HSD1 or effective to treat or prevent diseases or disorders associated with 11beta-HSD1.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

Synthesis

Compounds of formula I of may be prepared as shown in the following reaction schemes and description thereof, as well as relevant literature procedures that may be used by one skilled in the art. Exemplary reagents and procedures for these reactions appear hereinafter and in the working Examples.

SCHEME I

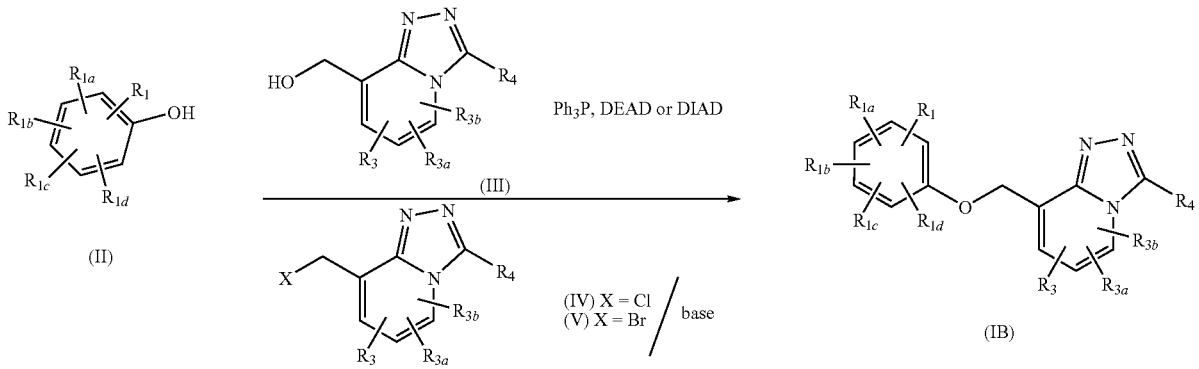

Scheme I describes a method for preparing compounds of formula IB (a subset of compounds of formula I). A phenol intermediate II can be obtained commercially, prepared by methods known in the literature or by other methods known to one skilled in the art. Formation of a compound IB can be carried out from a phenol II and an alcohol III using triphenylphosphine and DEAD or DIAD, commonly known as Mitsunobu Reaction. Alternatively, compound IB can be obtained from alkylation of a phenol II with a chloride IV or a bromide V in the presence of an appropriate base, such as cesium carbonate, potassium carbonate, sodium carbonate or DIEA.

SCHEME II

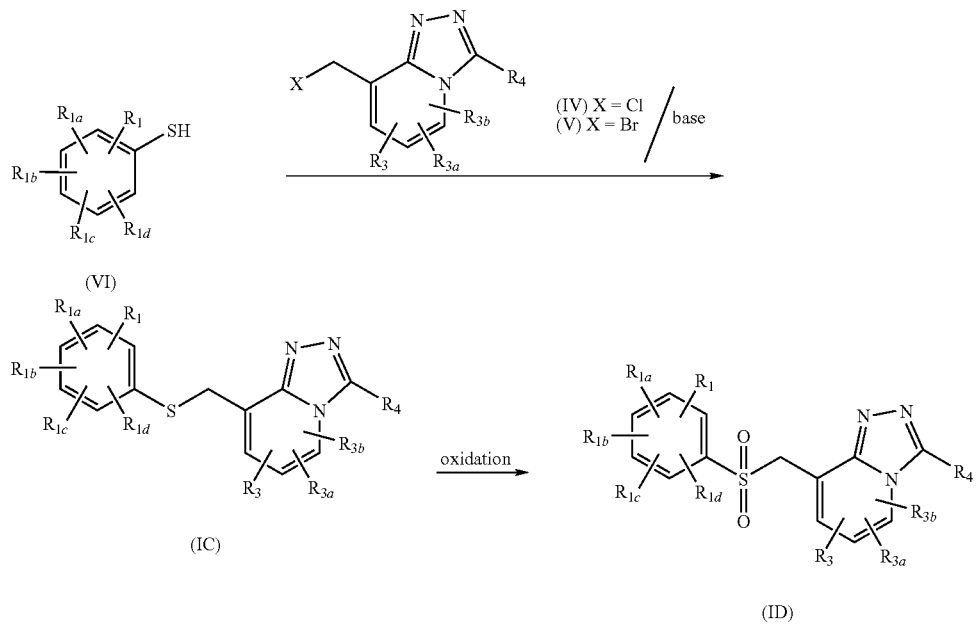

Scheme II describes a method for preparing compounds of formula IC and formula ID (subsets of compounds of formula I). A thiophenol intermediate VI can be obtained commercially, prepared by methods known in the literature or by other methods known to one skilled in the art. Formation of a compound IC can be obtained from alkylation of a thiophenol VI with a chloride IV or a bromide V in the presence of an appropriate base, such as sodium carbonate or DIEA. Subsequent oxidation of a compound 1C with an appropriate oxidizing reagent such as mCPBA, Oxone®, p-toluenesulfonic peracid generated in situ (*Tetrahedron*, 1996, 52, 5773-5787) or by other reagents known to one skilled in the art provides a compound 1D.

SCHEME III

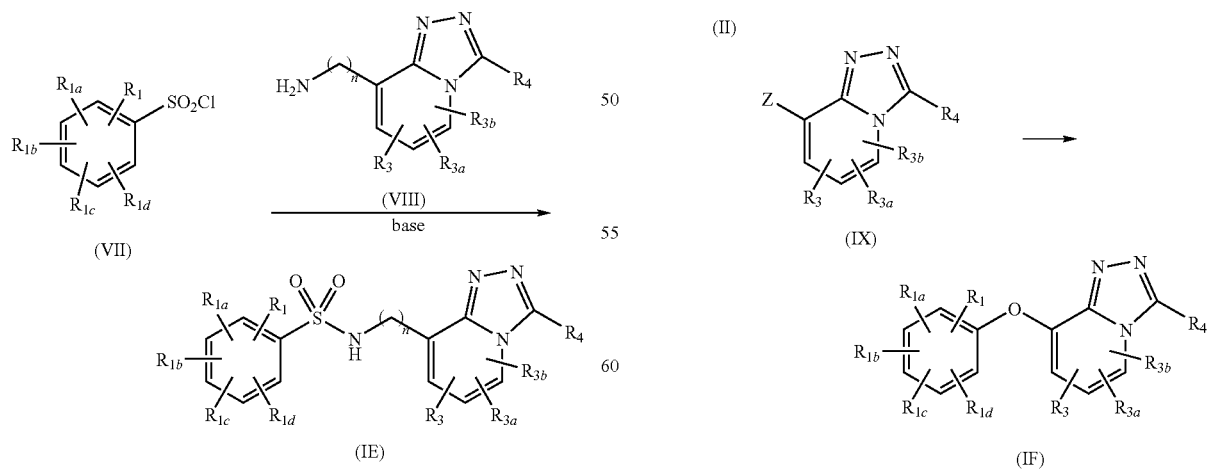

Scheme III describes a method for preparing compounds of formula IE (a subset of compounds of formula I). An arylsulfonyl chloride intermediate VII can be obtained commercially, prepared by methods known in the literature or by other methods known to one skilled in the art. Formation of a compound IE can be achieved from the reaction of a compound of formula VII with an amine VIII in the presence of an appropriate base such as pyridine, DIEA or other reagents known to one skilled in the art to provide a compound 1E.

SCHEME IV

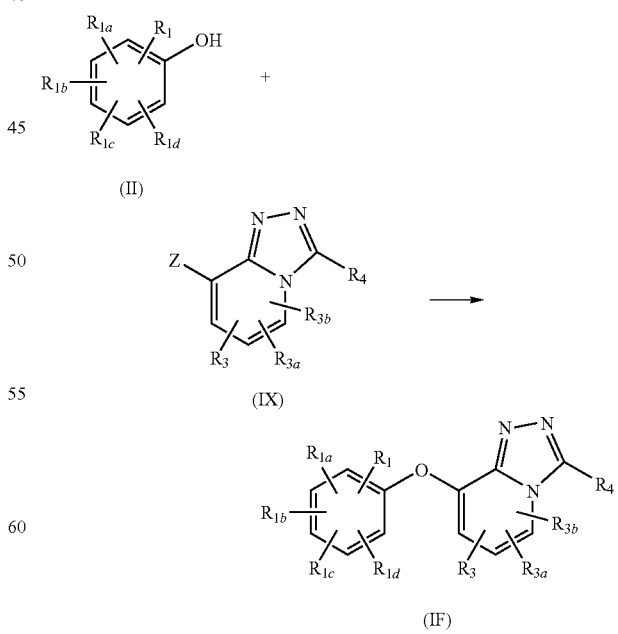

Z = Br, I, Cl or F

Scheme IV describes a method for preparing compounds of formula IF (a subset of compounds of formula I). A phenol intermediate II can be obtained commercially, prepared by methods known in the literature or by other methods known to one skilled in the art. Formation of a compound IF can be achieved from treatment of a potassium salt of a phenol II and a bromo- or iodo-substituted intermediate IX (Z is Br or I) in the presence of copper powder or salt at elevated temperature, commonly known as the Ullmann Coupling Reaction (*Tetrahedron*, 1984, 40, 1433-1456). Alternatively, a compound IF can be obtained from a $S_NAr$ reaction of a phenol II and a bromo-, chloro- or fluoro-substituted intermediate IX (Z is Br, Cl or F) in the presence of a base such as potassium hydride, sodium hydride, cesium carbonate, potassium carbonate at elevated temperature. Both Ullmann Coupling and $S_NAr$ reactions can be carried out under a conventional procedure or done in a microwave reactor.

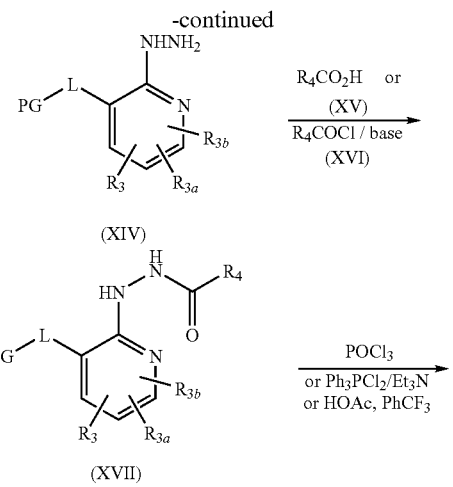

SCHEME V

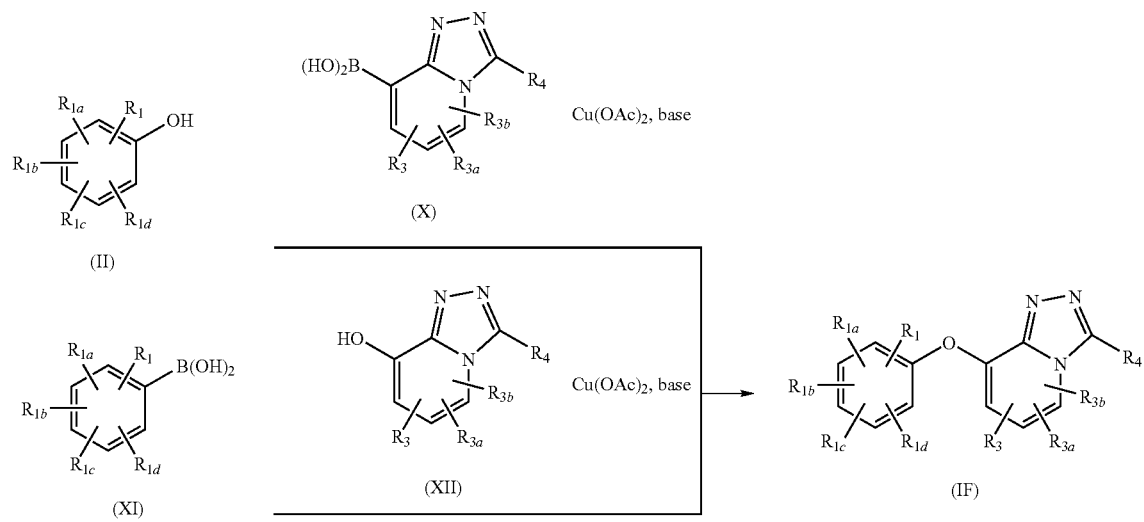

Scheme V describes an alternative method for preparing compounds of formula IF (a subset of compounds of formula I). A phenol intermediate II or arylboronic acid XI can be obtained commercially, prepared by methods known in the literature or by other methods known to one skilled in the art. Formation of a compound IF can be obtained from a copper acetate-promoted aryl ether synthesis using a phenol II and arylboronic acid X or a phenol XII and an arylboronic acid XI (*Tetrahedron Lett.*, 1998, 39, 2937-2940).

SCHEME VI

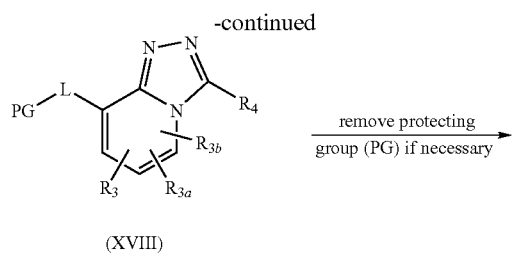

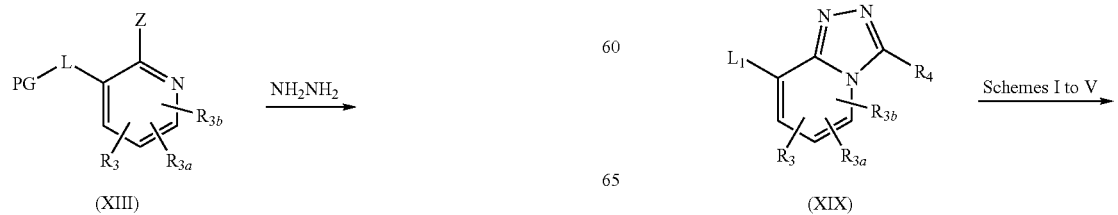

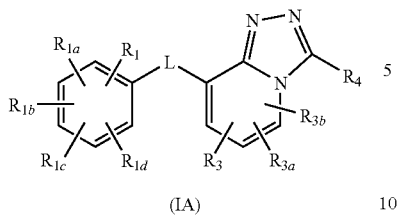

(IA)

Z = F, Cl, or Br

Scheme VI describes a method for preparing compounds of formula IA (a subset of compounds of formula I). A fluoro-, chloro- or bromopyridine intermediate XIII can be obtained commercially, prepared by methods known in the literature or by other methods known to one skilled in the art. An appropriate protecting group (PG) may be used for intermediate XIII (for example, a TBS group or ether as a protecting group for an alcohol) for better reaction compatibility. Reaction of a compound of formula XIII with hydrazine was carried out at an elevated temperature to provide an intermediate XIV. Acylation of an intermediate XIV with an acid XV using an appropriate set of amide coupling reagents such NMM/isobutylchloformate, EDAC/HOBT or other reagents described in "The Practice of Peptide Synthesis" (Spring-Verlag, 2nd Ed., Bodanszy, Miklos, 1993) provides a hydrazide intermediate XVII. Alternatively, a hydrazide XVII can be prepared from the reaction of a compound of formula XIV and an acid chloride XVI in the presence of an appropriate base such as DIEA or TEA. Formation of 1,2,4-triazolopyridine XVIII can be achieved from the reaction of XVII with POCl$_3$ at an elevated temperature. Formation of 1,2,4-triazolopyridine XVIII can also be achieved from XVII in the presence of acetic acid at an elevated temperature, either under a conventional procedure or a microwave reactor. Alternatively, formation of 1,2,4-triazolopyridine XVIII can be achieved from the reaction of XVII with Ph$_3$PCl$_2$ in the presence of a base such as TEA or by other methods known to one skilled in the art. The protecting group, if present, can be removed from a compound of formula XVIII to provide an intermediate XIX (for more protecting group examples and conditions for their removal, see 'Protective Groups in Organic Synthesis' Greene at al., John Wiley and Sons Inc., 1991). Alternatively, compounds wherein L-PG is a suitable functional group, such as Br, Cl, F, and the like, may also be converted to formula 1A via this Scheme VI. Formation of a compound of formula 1A can be achieved using reactions described in Schemes I to V or by other methods known to one skilled in the art.

SCHEME VII

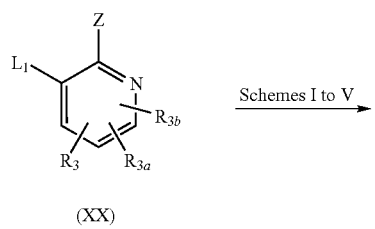

(XX)

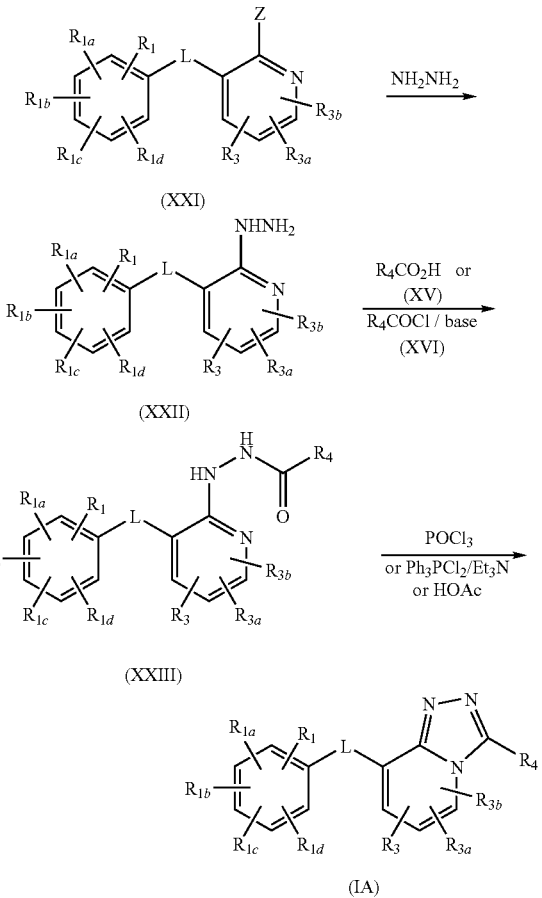

Scheme VII describes an alternative method for preparing compounds of formula IA (a subset of compounds of formula I). A fluoro-, chloro- or bromopyridine intermediate XX can be obtained commercially, prepared by methods known in the literature or by other methods known to one skilled in the art. The L$_1$ group in XX is an appropriate functional group that can form intermediate XXI through the reactions described in Schemes I to V or by other methods known to one skilled in the art. Reaction of a compound of formula XXI with hydrazine was carried out at an elevated temperature to provide an intermediate XXII. Acylation of an intermediate XXII with an acid XV using an appropriate set of amide coupling reagents such NMM/isobutylchloformate, EDAC/HOBT or other reagents described in "The Practice of Peptide Synthesis" (Spring-Verlag, 2$^{nd}$ Ed., Bodanszy, Miklos, 1993) provides a hydrazide intermediate XXIII. Alternatively, a hydrazide XXIII can be prepared from the reaction of a compound of formula XXII and an acid chloride XVI in the presence of an appropriate base such as DIEA or TEA. Formation of 1,2,4-triazolopyridine IA can be achieved from the reaction of XXIII with POCl$_3$ at an elevated temperature. Formation of 1,2,4-triazolopyridine IA can also be achieved from XXIII in the presence of acetic acid at an elevated temperature, either under a conventional procedure or a microwave reactor. Alternatively, formation of 1,2,4-triazolopyridine IA can be achieved from the reaction of XXIII with Ph$_3$PCl$_2$ in the presence of a base such as TEA or by other methods known to one skilled in the art.

SCHEME VIII

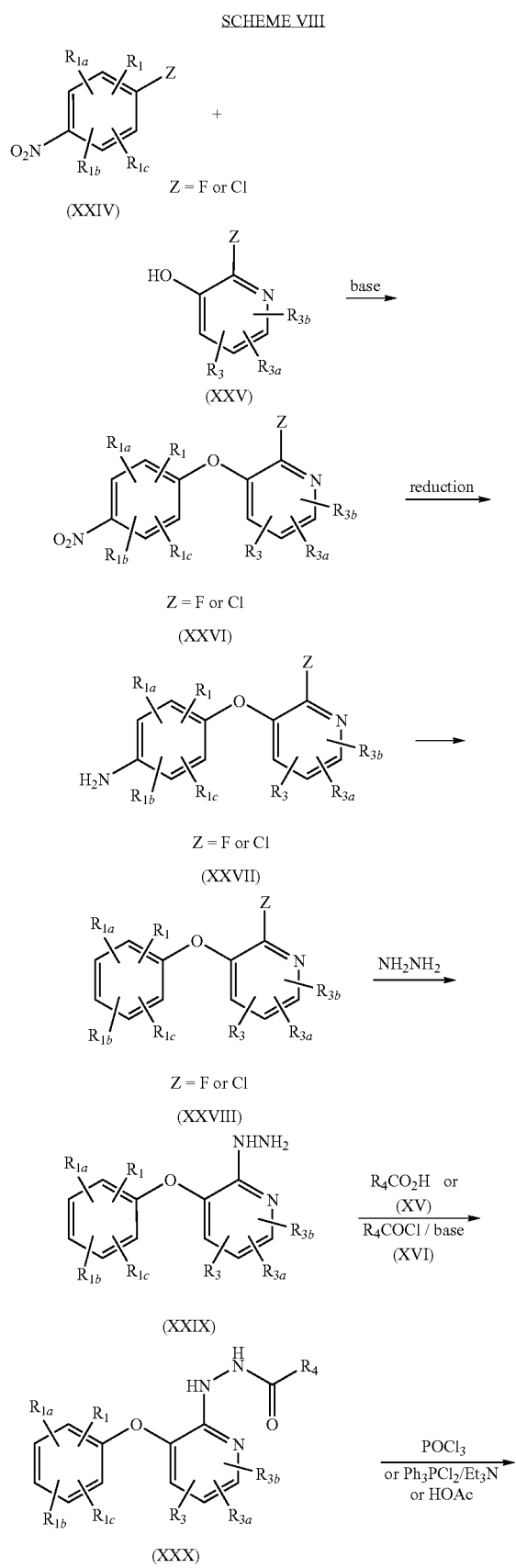

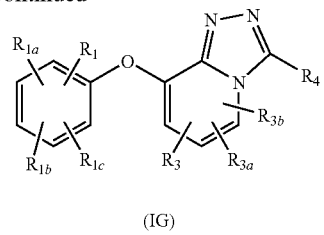

Scheme VIII describes a method for preparing compounds of formula IG (a subset of compounds of formula I). A 4-fluoro- or 4-chloronitrobenzene intermediate XXIV can be obtained commercially, prepared by methods known in the literature or by other methods known to one skilled in the art. An $S_NAr$ reaction of compound XXIV with 2-fluoro- or 2-chloro-3-hydroxylpyridine compound XXV in the presence of a base such as cesium carbonate or potassium carbonate provides compound XXVI. Reduction of nitro group in compound XXVI can be achieved under hydrogenation condition, iron powder in aqueous ethanol solution or other known methods in the literature to provide aniline intermediate XXVII. Removal of amino group in compound XXVII can be achieved from treatment of compound XXVII with concentrated hydrochloric acid and sodium nitrite followed by hypophosphorous (N. Kornblum, Org. Syn. III 1955, 295-297). Alternatively, compound XXVIII can be obtained from reaction of compound XXVII with butyl nitrite in DMF (M. Doyle, et al. J. Org. Chem. 1977, 42, 3494-3497). Reaction of 2-fluoro- or 2-chloropyridine compound XXVIII with hydrazine can be carried out at an elevated temperature to provide an intermediate XXIX. Acylation of an intermediate XXIX with an acid XV using an appropriate set of amide coupling reagents such NMM/isobutylchloformate, EDAC/HOBT or other reagents described in "The Practice of Peptide Synthesis" (Spring-Verlag, $2^{nd}$ Ed., Bodanszy, Miklos, 1993) provides a hydrazide intermediate XXX. Alternatively, a hydrazide XXX can be prepared from the reaction of a compound of formula XXIX and an acid chloride XVI in the presence of an appropriate base such as DIEA or TEA. Formation of 1,2,4-triazolopyridine IG can be achieved from the reaction of XXX with $POCl_3$ at an elevated temperature. Formation of 1,2,4-triazolopyridine IG can also be achieved from XXX in the presence of acetic acid at an elevated temperature, either under a conventional procedure or a microwave reactor. Alternatively, formation of 1,2,4-triazolopyridine IG can be achieved from the reaction of XXX with $Ph_3PCl_2$ in the presence of a base such as TEA or by other methods known to one skilled in the art.

An appropriate protecting group (PG) may be used for the compounds and/or functional groups (for example $R_1$, $R_{1a}$, $R_{1b}$, $R_{1c}$, $R_{1d}$, $R_2$, $R_{2a}$, $R_{2b}$, $R_{2c}$, $R_{2d}$, $R_3$ $R_{3a}$, $R_{3b}$, $R_4$, $R_5$, $R_6$, L and $L_1$) described in the above schemes for better reaction compatibility. The protecting group, if present, can be removed to provide the desired compound. For more protecting group examples and conditions for their removal, see "Protective Groups in Organic Synthesis", Greene at al., John Wiley and Sons Inc., 1991.

Utilities and Combinations

A. Utilities

The compounds of the present invention possess activity as inhibitors of the enzyme 11-beta-hydroxysteroid dehydrogenase type I, and, therefore, may be used in the treatment of diseases associated with 11-beta-hydroxysteroid dehydrogenase type I activity. Via the inhibition of 11-beta-hydroxysteroid dehydrogenase type I, the compounds of the present invention may preferably be employed to inhibit or modulate glucocorticoid production, thereby interrupting or modulating cortisone or cortisol production.

Accordingly, the compounds of the present invention can be administered to mammals, preferably humans, for the treatment of a variety of conditions and disorders, including, but not limited to, treating, preventing, or slowing the progression of diabetes and related conditions, microvascular complications associated with diabetes, macrovascular complications associated with diabetes, cardiovascular diseases, Metabolic Syndrome and its component conditions, inflammatory diseases and other maladies. Consequently, it is believed that the compounds of the present invention may be used in preventing, inhibiting, or treating diabetes, hyperglycemia, impaired glucose tolerance, insulin resistance, hyperinsulinemia, retinopathy, neuropathy, nephropathy, delayed wound healing, atherosclerosis and its sequelae (acute coronary syndrome, myocardial infarction, angina pectoris, peripheral vascular disease, intermittent claudication), abnormal heart function, myocardial ischemia, stroke, Metabolic Syndrome, hypertension, obesity, dyslipidemia, hyperlipidemia, hypertriglyceridemia, hypercholesterolemia, low HDL, high LDL, non-cardiac ischemia, infection, cancer, vascular restenosis, pancreatitis, neurodegenerative disease, lipid disorders, cognitive impairment and dementia, bone disease, HIV protease associated lipodystrophy, glaucoma and inflammatory diseases, such as, rheumatoid arthritis and osteoarthritis.

Metabolic Syndrome or "Syndrome X" is described in Ford, et al., *J. Am. Med. Assoc.* 2002, 287, 356-359 and Arbeeny, et al., *Curr. Med. Chem.-Imm., Endoc. & Metab. Agents* 2001, 1, 1-24.

B. Combinations

The present invention includes within its scope pharmaceutical compositions comprising, as an active ingredient, a therapeutically effective amount of at least one of the compounds of formula I, alone or in combination with a pharmaceutical carrier or diluent. Optionally, compounds of the present invention can be used alone, in combination with other compounds of the invention, or in combination with one or more other therapeutic agent(s), e.g., an antidiabetic agent or other pharmaceutically active material.

The compounds of the present invention may be employed in combination with other 11-beta-hydroxysteroid dehydrogenase type I inhibitors or one or more other suitable therapeutic agents useful in the treatment of the aforementioned disorders including: anti-diabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dislipidemic agents, anti-dylsipidemic agents, anti-hyperlipidemic agents, anti-hypertriglyceridemic agents, anti-hypercholesterolemic agents, anti-restenotic agents, anti-pancreatic agents, lipid lowering agents, appetite suppressants, memory enhancing agents, cognition promoting agents and anti-inflammatory agents.

Examples of suitable anti-diabetic agents for use in combination with the compounds of the present invention include insulin and insulin analogs: LysPro insulin, inhaled formulations comprising insulin; glucagon-like peptides; sulfonylureas and analogs: chlorpropamide, glibenclamide, tolbutamide, tolazamide, acetohexamide, glypizide, glyburide, glimepiride, repaglinide, meglitinide; biguanides: metformin, phenformin, buformin; alpha2-antagonists and imidazolines: midaglizole, isaglidole, deriglidole, idazoxan, efaroxan, fluparoxan; other insulin secretagogues: linogliride, insulinotropin, exendin-4, BTS-67582, A-4166; thiazolidinediones: ciglitazone, pioglitazone, troglitazone, rosiglitazone; PPAR-gamma agonists; PPAR-alpha agonists; PPAR alpha/gamma dual agonists; SGLT2 inhibitors; dipeptidyl peptidase-IV (DPP4) inhibitors; glucagon-like peptide-1 (GLP-1) receptor agonists; aldose reductase inhibitors; RXR agonists: JTT-501, MCC-555, MX-6054, DRF2593, GI-262570, KRP-297, LG100268; fatty acid oxidation inhibitors: clomoxir, etomoxir; α-glucosidase inhibitors: precose, acarbose, miglitol, emiglitate, voglibose, MDL-25,637, camiglibose, MDL-73,945; beta-agonists: BRL 35135, BRL 37344, Ro 16-8714, ICI D7114, CL 316,243, TAK-667, AZ40140; phosphodiesterase inhibitors, both cAMP and cGMP type: sildenafil, L686398: L-386,398; amylin antagonists: pramlintide, AC-137; lipoxygenase inhibitors: masoprocal; somatostatin analogs: BM-23014, seglitide, octreotide; glucagon antagonists: BAY 276-9955; insulin signaling agonists, insulin mimetics, PTP1B inhibitors: L-783281, TER17411, TER17529; gluconeogenesis inhibitors: GP3034; somatostatin analogs and antagonists; antilipolytic agents: nicotinic acid, acipimox, WAG 994; glucose transport stimulating agents: BM-130795; glucose synthase kinase inhibitors: lithium chloride, CT98014, CT98023; and galanin receptor agonists.

Other suitable thiazolidinediones include Mitsubishi's MCC-555 (disclosed in U.S. Pat. No. 5,594,016), Glaxo-Wellcome's GL-262570, englitazone (CP-68722, Pfizer), or darglitazone (CP-86325, Pfizer, isaglitazone (MIT/J&J), JTT-501 (JPNT/P&U), L-895645 (Merck), R-119702 (Sankyo/WL), N,N-2344 (Dr. Reddy/NN), or YM-440 (Yamanouchi).

Suitable PPAR alpha/gamma dual agonists include AR-HO39242 (Astra/Zeneca), GW-409544 (Glaxo-Wellcome), KRP297 (Kyorin Merck), as well as those disclosed by Murakami et al, "A Novel Insulin Sensitizer Acts As a Coligand for Peroxisome Proliferation—Activated Receptor Alpha (PPAR alpha) and PPAR gamma; Effect of PPAR alpha Activation on Abnormal Lipid Metabolism in Liver of Zucker Fatty Rats", Diabetes 47, 1841-1847 (1998), and WO 01/21602, the disclosure of which is incorporated herein by reference, employing dosages as set out therein, which compounds designated as preferred are preferred for use herein.

Suitable alpha2 antagonists also include those disclosed in WO 00/59506, employing dosages as set out herein.

Suitable SGLT2 inhibitors include T-1095, phlorizin, WAY-123783, and those described in WO 01/27128.

Suitable DPP4 inhibitors include saxagliptan, sitagliptan, vildagliptan, and denagliptan.

Suitable aldose reductase inhibitors include those disclosed in WO 99/26659.

Suitable meglitinides include nateglinide (Novartis) or KAD1229 (PF/Kissei).

Examples of glucagon-like peptide-1 (GLP-1) receptor agonists include Exenatide (Byetta™), NN2211 (Liraglutide, Novo Nordisk), AVE0010 (Sanofi-Aventis), R1583 (Roche/Ipsen), SUN E7001 (Daiichi/Santory), GSK-716155 (GSK/Human Genome Sciences) and Exendin-4 (PC-DAC™).

Other anti-diabetic agents that can be used in combination with compounds of the invention include ergoset and D-chiroinositol.

Suitable anti-ischemic agents include, but are not limited to, those described in the Physician's Desk Reference and NHE inhibitors, including those disclosed in WO 99/43663.

Examples of suitable lipid lowering agents for use in combination with the compounds of the present invention include one or more MTP inhibitors, HMG CoA reductase inhibitors, squalene synthetase inhibitors, fibric acid derivatives, ACAT inhibitors, lipoxygenase inhibitors, cholesterol absorption inhibitors, ileal $Na^+$/bile acid cotransporter inhibitors, upregulators of LDL receptor activity, bile acid sequestrants, cholesterol ester transfer protein inhibitors (e.g., CP-529414 (Pfizer)), and/or nicotinic acid and derivatives thereof.

MTP inhibitors which may be employed as described above include those disclosed in U.S. Pat. No. 5,595,872, U.S. Pat. No. 5,739,135, U.S. Pat. No. 5,712,279, U.S. Pat. No. 5,760,246, U.S. Pat. No. 5,827,875, U.S. Pat. No. 5,885,983, and U.S. Pat. No. 5,962,440.

The HMG CoA reductase inhibitors which may be employed in combination with one or more compounds of formula I include mevastatin and related compounds, as disclosed in U.S. Pat. No. 3,983,140, lovastatin, (mevinolin) and related compounds, as disclosed in U.S. Pat. No. 4,231,938, pravastatin, and related compounds, such as disclosed in U.S. Pat. No. 4,346,227, simvastatin, and related compounds, as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772; cerivastatin, as disclosed in U.S. Pat. Nos. 5,006,530 and 5,177,080; atorvastatin, as disclosed in U.S. Pat. Nos. 4,681,893, 5,273,995, 5,385,929 and 5,686,104; atavastatin (Nissan/Sankyo's nisvastatin (NK-104)), as disclosed in U.S. Pat. No. 5,011,930; visastatin (Shionogi-Astra/Zeneca (ZD-4522)) as disclosed in U.S. Pat. No. 5,260,440.

Preferred hypolipidemic agents are pravastatin, lovastatin, simvastatin, atorvastatin, fluvastatin, cerivastatin, atavastatin, and ZD-4522.

The fibric acid derivatives which may be employed in combination with one or more compounds of formula I include fenofibrate, gemfibrozil, clofibrate, bezafibrate, ciprofibrate, clinofibrate, and the like, probucol, and related compounds, as disclosed in U.S. Pat. No. 3,674,836, fenofibrate and gemfibrozil being preferred, bile acid sequestrants, such as cholestyramine, colestipol and DEAE-Sephadex (Secholex®, Policexide®), as well as lipostabil (Rhone-Poulenc), Eisai E-5050 (an N-substituted ethanolamine derivative), imanixil (HOE-402), tetrahydrolipstatin (THL), istigmastanylphosphorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid, acipimox, acifran, neomycin, p-aminosalicylic acid, aspirin, poly(diallylmethylamine) derivatives, such as disclosed in U.S. Pat. No. 4,759,923, quaternary amine poly(diallyldimethylammonium chloride) and ionenes, such as disclosed in U.S. Pat. No. 4,027,009, and other known serum cholesterol lowering agents.

The ACAT inhibitor which may be employed in combination with one or more compounds of formula I include those disclosed in Drugs of the Future 24, 9-15 (1999), (Avasimibe); "The ACAT inhibitor, C1-1011 is effective in the prevention and regression of aortic fatty streak area in hamsters", Nicolosi et al, Atherosclerosis (Shannon, Irel). (1998), 137(1), 77-85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1), 16-30; "RP 73163: a bioavailable alkylsulfinyl-diphenylimidazole ACAT inhibitor", Smith, C., et al, Bioorg. Med. Chem. Lett. (1996), 6(1), 47-50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173-98, Publisher: CRC, Boca Raton, Fla.; "ACAT inhibitors: potential anti-atherosclerotic agents", Sliskovic et al, Curr. Med. Chem. (1994), 1(3), 204-25; "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Stout et al, Chemtracts: Org. Chem. (1995), 8(6), 359-62, or TS-962 (Taisho Pharmaceutical Co. Ltd.).

The hypolipidemic agent may be an upregulator of LDL receptor activity, such as MD-700 (Taisho Pharmaceutical Co. Ltd) and LY295427 (Eli Lilly).

Examples of suitable cholesterol absorption inhibitors for use in combination with the compounds of the invention include ezetimibe (Zetia®).

Examples of suitable ileal $Na^+$/bile acid cotransporter inhibitors for use in combination with the compounds of the invention include compounds as disclosed in Drugs of the Future, 24, 425-430 (1999).

The lipoxygenase inhibitors which may be employed in combination with one or more compounds of formula I include 15-lipoxygenase (15-LO) inhibitors, such as benzimidazole derivatives, as disclosed in WO 97/12615, 15-LO inhibitors, as disclosed in WO 97/12613, isothiazolones, as disclosed in WO 96/38144, and 15-LO inhibitors, as disclosed by Sendobry et al "Attenuation of diet-induced atherosclerosis in rabbits with a highly selective 15-lipoxygenase inhibitor lacking significant antioxidant properties", Brit. J. Pharmacology (1997) 120, 1199-1206, and Cornicelli et al, "15-Lipoxygenase and its Inhibition: A Novel Therapeutic Target for Vascular Disease", Current Pharmaceutical Design, 1999, 5, 11-20.

Examples of suitable anti-hypertensive agents for use in combination with the compounds of the present invention include beta adrenergic blockers, calcium channel blockers (L-type and T-type; e.g. diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors (e.g., aliskiren), ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan, and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

Examples of suitable anti-obesity agents for use in combination with the compounds of the present invention include a cannabinoid receptor 1 antagonist or inverse agonist, a beta 3 adrenergic agonist, a lipase inhibitor, a serotonin (and dopamine) reuptake inhibitor, a thyroid receptor beta drug, and/or an anorectic agent.

Cannabinoid receptor 1 antagonists and inverse agonists which may be optionally employed in combination with compounds of the present invention include rimonabant, SLV 319, CP-945598 (Pfizer), SR-147778 (Sanofi-Aventis), MK0364 (Merck) and those discussed in D. L. Hertzog, Expert Opin. Ther. Patents 2004, 14, 1435-1452.

The beta 3 adrenergic agonists which may be optionally employed in combination with compounds of the present invention include AJ9677 (Takeda/Dainippon), L750355 (Merck), or CP331648 (Pfizer,) or other known beta 3 agonists, as disclosed in U.S. Pat. Nos. 5,541,204, 5,770,615, 5,491,134, 5,776,983, and 5,488,064, with AJ9677, L750, 355, and CP331648 being preferred.

Examples of lipase inhibitors which may be optionally employed in combination with compounds of the present invention include orlistat or ATL-962 (Alizyme), with orlistat being preferred.

The serotonin (and dopoamine) reuptake inhibitor and/or modulator which may be optionally employed in combination with a compound of formula I may be sibutramine, topiramate (Johnson & Johnson), APD-356 (Arena) or axokine (Regeneron), with sibutramine and APD-356 being preferred.

Examples of thyroid receptor beta compounds which may be optionally employed in combination with compounds of the present invention include thyroid receptor ligands, such as those disclosed in WO97/21993 (U. Cal SF), WO99/00353 (KaroBio), and WO00/039077 (KaroBio), with compounds of the KaroBio applications being preferred.

The anorectic agent which may be optionally employed in combination with compounds of the present invention include dexamphetamine, phentermine, phenylpropanolamine, or mazindol, with dexamphetamine being preferred.

Other compounds that can be used in combination with the compounds of the present invention include CCK receptor agonists (e.g., SR-27895B); MCHR1 antagonist (e.g., GSK 856464); galanin receptor antagonists; MCR-4 antagonists (e.g., HP-228); leptin or mimetics; urocortin mimetics, CRF antagonists, and CRF binding proteins (e.g., RU-486, urocortin).

Further, the compounds of the present invention may be used in combination with HIV protease inhibitors, including but not limited to Reyataz® and Kaletra®.

Examples of suitable memory enhancing agents, anti-dementia agents, or cognition promoting agents for use in combination with the compounds of the present invention include, but are not limited to, donepezil, rivastigmine, galantamine, memantine, tacrine, metrifonate, muscarine, xanomelline, deprenyl and physostigmine.

Examples of suitable anti-inflammatory agents for use in combination with the compounds of the present invention include, but are not limited to, prednisone, acetaminophen, aspirin, codeine, fentaynl, ibuprofen, indomethacin, ketorolac, morphine, naproxen, phenacetin, piroxicam, a steroidal analgesic, sufentanyl, sunlindac, interferon alpha, prednisolone, methylprednisolone, dexamethazone, flucatisone, betamethasone, hydrocortisone and beclomethasone.

The aforementioned patents and patent applications are incorporated herein by reference.

The above other therapeutic agents, when employed in combination with the compounds of the present invention may be used, for example, in those amounts indicated in the Physician's Desk Reference, as in the patents set out above, or as otherwise determined by one of ordinary skill in the art.

The compounds of formula I can be administered for any of the uses described herein by any suitable means, for example, orally, such as in the form of tablets, capsules, granules or powders; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents.

In carrying out the method of the invention for treating diabetes and related diseases, a pharmaceutical composition will be employed containing the compounds of formula I, with or without other antidiabetic agent(s) and/or antihyperlipidemic agent(s) and/or other type therapeutic agents in association with a pharmaceutical vehicle or diluent. The pharmaceutical composition can be formulated employing conventional solid or liquid vehicles or diluents and pharmaceutical additives of a type appropriate to the mode of desired administration, such as pharmaceutically acceptable carriers, excipients, binders, and the like. The compounds can be administered to a mammalian patient, including humans, monkeys, dogs, etc. by an oral route, for example, in the form of tablets, capsules, beads, granules or powders. The dose for adults is preferably between 1 and 2,000 mg per day, which can be administered in a single dose or in the form of individual doses from 1-4 times per day.

A typical capsule for oral administration contains compounds of structure I (250 mg), lactose (75 mg), and magnesium stearate (15 mg). The mixture is passed through a 60 mesh sieve and packed into a No. 1 gelatin capsule.

A typical injectable preparation is produced by aseptically placing 250 mg of compounds of structure I into a vial, aseptically freeze-drying and sealing. For use, the contents of the vial are mixed with 2 mL of physiological saline, to produce an injectable preparation.

Assay(s) for 11-Beta-Hydroxysteroid Dehydrogenase Activity

The in vitro inhibition of recombinant human 11beta-HSD1 was determined as follows.

Recombinant human 11beta-HSD1 was expressed stably in HEK 293 EBNA cells. Cells were grown in DMEM (high glucose) containing MEM non-essential amino acids, L-glutamine, hygromycine B (200 ug/ml), and G418 (200 ug/ml). The cell pellets were homogenized, and the microsomal fraction was obtained by differential centrifugation. 11beta-HSD1 over expressed microsomes were used as the enzyme source for the Scintillation Proximity Assay (SPA). The test compounds at the desired concentration were incubated at room temperature with 12.5 µg of microsomal enzyme, 250 nM [$^3$H]-cortisone, 500 µM NADPH, 50 mM MES, pH 6.5, and 5 mM EDTA in 96-well OptiPlates. The reaction was terminated with the addition of 1 mM 18β-glycerrhentic acid. SPA reagent mixture (YSi anti-rabbit IgG, anti-cortisol antibody in 50 mM Tris, pH 8.0 containing 1% CHAPS and 1% glycerol) was added and the reaction was further incubated at room temperature over night and counted in TopCount. The $IC_{50}$ (concentration of compound required for 50% inhibition of cortisol formation) was determined using XLfit.

In general, preferred compounds of the present invention, such as particular compounds disclosed in the following examples, have been identified to inhibit the catalytic activity of 11-beta-hydroxysteroid dehydrogenase type I at concentrations equivalent to, or more potently than, 10 μM, preferably 5 μM, more preferably 3 μM, thereby demonstrating compounds of the present invention as especially effective inhibitors of 11-beta-hydroxysteroid dehydrogenase type I. Potencies can be calculated and expressed as either inhibition constants (Ki values) or as IC50 (inhibitory concentration 50%) values, and refer to activity measured employing the assay system described above.

EXAMPLES

The following working Examples serve to better illustrate, but not limit, some of the preferred embodiments of the present invention.

General

The term HPLC refers to a Shimadzu high performance liquid chromatography with one of following methods:
Method A: YMC or Phenomenex C18 5 micron 4.6×50 mm column using a 4 minute gradient of 0-100% solvent B [90% MeOH:10% $H_2O$:0.2% $H_3PO_4$] and 100-0% solvent A [10% MeOH:90% $H_2O$:0.2% $H_3PO_4$] with 4 mL/min flow rate and a 1 min. hold, an ultra violet (UV) detector set at 220 nm.
Method B: Phenomenex S5 ODS 4.6×30 mm column, gradient elution 0-100% B/A over 2 min (solvent A=10% MeOH/$H_2O$ containing 0.1% TFA, solvent B=90% MeOH/$H_2O$ containing 0.1% TFA), flow rate 5 mL/min, UV detection at 220 nm.
Method C: YMC S7 ODS 3.0×50 mm column, gradient elution 0-100% B/A over 2 min (solvent A=10% MeOH/$H_2O$ containing 0.1% TFA, solvent B=90% MeOH/$H_2O$ containing 0.1% TFA), flow rate 5 mL/min, UV detection at 220 nm.
The term prep HPLC refers to an automated Shimadzu HPLC system using a mixture of solvent A (10% MeOH/90% $H_2O$/0.2% TFA) and solvent B (90% MeOH/10% $H_2O$/0.2% TFA). The preparative columns were packed with YMC or Phenomenex ODS C18 5 micron resin or equivalent.

Abbreviations

The following abbreviations are employed in the Examples and elsewhere herein:
Ph=phenyl
Bn=benzyl
i-Bu=iso-butyl
Me=methyl
Et=ethyl
Pr=propyl
Bu=butyl
AIBN=2,2'-Azobisisobutyronitrile
Boc or BOC=tert-butoxycarbonyl
Cbz=carbobenzyloxy or carbobenzoxy or benzyloxycarbonyl
DCM=dichloromethane
DEAD=Diethyl azodicarboxylate
DIAD=Diisopropyl azodicarboxylate
DIEA=N,N-diisopropylethylamine
DMA=N,N-dimethylacetylamide
DMF=N,N-dimethylformamide
DMSO=dimethylsulfoxide
EtOAc=ethyl acetate
EDAC=3-ethyl-3'-(dimethylamino)propyl-carbodiimide hydrochloride (or 1-[(3-(dimethyl)amino)propyl])-3-ethylcarbodiimide hydrochloride)
FMOC=fluorenylmethoxycarbonyl
HOAc or AcOH=acetic acid
HOAT=1-hydroxy-7-azabenzotriazole
HOBT=1-hydroxybenzotriazole
LAH=lithium aluminum hydride
mCPBA=3-Chloroperoxybenzoic acid
NMM=N-methyl morpholine
NBS=N-Bromosuccinimide
n-BuLi=n-butyllithium
Oxone®=Monopersulfate
Pd/C=palladium on carbon
$PtO_2$=platinum oxide
PyBOP reagent=benzotriazol-1-yloxy-tripyrrolidino phosphonium hexafluorophosphate
$SOCl_2$=Thionyl chloride
TBAF=tetrabutylammonium fluoride
TBS=tert-Butyldimethylsilyl
TMS=trimethylsilyl
TEA=triethylamine
TFA=trifluoroacetic acid
THF=tetrahydrofuran
equiv=equivalent(s)
min=minute(s)
h or hr=hour(s)
L=liter
mL=milliliter
μL=microliter
g=gram(s)
mg=milligram(s)
mol=mole(s)
mmol=millimole(s)
meq=milliequivalent
RT=room temperature
sat or sat'd=saturated
aq.=aqueous
TLC=thin layer chromatography
HPLC=high performance liquid chromatography
HPLC $R_t$=HPLC retention time
LC/MS=high performance liquid chromatography/mass spectrometry
MS or Mass Spec=mass spectrometry
NMR=nuclear magnetic resonance
mp=melting point Example 1

3-Cycloheptyl-8-((2,6-dichlorophenoxy)methyl)-1,2,4-itriazolo[4,3-a]pyridine

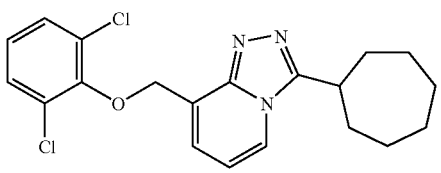

Compound 1A. 1-(3-((tert-Butyldimethylsilyloxy)methyl)pyridin-2-yl)hydrazine

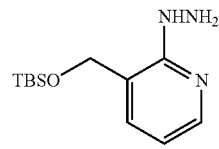

To a solution of (2-chloropyridin-3-yl)methanol (3.4 g, 23.7 mmol) in 50 mL of dichloromethane was added imidazole (2.4 g, 35.3 mmol) and tert-butyldimethylsilyl chloride (4.3 g, 28.5 mmol) at RT. The mixture was stirred at RT for 60 min, and then diluted with 100 mL of hexanes. The white solid was filtered off, and the filtrate was concentrated under reduced pressure. Additional solid was removed by triturating with 5% ethyl acetate in hexanes to provide a pale yellow oil. The pale yellow oil was dissolved in 40 mL of dioxane and then hydrazine (7.5 mL, 238.7 mmol) was added. The resulting mixture was heated to reflux for 36 h. After this time, the mixture was cooled to RT, and the solvent was removed in vacuo to provide a residue. The residue was diluted with ethyl acetate, washed with water, dried over $Na_2SO_4$ and concentrated under reduced pressure to give the title compound (4.7 g, 78%) as a brown oil. HPLC $R_t$ (Method A): 2.42 min. LC/MS (m/z)=254 (M+H)+.

Compound 1B. N'-(3-((tert-Butyldimethylsilyloxy)methyl)pyridin-2-yl)cycloheptane-carbohydrazide

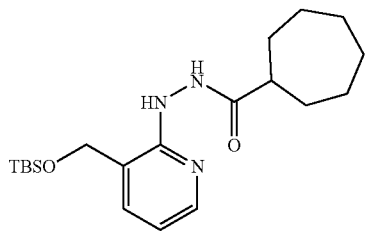

To a solution of cycloheptanecarboxylic acid (2.69 g, 18.9 mmol) in 20 mL of anhydrous THF was added NMM (2.8 mL, 25.2 mmol) followed by iso-butyl chloroformate (2.5 mL, 18.9 mmol) at 0° C. under nitrogen. The reaction was stirred at 0° C. for 30 min. A solution of compound 1A (1.6 g, 6.3 mmol) in 15 mL of THF was added, and the stirring was continued at 0° C. to RT for 3 hr. The reaction was quenched with water, and the solvent was removed in vacuo to provide a residue. The residue was diluted with ethyl acetate, washed with water, dried over $Na_2SO_4$ and concentrated to provide crude material. The crude material was purified via silica gel chromatography (10-30% ethyl acetate in hexanes) to provide the title compound (810 mg, 34%) as an oil. HPLC $R_t$ (Method A): 3.30 min. LC/MS (m/z)=378 (M+H)+.

Compound 1C. 8-((tert-Butyldimethylsilyloxy)methyl)-3-cycloheptyl-[1,2,4]triazolo[4,3-a]pyridine

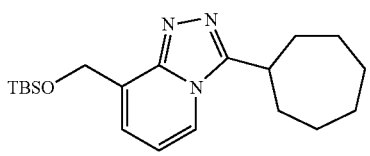

To a solution of compound 1B (810 mg, 2.15 mmol) in 15 mL of anhydrous THF was added DIEA (3 mL, 17.2 mmol) at −78° C. The reaction mixture was stirred for 15 min. Dichlorotriphenylphosphorane (2.15 g, 6.45 mmol) was then added at −78° C. under nitrogen, and the reaction mixture was stirred at RT overnight to provide a solid. The solid was filtered off, washed with THF, and the combined filtrate was concentrated in vacuo to provide a residue. The residue was diluted with ethyl acetate, washed with water, dried over $Na_2SO_4$ and concentrated to provide crude material. The crude material was purified via silica gel chromatography (10-30% ethyl acetate in hexanes) to provide the title compound (601 mg, 78%) as a yellow oil. HPLC $R_t$ (Method A): 4.05 min. LC/MS (m/z)=360 (M+H)+.

Compound 1D. (3-Cycloheptyl-[1,2,4]triazolo[4,3-a]pyridin-8-yl)methanol

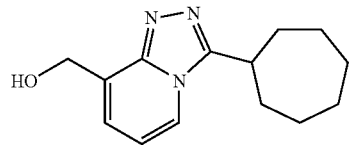

To a solution of compound 1C (601 mg, 1.67 mmol) in 5 mL of anhydrous THF was added a solution of TBAF (3.4 mL, 3.4 mmol, 1 M in THF) at RT. The reaction mixture was stirred at RT for 1 hr. After this time, the solvent was removed. The resulting residue was diluted with ethyl acetate, washed with water, dried over $Na_2SO_4$ and concentrated to provide crude material. The crude material was purified via silica gel chromatography (5-10% methanol in ethyl acetate) to provide the title compound (389 mg, 95%) as a white flake. HPLC $R_t$ (Method A): 1.80 min. LC/MS (m/z)=246 (M+H)+.

Example 1

To a solution of compound 1D (30 mg, 0.12 mmol) in 5 mL of anhydrous THF was added 2,6-dichlorophenol (30 mg, 0.18 mmol), triphenylphosphine (48 mg, 0.18 mmol) and DIAD (37 mg, 0.18 mmol) at RT. The reaction mixture was stirred at RT for 1 hr, and then concentrated in vacuo to provide a residue. The residue was diluted with ethyl acetate, washed with water, dried over $Na_2SO_4$ and concentrated to provide crude product. The crude product was purified via silica gel chromatography (20-30% ethyl acetate in hexanes) to provide Example 1 as a white solid (42 mg, 89%). HPLC $R_t$ (Method A): 3.69 min. LC/MS (m/z)=390 (M+H)+. $^1$H NMR: δ 7.79 (dd, J=1, 7 Hz, 1H), 7.60 (dd, J=1, 7 Hz, 1H), 7.27 (d, J=8 Hz, 2H), 6.96-7.00 (m, 1H), 6.84 (t, J=7 Hz, 1H), 5.47 (s, 2H), 3.16-3.29 (m, 1H), 1.92-2.12 (m, 4H), 1.76-1.82 (m, 2H), 1.51-1.70 (m, 6H).

Example 2

3-Cycloheptyl-8-((2,6-dichlorophenylthio)methyl)-[1,2,4]triazolo[4,3-a]-pyridine

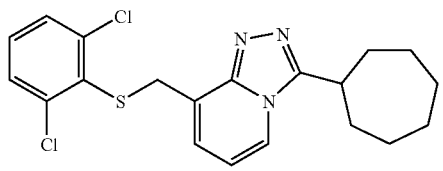

A solution of compound 1D (140 mg, 0.57 mmol) in 15 mL of dichloromethane was treated with $SOCl_2$ (0.166 mL, 2.28 mmol) at RT. The reaction mixture was stirred for 2 h at RT. After this time, the solvent was evaporated under reduced pressure to provide a white powder. The white powder was suspended in 20 mL of dichloromethane, treated with DIEA (0.478 mL, 2.85 mmol) followed by 2,6-dichlorobenzenethiol (0.206 g, 1.15 mmol) at RT, and then stirred for 2 h at RT. The resulting mixture was concentrated and purified via silica gel chromatography (20-50% ethyl acetate in hexanes) to provide Example 2 as a colorless oil (212 mg, 91%). HPLC $R_t$ (Method A): 3.44 min. LC/MS (m/z)=406 (M+H)$^+$. $^1$H NMR: δ 7.69 (d, J=7 Hz, 1H), 7.25 (d, J=8 Hz, 2H), 7.08 (t, J=8 Hz, 1H), 6.65 (d, J=7 Hz, 1H), 6.53 (t, J=7 Hz, 1H), 4.40 (s, 2H), 3.12-3.24 (m, 1H), 1.92-2.10 (m, 4H), 1.72-1.89 (m, 2H), 1.48-1.72 (m, 6H).

Example 3

3-Cycloheptyl-8-((2,6-dichlorophenylsulfonyl)methyl)-[1,2,4]triazolo[4,3-a]-pyridine

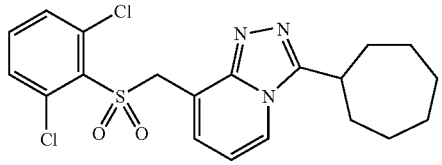

A solution of Example 2 (110 mg, 0.271 mmol) in 20 mL of dichloromethane was treated with mCPBA (390 mg, 1.35 mmol) at RT for 4 h. After this time, the reaction mixture was analyzed by LCMS, which indicated the presence of sulfoxide. Additional mCPBA (156 mg, 0.542 mmol) was added. Upon completion of addition, the reaction mixture was stirred for an additional 2 h. At the conclusion of this period, the reaction mixture was diluted with dichloromethane, washed with 1 N NaOH, brine and water, dried over MgSO$_4$, and concentrated to provide crude product. The crude product was purified via silica gel chromatography (50% ethyl acetate in hexanes) to provide Example 3 as a light-brown, thick oil (57.5 mg, 48%). HPLC $R_t$ (Method A): 2.99 min. LC/MS (m/z)=438 (M+H)$^+$. $^1$H NMR: δ 7.78 (dd, J=1, 7 Hz, 1H), 7.39 (dd, J=1, 7 Hz, 1H), 7.19-7.29 (m, 3H), 6.78 (t, J=7 Hz, 1H), 5.08 (s, 2H), 3.07-3.17 (m, 1H), 1.92-2.02 (m, 4H), 1.72-1.82 (m, 2H), 1.42-1.72 (m, 6H).

Example 4

8-((2,6-Dichlorobenzyloxy)methyl)-3-cycloheptyl-[1,2,4]triazolo[4,3-a]-pyridine

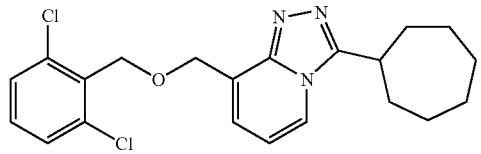

To a solution of compound 1D (50 mg, 0.204 mmol) in 1 mL of DMF was added sodium hydride (8.2 mg, 0.204 mmol, 60% in mineral oil) at RT. After stirring for 15 min at RT, the reaction mixture was cooled to 0° C. and 2,6-dichlorobenzyl bromide (49 mg, 0.204 mmol) was added. Upon completion of addition, the reaction mixture was stirred at 0° C. to RT for 1.5 h, quenched with water, and then extracted with ethyl acetate to provide crude product. The crude product was purified via silica gel chromatography (30-50% ethyl acetate in hexanes) to provide Example 4 as a yellow oil (46 mg, 56%). HPLC $R_t$ (Method A): 3.53 min. LC/MS (m/z)=404 (M+H)$^+$. $^1$H NMR: δ 7.81 (dd, J=1, 7 Hz, 1H), 7.39 (dd, J=1, 7 Hz, 1H), 7.35-7.37 (m, 2H), 7.25-7.21 (m, 1H), 6.83 (t, J=7 Hz, 1H), 5.14 (s, 2H), 5.02 (s, 2H), 3.20-3.35 (m, 1H), 2.01-2.21 (m, 4H), 1.84-2.00 (m, 2H), 1.58-1.82 (m, 6H).

Example 5

3-Chloro-N-((3-cycloheptyl-[1,2,4]triazolo[4,3-a]pyridin-8-yl)methyl)-2-methylbenzenesulfonamide

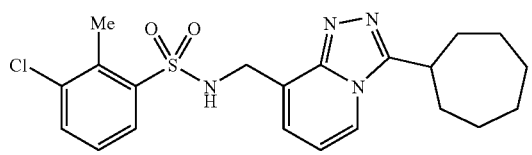

Compound 5A. (3-Cycloheptyl-[1,2,4]triazolo[4,3-a]pyridin-8-yl)methanamine

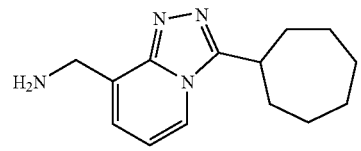

To a solution of compound 1D (150 mg, 0.611 mmol) in 10 mL of dichloromethane was added DIEA (0.425 mL, 3.055 mmol) and methanesulfonyl chloride (140 mg, 1.22 mmol) at 0° C. The reaction mixture was stirred at 0° C. to RT for 2 h. After this time, the reaction mixture was diluted with dichloromethane, washed with brine and water, dried over MgSO$_4$, and concentrated under reduced pressure to provide a residue. The residue was dissolved in 5 mL of DMF, and then sodium azide (60 mg, 0.817 mmol) was added. The resulting mixture was heated at 50° C. for 1 h. After this time, the reaction mixture was diluted with ethyl acetate, washed with brine and water, dried over MgSO$_4$, filtered and concentrated to provide the azido intermediate. The azido intermediate was dissolved in 15 mL of THF and 3 mL of water. Polymer-bonded PPh$_3$ (3 mmol/g, 500 mg, 1.53 mmol) was added and the resulting mixture was heated at 50° C. for 1 h. The resulting solid was filtered off and the solvent was removed from the filtere to provide the title compound (120 mg, 80%) as a yellow oil. HPLC $R_t$ (Method A): 1.58 min. LC/MS (m/z)=245 (M+H)$^+$.

Example 5

To a solution of compound 5A (35 mg, 0.143 mmol) in 3 mL of dichloromethane was added TEA (0.1 mL, 0.715 mmol) and 3-chloro-2-methylbenzene-1-sulfonyl chloride (96.8 mg, 0.430 mmol) at RT. The reaction mixture was stirred for 2 h at RT. At the conclusion of this period, the reaction mixture was concentrated, diluted with ethyl acetate, washed with 1 N NaOH, brine and water, dried over MgSO$_4$ and concentrated to provide crude product. The crude product was purified via silica gel chromatography using 20-100% ethyl acetate in hexanes to provide Example 5 as a lightyellow powder (21.4 mg, 35%). HPLC R$_t$ (Method A): 3.31 min. LC/MS (m/z)=433 (M+H)$^+$. $^1$H NMR: δ 7.82 (d, J=8 Hz, 1H), 7.71 (d, J=7 Hz, 1H), 7.38 (d, J=8 Hz, 1H), 7.10 (t, J=8 Hz, 1H), 6.93 (d, J=7 Hz, 1H), 6.51-6.72 (m, 2H), 4.54 (d, J=6 Hz, 2H), 3.1-3.3 (m, 1H), 2.52 (s, 3H), 1.52-2.22 (m, 12H).

Example 6

3-(Azepan-1-yl)-8-((2,6-dichlorophenoxy)methyl)-[1,2,4]triazolo[4,3-a]-pyridine

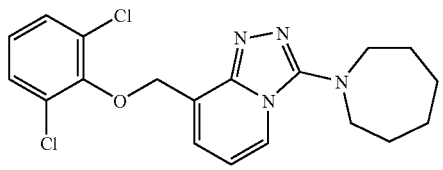

Compound 6A. Azepane-1-carbonyl chloride

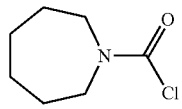

To a solution of azepane (2 g, 20.2 mmol) in 30 mL of anhydrous toluene was added DIEA (3.5 mL, 20.0 mmol) and pyridine (1.63 mL, 20.2 mmol). The mixture was cooled to −10° C. under nitrogen. Once at the prescribed temperature, carbon dioxide gas was bubbled through the solution for 30 min, and then a solution of thionyl chloride (1.74 mL, 24.0 mmol) in 10 mL of toluene was added at −10° C. Upon completion of addition, the reaction mixture was stirred for 1 hr while the temperature was kept under 10° C. The reaction mixture was then diluted with ethyl acetate, washed with cold 0.5 N HCl solution and brine, dried over Na$_2$SO$_4$, and concentrated to give the title compound (2.76 g, 85%) as a pale yellow oil.

Compound 6B. N'-(3-((tert-Butyldimethylsilyloxy)methyl)pyridin-2-yl)azepane-1-carbohydrazide

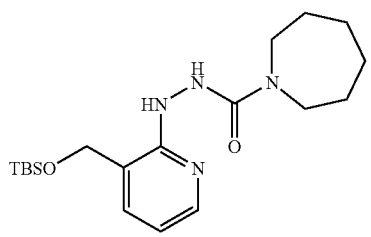

To a solution of compound 1A (1.7 g, 6.7 mmol) in 10 mL of dichloromethane was added DIEA (2.33 mL, 13.4 mmol) and compound 6A (1.3 g, 8.0 mmol) at RT. The reaction mixture was heated at 45° C. for 6 hr, cooled to RT and quenched with water. After the dichloromethane was removed by rotavapor, the reaction mixture was diluted with ethyl acetate, washed with water, dried over Na$_2$SO$_4$ and concentrated to provide a residue. The residue was triturated in ethyl acetate and hexanes to give the title (2.1 g, 83%) as a white solid. HPLC R$_t$ (Method A): 2.98 min. LC/MS (m/z)= 379 (M+H)$^+$.

Compound 6C. 3-(Azepan-1-yl)-8-(chloromethyl)-[1,2,4]triazolo[4,3-a]pyridine

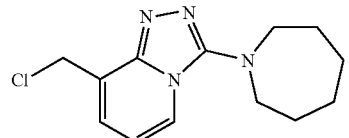

To a solution of compound 6B (1.5 g, 4.0 mmol) in 10 mL of anhydrous toluene was added POCl$_3$ (0.73 mL, 8.0 mmol) at RT. The reaction mixture was heated at 70° C. for 2 hr, cooled to RT and then quenched with water. The reaction mixture was diluted with ethyl acetate, washed with water, dried over Na$_2$SO$_4$ and concentrated to provide crude material. The crude material was purified via silica gel chromatography (50-100% ethyl acetate in hexanes) to provide the title compound (307 mg, 29%) as a pale yellow solid. HPLC R$_t$ (Method A): 1.98 min. LC/MS (m/z)=265 (M+H)$^+$.

Example 6

To a solution of 2,6-dichlorophenol (107 mg, 0.66 mmol) in 3 mL of anhydrous acetone was added potassium carbonate (114 mg, 0.82 mmol) and compound 6C (145 mg, 0.55 mmol) at RT. Upon completion of addition, the reaction mixture was heated at 60° C. for 2 hr, cooled to RT and then quenched with water. The acetone was removed in vacuo, and the reaction mixture was diluted with ethyl acetate, washed with water, dried over Na$_2$SO$_4$ and concentrated to provide crude product. The crude product was purified via silica gel chromatography (50% ethyl acetate in hexanes) to provide Example 6 as a white solid (185 mg, 86%). HPLC R$_t$ (Method A): 3.35 min. LC/MS (m/z)=391 (M+H)$^+$. $^1$H NMR: δ 7.77 (dd, J=1, 7 Hz, 1H), 7.60 (dd, J=1, 7 Hz, 1H), 7.31 (d, J=8 Hz, 2H), 7.03 (t, J=8 Hz, 1H), 6.81 (t, J=7 Hz, 1H), 5.47 (s, 2H), 3.49 (t, J=6 Hz, 4H), 1.83-1.91 (m, 4H), 1.71-1.78 (m, 4H).

Example 7

8-(3-Chloro-2-methylphenoxy)-3-cycloheptyl-[1,2,4]triazolo[4,3-a]pyridine

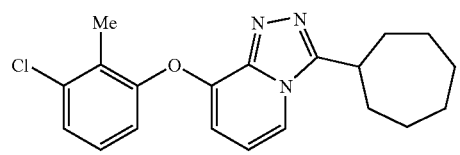

Compound 7A.
3-(3-Chloro-2-methylphenoxy)-2-fluoropyridine

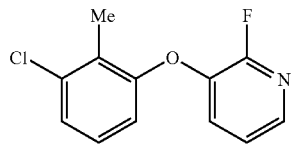

3-Chloro-2-methylphenylboronic acid (2 g, 11.74 mmol), 2-fluoro-3-hydroxy pyridine (663 mg, 5.87 mmol), copper acetate (1.1 g, 5.87 mmol), pyridine (2.4 mL, 29.35 mmol), and fresh activated 4A molecular sieves (7 g) were combined in 100 mL of dichloromethane in a round bottle flask equipped with a drying tube (connected to air). The reaction mixture was stirred at RT overnight. At the conclusion of this period, the solid was filtered off, and the filtrate was concentrated under reduced pressure to provide crude material. The crude material was purified via silica gel chromatography (5-10% ethyl acetate in hexanes) to provide compound 7A (1.08 g, 77%) as a white powder. HPLC $R_t$: 3.61 min, LC/MS (m/z)=238 (M+H)$^+$.

Compound 7B. 1-(3-(3-Chloro-2-methylphenoxy)pyridin-2-yl)hydrazine

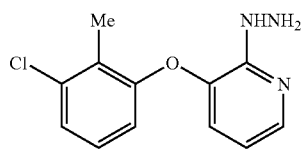

To a solution of compound 7A (500 mg, 2.1 mmol) in 15 mL of dioxane was added anhydrous hydrazine (0.529 mL, 16.8 mmol). The reaction mixture was heated at 100° C. for 3 h. After this time, the reaction mixture was analyzed by LC/MS, which showed that the reaction was not complete. Additional hydrazine (0.529 mL, 16.8 mmol) was added, and the reaction mixture was heated at 100° C. overnight. At the conclusion of this period, the solvent was concentrated under reduced pressure to provide compound 7B (700 mg, 100%) as a white solid. HPLC $R_t$: 1.89 min, LC/MS (m/z)=250 (M+H)$^+$.

Compound 7C. N'-(3-(3-Chloro-2-methylphenoxy)pyridin-2-yl)cycloheptane carbohydrazide

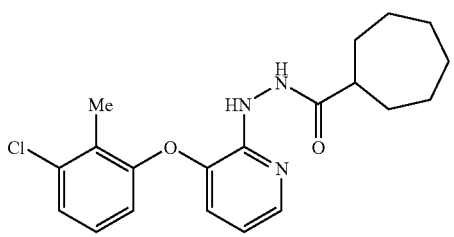

To a solution of cycloheptyl carboxylic acid (896 mg, 6.3 mmol) in 40 mL of anhydrous THF were added NMM (0.693 mL, 6.3 mmol) and isobutyl chloroformate (0.83 mL, 6.3 mmol) at 0° C. The reaction mixture was stirred at 0° C. for 30 min, and the resulting suspension was poured into a solution of compound 7B (524 mg, 2.1 mmol) in 20 mL of THF at 0° C. The resulting mixture was stirred at 0° C. for 1 h, and the resulting solid was filtered off. The filtrate was concentrated under reduced pressure to provide crude material. The crude material was purified via silica gel chromatography (5-20% ethyl acetate in hexanes) to provide the title compound (800 mg, 92%) as a white powder. HPLC $R_t$ (Method A): 2.98 min. LC/MS (m/z)=374 (M+H)$^+$.

Example 7

To a solution of compound 7C (700 mg, 1.87 mmol) in 20 mL of anhydrous THF was added DIEA (2.6 mL, 15 mmol) at −78° C. The reaction mixture was stirred at −78° C. for 30 min and then dichlorotriphenylphosphorane (2.06 g, 6.18 mmol) was added. The resulting mixture was stirred at −78° C. to RT overnight. After this time, the resulting white solid was filtered off, and the filtrate was concentrated under reduced pressure to provide crude product. Purification by silica gel chromatography (0-30% ethyl acetate in hexanes) provided Example 7 as a white powder (630 mg, 94%). HPLC $R_t$ (Method A): 3.63 min. LC/MS (m/z)=356 (M+H)$^+$. $^1$H NMR: δ 7.64 (d, J=7 Hz, 1H), 7.22 (d, J=8 Hz, 1H), 7.11 (t, J=8 Hz, 1H), 6.95 (d, J=8 Hz, 1H), 6.63 (t, J=7 Hz, 1H), 6.09 (d, J=7 Hz, 1H), 3.13-3.30 (m, 1H), 1.42-2.33 (m, 12H).

Example 8

8-(3-Chloro-2-methylphenoxy)-3-(4-methoxybicyclo[2.2.2]octan-1-yl)-[1,2,4]triazolo[4,3-a]pyridine

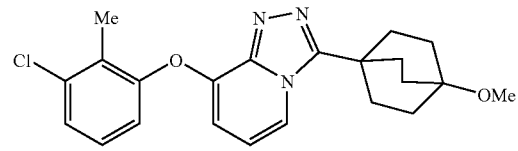

Compound 8A. N'-(3-(3-Chloro-2-methylphenoxy)pyridin-2-yl)-4-methoxybicyclo[2.2.2]octane-1-carbohydrazide

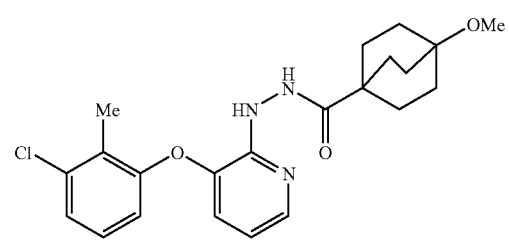

To a stirred solution of 4-methoxybicyclo[2.2.2]octane-1-carboxylic acid (590 mg, 3.2 mmol; see Adcock and Abeywickrema, *J. Org. Chem.* 1982, 47, 2951-2957) in 8 mL of anhydrous THF were added NMM (0.423 mL, 3.8 mmol) and isobutyl chloroformate (0.50 mL, 3.8 mmol) at 0° C. The reaction was stirred at 0° C. for 30 min, then compound 7B (800 mg, 3.2 mmol) was added at 0° C. The resulting mixture was stirred at 0° C. for 10 min followed by 90 min at RT before quenched with water. The reaction mixture was concentrated under reduced pressure. The residue was dissolved in ethyl acetate, washed with water, dried over Na$_2$SO$_4$ and concentrated. Purification by silica gel chromatography (30-60% ethyl acetate in hexanes) provided compound 8A as pale-yellow foam solid (840 mg, 63%). HPLC R$_t$ (Method A): 2.56 min. LC/MS (m/z)=415 (M+H)$^+$.

Example 8

To a suspension of compound 8A (420 mg, 1.0 mmol) in 5 mL of anhydrous toluene was added POCl$_3$ (0.275 mL, 3.0 mmol) at RT. The resulting solution was heated at 110° C. for 3 hr, cooled to room temperature, then quenched with water. After pH was adjusted to basic with NaOH, the mixture was extracted with ethyl acetate. The combined extracts were dried over Na$_2$SO$_4$ and concentrated. Purification by silica gel chromatography (20-50% ethyl acetate in hexanes) provided Example 8 as a white solid (250 mg, 63%). HPLC R$_t$ (Method A): 3.32 min. LC/MS (m/z)=398 (M+H)$^+$. $^1$H NMR (CDCl$_3$): δ 7.89 (d, J=7.0 Hz, 1H), 7.29 (d, J=8.3 Hz, 1H), 7.16 (t, J=7.9 Hz, 1H), 7.01 (d, J=7.5 Hz, 1H), 6.58 (t, J=7.5 Hz, 1H), 6.12 (d, J=7.5 Hz, 1H), 3.23 (s, 3H), 2.31 (t, J=8.0 Hz, 6H), 2.27 (s, 3H), 1.86 (t, J=8.0 Hz, 6H).

Examples 9 and 10

4-(8-(3-Chloro-2-methylphenoxy)-[1,2,4]triazolo[4,3-a]pyridin-3-yl)bicyclo[2.2.2]octan-1-ol and 4-(8-(3-Chloro-2-methylphenoxy)-[1,2,4]triazolo[4,3-a]pyridin-3-yl)bicyclo[2.2.2]octan-1-yl acetate, respectively

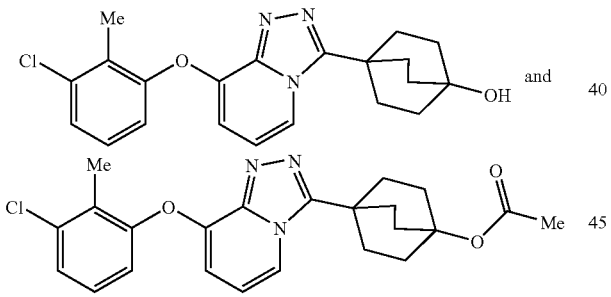

To a suspension of Example 8 (290 mg, 0.73 mmol) in anhydrous acetic anhydride (1 mL, 10.6 mmol) was slowly added 48% HBr aqueous solution (0.7 mL, 6.2 mmol). The reaction was heated at 100° C. for 20 hr, and cooled to RT. It was diluted with ethyl acetate, washed with 1N NaOH solution, dried over Na$_2$SO$_4$ and concentrated. Purification by PrepHPLC gave Example 9 (220 mg, 61%) and Example 10 (9 mg, 3%), both as TFA salt. Example 9: HPLC R$_t$ (Method A): 3.07 min. LC/MS (m/z)=384 (M+H)$^+$. $^1$H NMR (CDCl$_3$): δ 7.97 (d, J=7.0 Hz, 1H), 7.31 (d, J=8.3 Hz, 1H), 7.18 (t, J=8.3 Hz, 1H), 7.02 (d, J=8.3 Hz, 1H), 6.76 (t, J=7.2 Hz, 1H), 6.30 (d, J=7.5 Hz, 1H), 2.32 (t, J=7.9 Hz, 6H), 2.25 (s, 3H), 1.88 (t, J=7.9 Hz, 6H). Example 10: HPLC R$_t$ (Method A): 3.57 min. LC/MS (m/z)=426 (M+H)$^+$. $^1$H NMR (CDCl$_3$): δ 8.16 (d, J=7.0 Hz, 1H), 7.33 (d, J=7.9 Hz, 1H), 7.19 (t, J=7.9 Hz, 1H), 7.03 (d, J=8.4 Hz, 1H), 6.87 (t, J=7.0 Hz, 1H), 6.42 (d, J=7.5 Hz, 1H), 2.29-2.35 (m, 6H), 2.24 (s, 3H), 2.18-2.22 (m, 6H), 2.00 (s, 3H).

Example 11

4-(8-(2-Chloro-5-methylphenoxy)-[1,2,4]triazolo[4,3-a]pyridin-3-yl)bicyclo[2.2.1]heptan-1-ol

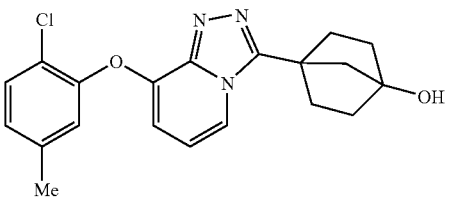

Compound 11A. 3-Bromo-2-hydrazinylpyridine

To a solution of 2-chloro-3-bromopyridine (14.5 g, 75.1 mmol) in 100 mL of dioxane was added anhydrous hydrazine (35.4 mL, 1127 mmol) at RT. The reaction mixture was heated at reflux for 15 h, then cooled to RT. After most of the solvent were removed under reduced pressure, the residue was diluted with ethyl acetate, washed with water, dried over Na$_2$SO$_4$, and concentrated. Recrystallization in ethyl acetate and hexanes gave compound 11A (12.9 g, 91%) as a solid. LC/MS (m/z)=188 (M+H)$^+$.

Compound 11B. N'-(3-Bromopyridin-2-yl)-4-methoxybicyclo[2.2.1]heptane-1-carbohydrazide

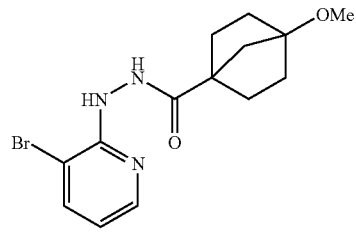

To a stirred solution of 4-methoxybicyclo[2.2.1]heptane-1-carboxylic acid (4.7 g, 27.6 mmol; see Adcock, Abeywickrema and Kok, *J. Org. Chem.* 1984, 49, 1387-1397) in 90 mL of anhydrous THF were added NMM (3.6 mL, 32.7 mmol) and isobutyl chloroformate (4.3 mL, 32.7 mmol) at 0° C. The reaction was stirred at 0° C. for 30 min, then compound 11A (5.2 g, 27.7 mmol) was added at 0° C. The resulting mixture was stirred at 0° C. for 30 min followed by 5 hr at RT before quenched with water. The reaction mixture was concentrated under reduced pressure. The residue was dissolved in ethyl acetate, washed with water, dried over Na$_2$SO$_4$ and concentrated. Purification by silica gel chromatography (10-50% ethyl acetate in hexanes) provided compound 11B as pale-yellow foam solid (7.0 g, 75%). HPLC R$_t$ (Method A): 1.25 min. LC/MS (m/z)=340 (M+H)$^+$.

Compound 11C. 8-Bromo-3-(4-methoxybicyclo[2.2.1]heptan-1-yl)-[1,2,4]triazolo[4,3-a]pyridine

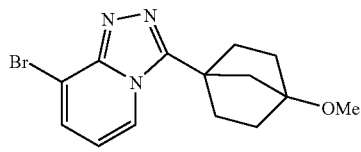

To compound 11B (700 mg, 2.1 mmol) in 14 mL of anhydrous α,α,α-trifluorotoluene was added glacial acetatic acid (3 mL, 52.5 mmol) at RT. The reaction was carried out in a microwave reactor (Emrys Optimizer, Personal Chemistry, Biotage) at 200° C. for 30 min. A total of 7 g of compound 11B were repeated in 10 runs. The reaction mixtures were combined and concentrated under reduced pressure. The residue was dissolved in ethyl acetate, washed with 1N NaOH, water, dried over $Na_2SO_4$ and contracted. Purification by silica gel chromatography (20-80% ethyl acetate in hexanes) provided compound 11C as white solid (5.7 g, 86%). HPLC $R_t$ (Method A): 2.07 min. LC/MS (m/z)=323 (M+H)$^+$.

Compound 11D. 4-(8-Bromo-[1,2,4]triazolo[4,3-a]pyridin-3-yl)bicyclo[2.2.1]heptan-1-ol

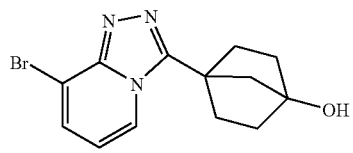

Compound 11C (500.0 mg, 1.55 mmol) was slowly dissolved in 48% HBr aqueous solution (8 mL, 70.7 mmol), followed by addition of acetic anhydride (3.4 mL, 36 mmol). The reaction was heated at 120° C. for 14 h, cooled to RT, and concentrated under reduced pressure. It was diluted with ethyl acetate, washed with 1N NaOH, water, dried over $Na_2SO_4$ and concentrated. Purification by silica gel chromatography (100% ethyl acetate to 5% methanol in ethyl acetate) provided compound 11D (445 mg, 93%) as white solid. HPLC $R_t$ (Method A): 1.59 min. LC/MS (m/z)=308 (M+H).

Example 11

To a solution of compound 11D (30 mg, 0.097 mmol) in anhydrous DMF (0.5 mL) were added 2-chloro-5-methylphenol (69 mg, 0.49 mmol) and anhydrous $Cs_2CO_3$ powder (159 mg, 0.49 mmol). The reaction was carried out in a microwave reactor (Emrys Optimizer, Personal Chemistry, Biotage) at 180° C. for 3.4 hr. Additional 2-chloro-5-methylphenol (69 mg, 0.49 mmol) and anhydrous $Cs_2CO_3$ powder (159 mg, 0.49 mmol) were added, and the reaction was run at 180° C. for another 3 hr. The reaction mixture was diluted with ethyl acetate, washed with 1N NaOH, water, dried over $MgSO_4$ and concentrated. Purification by PrepHPLC provided example 11 as white solid (31 mg, 66%) as TFA salt. HPLC $R_t$ (Method A): 2.90 min. LC/MS (m/z)=370 (M+H)$^+$. $^1$H NMR (CDCl$_3$): δ7.84 (d, J=7.2 Hz, 1H), 7.36 (d, J=7.7 Hz, 1H), 7.06 (s, 1H), 7.05 (d, J=8.8 Hz, 1H), 6.75 (t, J=7.2 Hz, 1H), 6.30 (d, J=7.2 Hz, 1H), 2.28-2.40 (m, 2H), 2.33 (s, 3H), 2.23 (s, 2H), 2.12-2.22 (m, 2H), 1.86-2.03 (m, 4H).

Examples 12 to 183

Examples 12 to 183 in Table 1 were synthesized according to the procedures described in Examples 1 to 11, the schemes, or by other similar methods known to one skilled in the art, with other appropriate reagents.

TABLE 1

| Example | Structure | LC/MS Mass (M + H) | HPLC purity (%) |
|---|---|---|---|
| 12 | 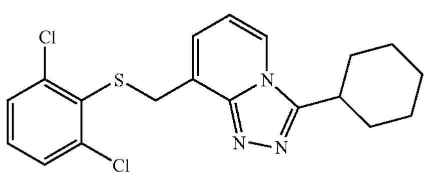 | 392 | 96 |
| 13 | 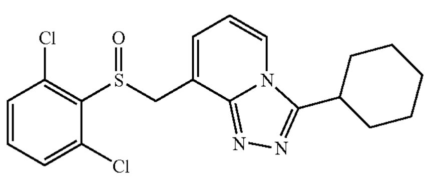 | 408 | 65 |
| 14 | 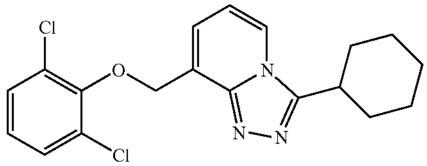 | 376 | 98 |

TABLE 1-continued

| Example | Structure | LC/MS Mass (M + H) | HPLC purity (%) |
|---|---|---|---|
| 15 | 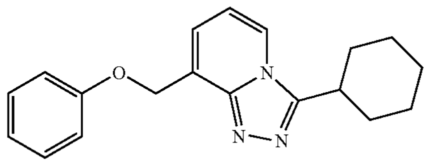 | 308 | 98 |
| 16 | 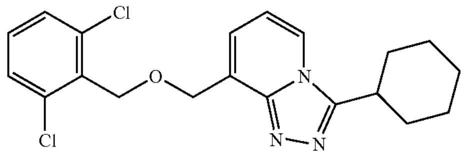 | 390 | 98 |
| 17 | 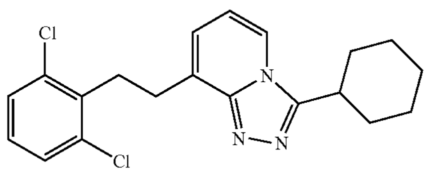 | 374 | 98 |
| 18 | 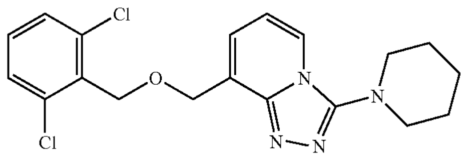 | 391 | 98 |
| 19 | 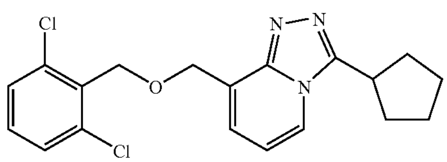 | 376 | 98 |
| 20 | 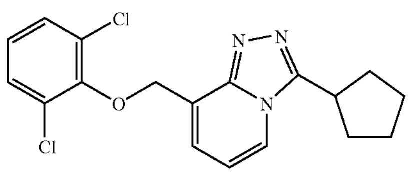 | 362 | 95 |
| 21 | 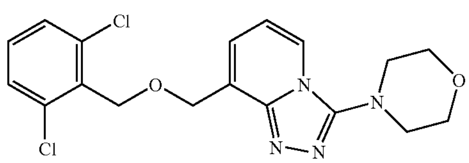 | 393 | 98 |
| 22 | 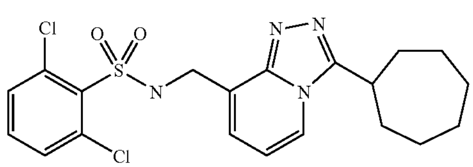 | 453 | 95 |
| 23 | 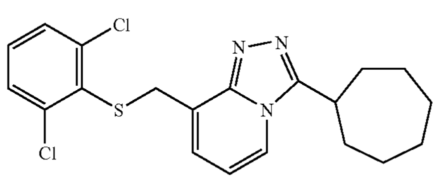 | 406 | 97 |

TABLE 1-continued

| Example | Structure | LC/MS Mass (M + H) | HPLC purity (%) |
|---|---|---|---|
| 24 | 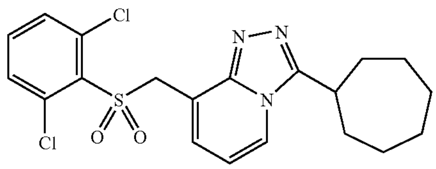 | 438 | 95 |
| 25 | 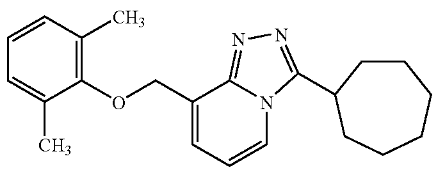 | 350 | 95 |
| 26 | 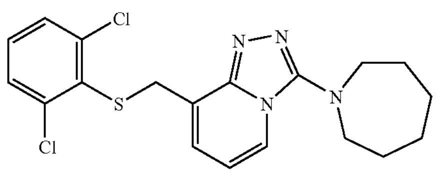 | 407 | 98 |
| 27 | 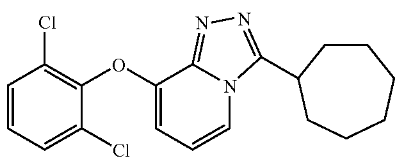 | 376 | 98 |
| 28 | 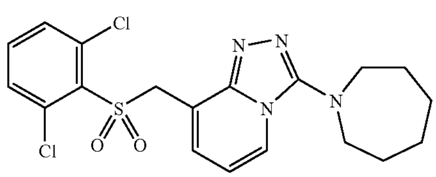 | 439 | 97 |
| 29 | 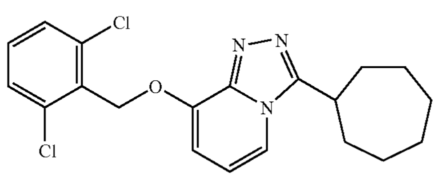 | 390 | 95 |
| 30 | 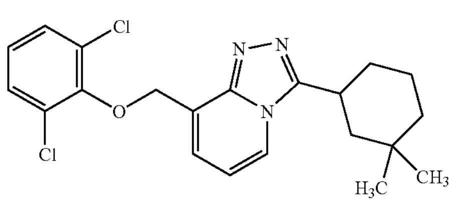 | 404 | 97 |
| 31 | 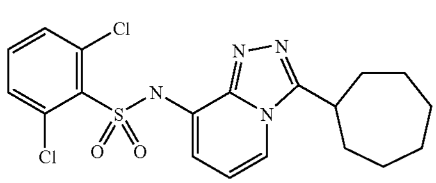 | 439 | 95 |

TABLE 1-continued

| Example | Structure | LC/MS Mass (M + H) | HPLC purity (%) |
|---|---|---|---|
| 32 | 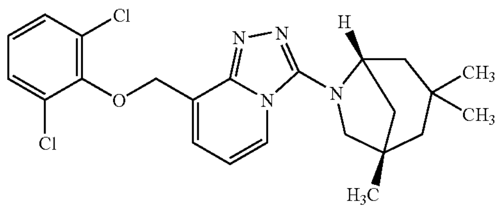 | 445 | 98 |
| 33 | 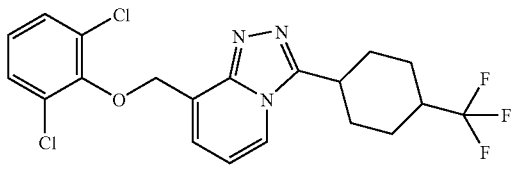 | 444 | 95 |
| 34 | 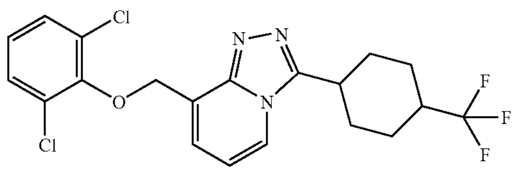 | 444 | 98 |
| 35 | 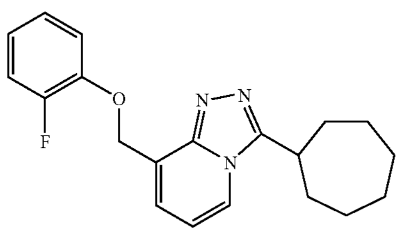 | 340 | 84.9 |
| 36 | 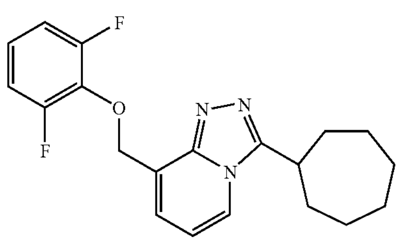 | 358 | 95.9 |
| 37 | 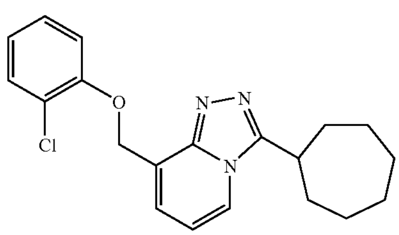 | 356 | 87.0 |
| 38 | 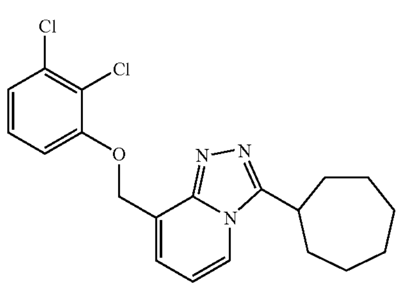 | 390 | 98.1 |

TABLE 1-continued

| Example | Structure | LC/MS Mass (M + H) | HPLC purity (%) |
| --- | --- | --- | --- |
| 39 | 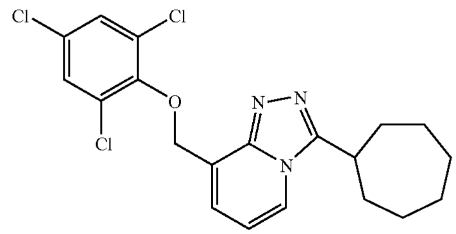 | 424 | 100.0 |
| 40 | 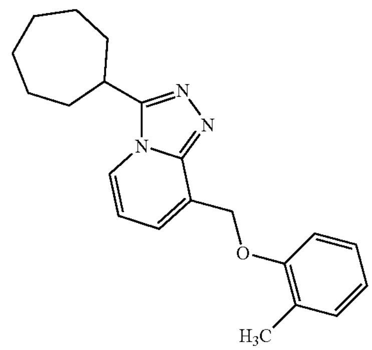 | 336 | 100.0 |
| 41 | 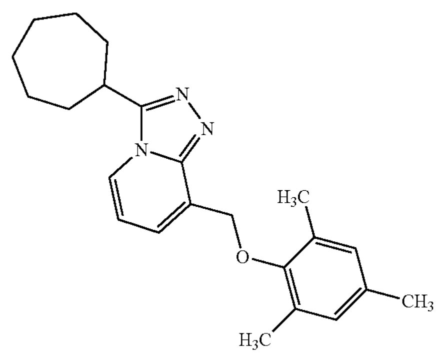 | 364 | 100.0 |
| 42 | 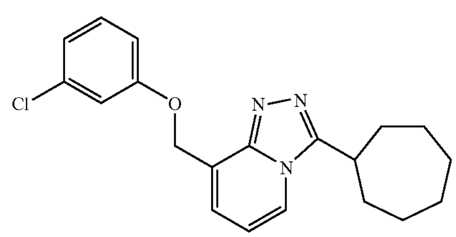 | 356 | 97.6 |
| 43 | 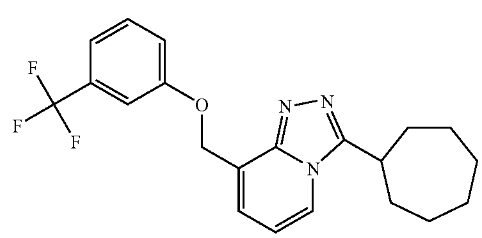 | 390 | 100.0 |

TABLE 1-continued

| Example | Structure | LC/MS Mass (M + H) | HPLC purity (%) |
|---|---|---|---|
| 44 | 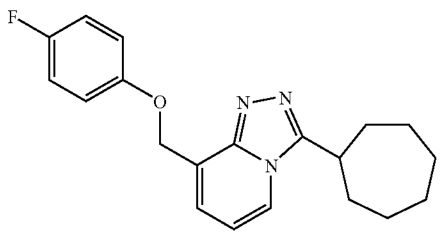 | 340 | 87.9 |
| 45 | 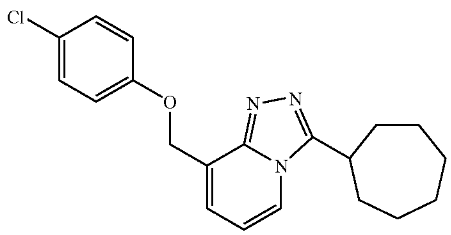 | 356 | 94.4 |
| 46 | 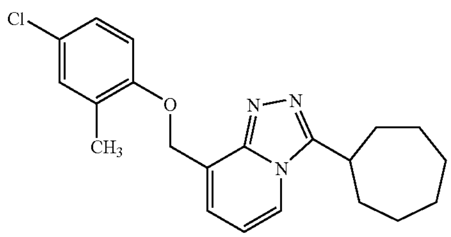 | 370 | 89.1 |
| 47 | 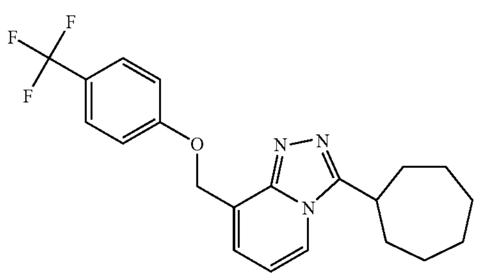 | 390 | 100.0 |
| 48 | 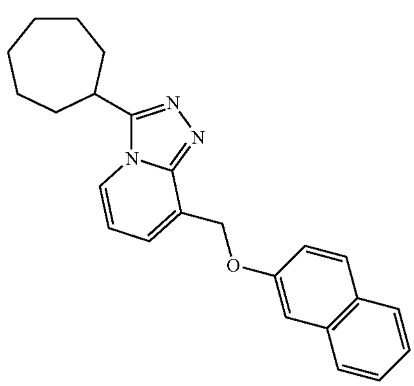 | 372 | 80.5 |

TABLE 1-continued

| Example | Structure | LC/MS Mass (M + H) | HPLC purity (%) |
|---------|-----------|--------------------|-----------------|
| 49 | 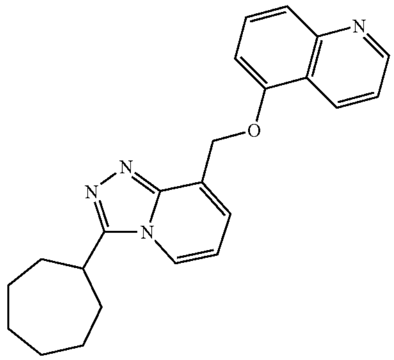 | 373 | 82.3 |
| 50 | 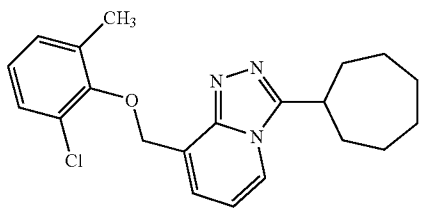 | 370 | 100.0 |
| 51 | 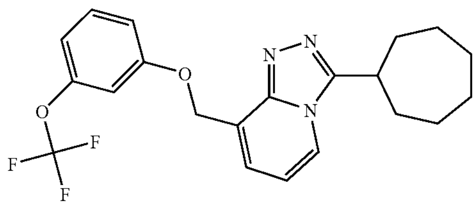 | 406 | 100.0 |
| 52 | 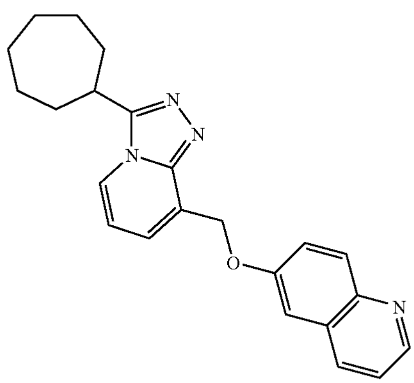 | 373 | 89.5 |
| 53 | 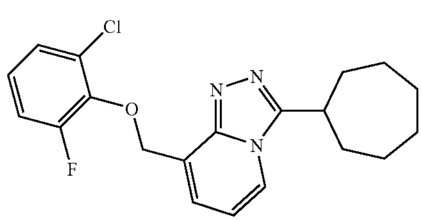 | 374 | 100.0 |
| 54 | 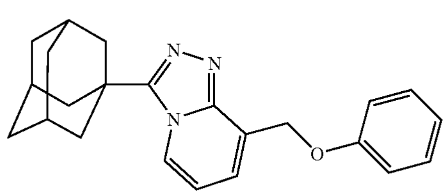 | 360 | 89.0 |

TABLE 1-continued
| Example | Structure | LC/MS Mass (M + H) | HPLC purity (%) |
| --- | --- | --- | --- |
| 55 | 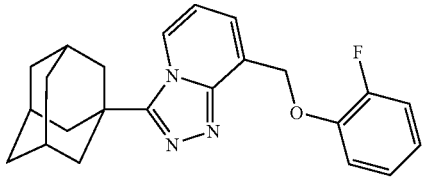 | 378 | 97.8 |
| 56 | 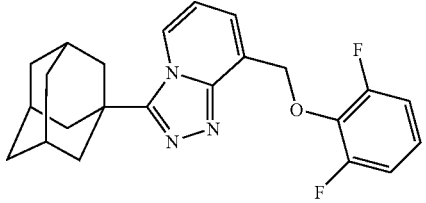 | 396 | 100.0 |
| 57 | 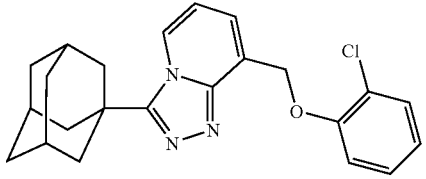 | 394 | 100.0 |
| 58 | 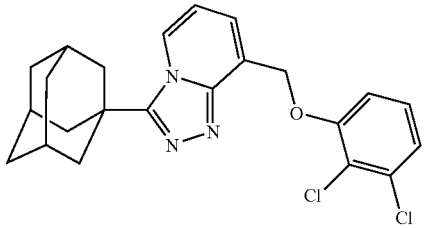 | 428 | 100.0 |
| 59 | 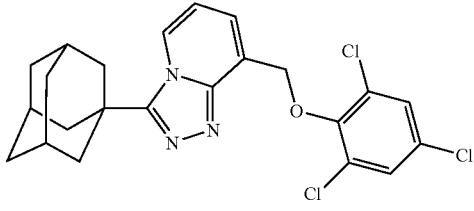 | 462 | 100.0 |
| 60 | 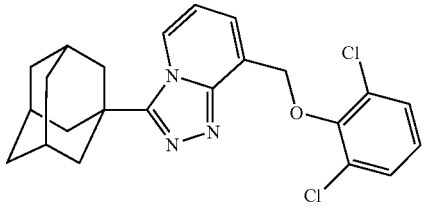 | 428 | 96.7 |
| 61 | 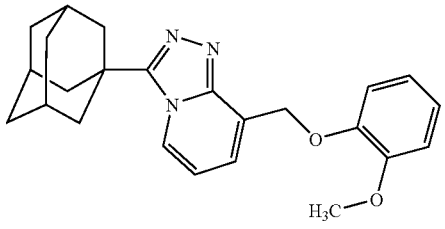 | 390 | 100.0 |

TABLE 1-continued
| Example | Structure | LC/MS Mass (M + H) | HPLC purity (%) |
|---|---|---|---|
| 62 | 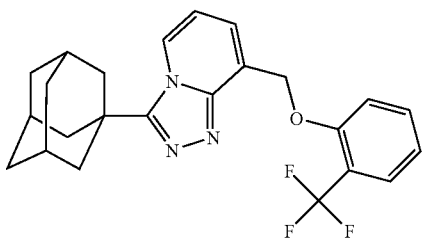 | 428 | 96.4 |
| 63 | 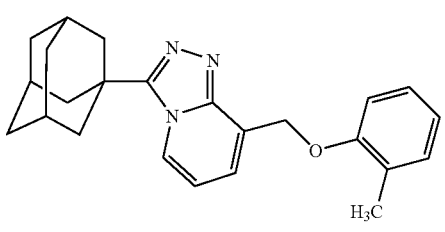 | 374 | 100.0 |
| 64 | 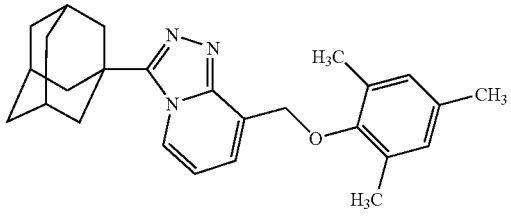 | 402 | 100.0 |
| 65 | 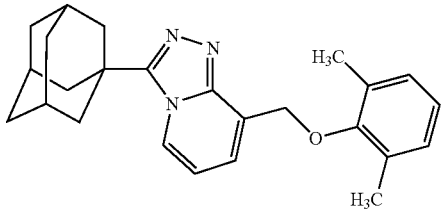 | 388 | 100.0 |
| 66 | 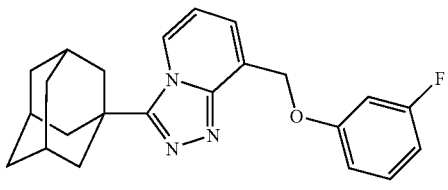 | 378 | 97.2 |
| 67 | 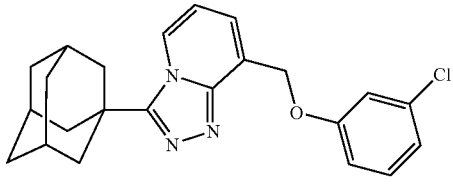 | 394 | 100.0 |
| 68 | 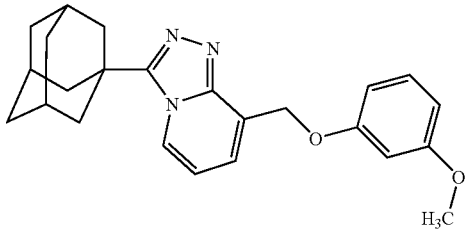 | 390 | 100.0 |

TABLE 1-continued

| Example | Structure | LC/MS Mass (M + H) | HPLC purity (%) |
|---------|-----------|--------------------|-----------------|
| 69 | 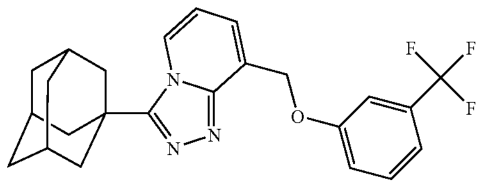 | 428 | 100.0 |
| 70 | 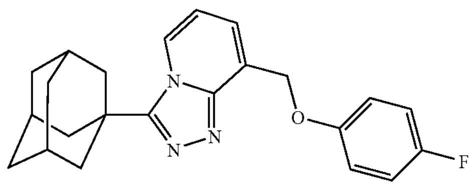 | 378 | 100.0 |
| 71 | 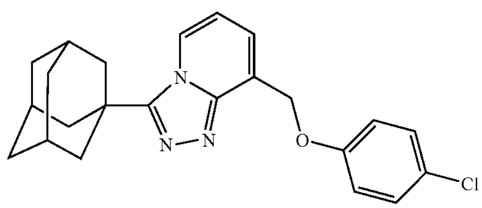 | 394 | 100.0 |
| 72 | 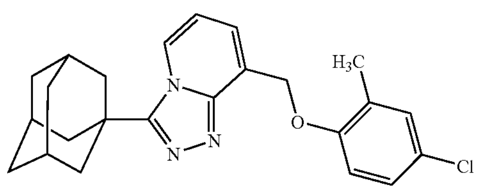 | 408 | 97.4 |
| 73 | 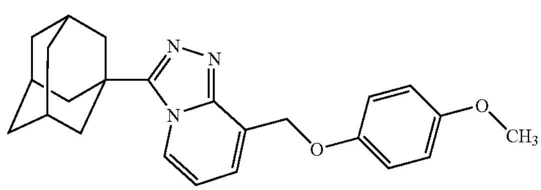 | 390 | 100.0 |
| 74 | 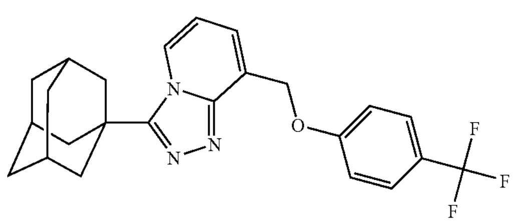 | 428 | 100.0 |
| 75 | 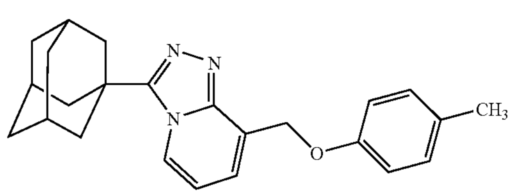 | 374 | 100.0 |

TABLE 1-continued

| Example | Structure | LC/MS Mass (M + H) | HPLC purity (%) |
|---|---|---|---|
| 76 | 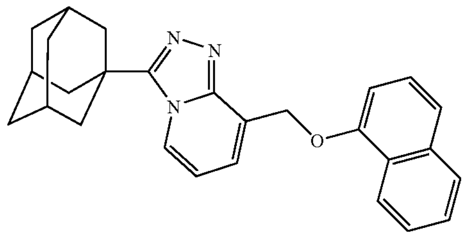 | 410 | 100.0 |
| 77 | 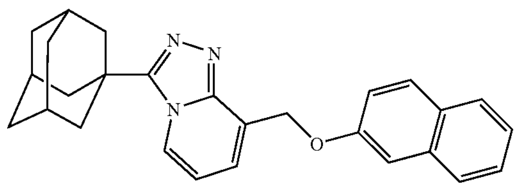 | 410 | 93.7 |
| 78 | 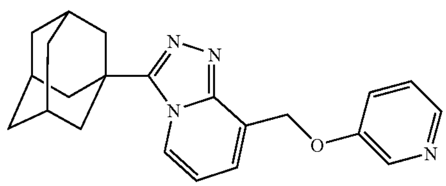 | 361 | 93.2 |
| 79 | 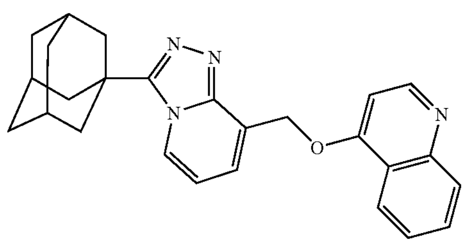 | 412 | 100.0 |
| 80 | 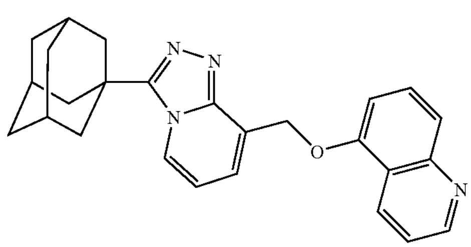 | 412 | 100.0 |
| 81 | 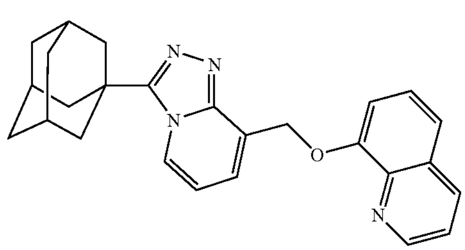 | 412 | 100.0 |

TABLE 1-continued

| Example | Structure | LC/MS Mass (M + H) | HPLC purity (%) |
|---|---|---|---|
| 82 | 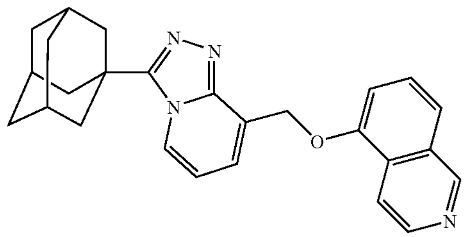 | 412 | 100.0 |
| 83 | 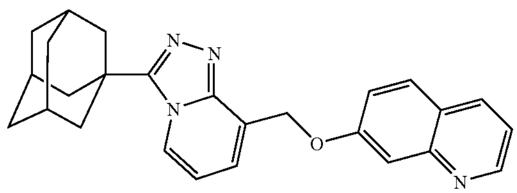 | 412 | 100.0 |
| 84 | 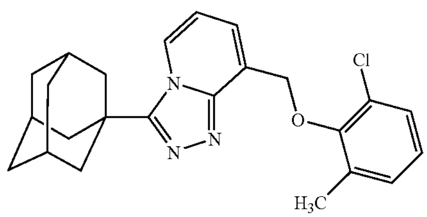 | 408 | 100.0 |
| 85 | 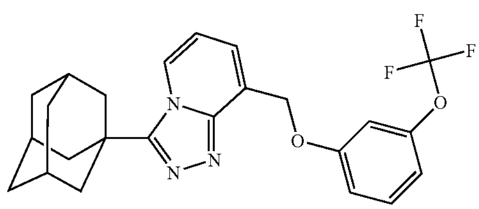 | 444 | 100.0 |
| 86 | 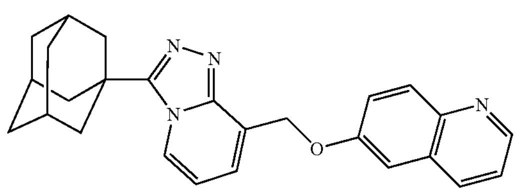 | 411 | 100.0 |
| 87 | 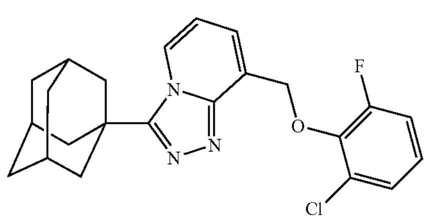 | 412 | 100.0 |
| 88 | 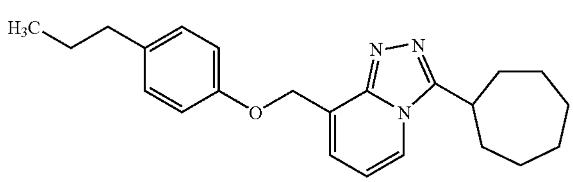 | 364 | 98 |

TABLE 1-continued

| Example | Structure | LC/MS Mass (M + H) | HPLC purity (%) |
|---|---|---|---|
| 89 | 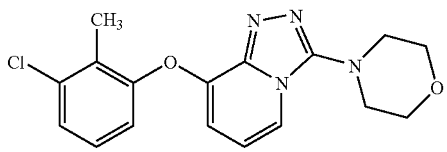 | 345 | 96 |
| 90 | 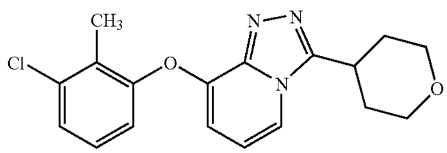 | 344 | 96 |
| 91 | 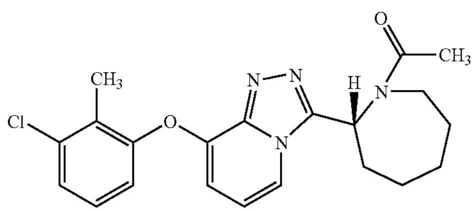 | 399 | 97 |
| 92 | 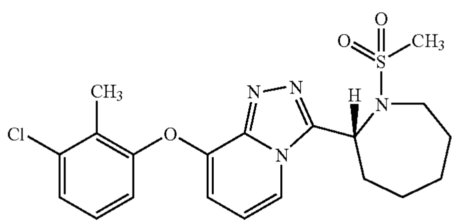 | 435 | 97 |
| 93 | 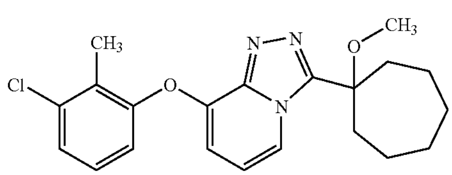 | 386 | 98 |
| 94 | 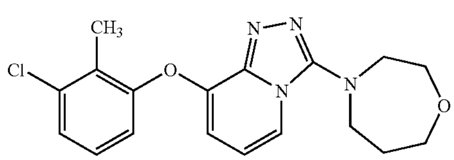 | 359 | 96 |
| 95 | 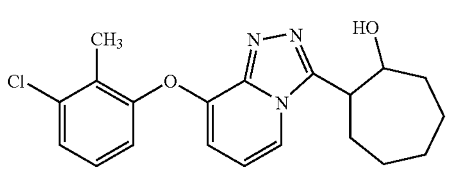 | 372 | 95 |
| 96 | 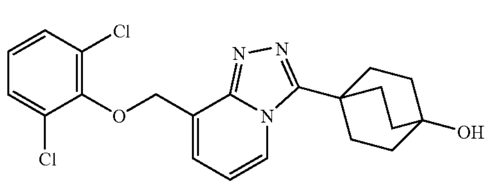 | 418 | 98 |

TABLE 1-continued

| Example | Structure | LC/MS Mass (M + H) | HPLC purity (%) |
|---|---|---|---|
| 97 | 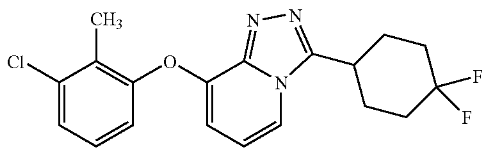 | 378 | 98 |
| 98 | 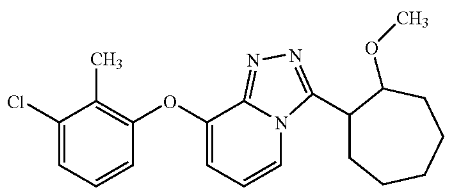 | 386 | 96 |
| 99 | 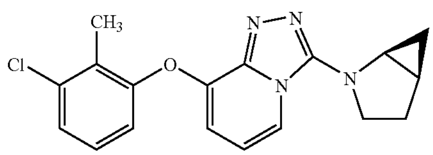 | 341 | 96 |
| 100 | 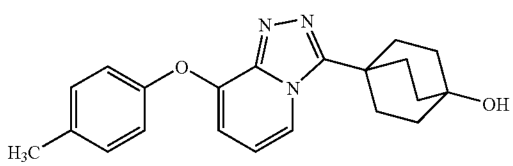 | 350 | 99 |
| 101 | 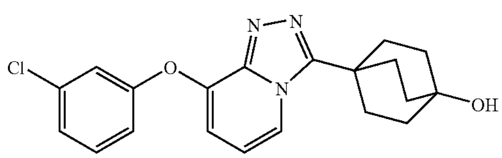 | 370 | 99 |
| 102 | 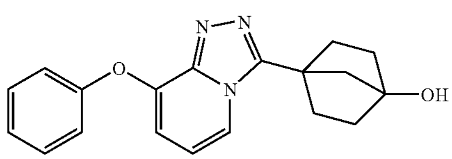 | 322 | 96 |
| 103 | 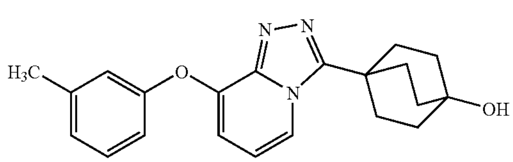 | 350 | 99 |
| 104 | 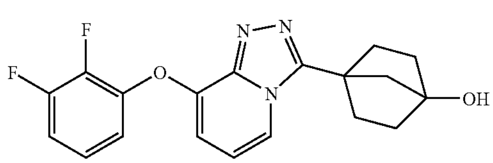 | 358 | 94 |
| 105 | 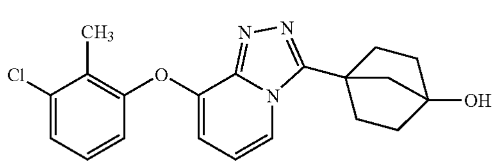 | 370 | 99 |

TABLE 1-continued

| Example | Structure | LC/MS Mass (M + H) | HPLC purity (%) |
|---|---|---|---|
| 106 | 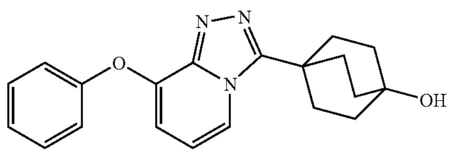 | 336 | 99 |
| 107 | 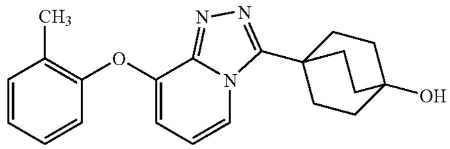 | 350 | 98 |
| 108 | 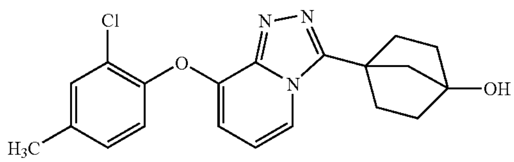 | 370 | 95 |
| 109 | 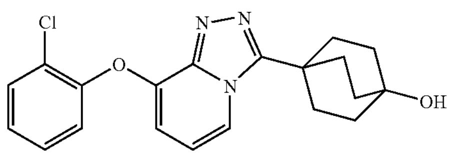 | 370 | 99 |
| 110 | 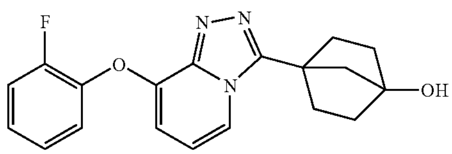 | 340 | 96 |
| 111 | 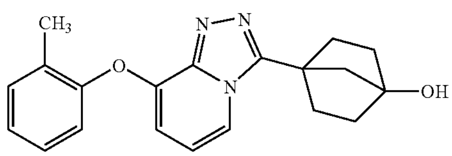 | 336 | 96 |
| 112 | 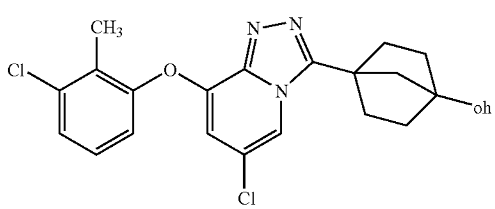 | 404 | 98 |
| 113 | 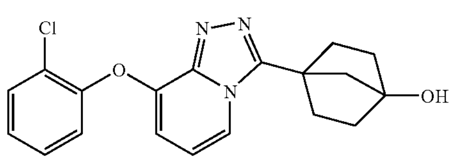 | 356 | 97 |
| 114 | 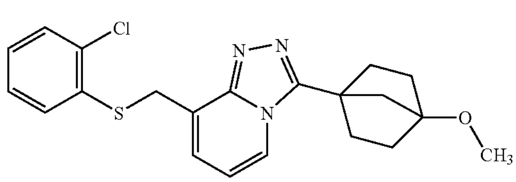 | 400 | 96 |

TABLE 1-continued
| Example | Structure | LC/MS Mass (M + H) | HPLC purity (%) |
|---|---|---|---|
| 115 | 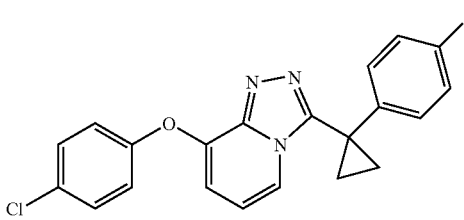 | 396 | 95 |
| 116 | 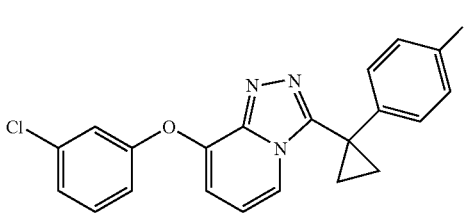 | 396 | 97 |
| 117 | 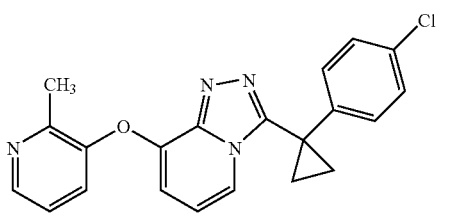 | 377 | 95 |
| 118 | 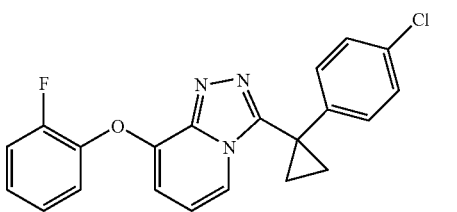 | 380 | 97 |
| 119 | 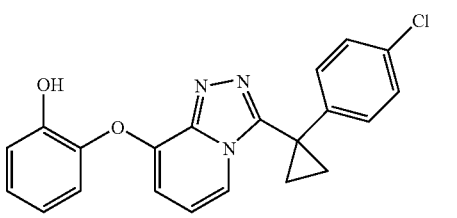 | 378 | 97 |
| 120 | 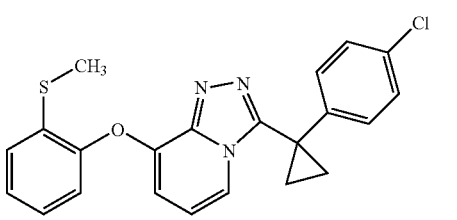 | 408 | 97 |
| 121 | 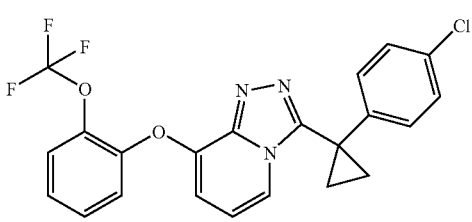 | 446 | 95 |

TABLE 1-continued

| Example | Structure | LC/MS Mass (M + H) | HPLC purity (%) |
| --- | --- | --- | --- |
| 122 | 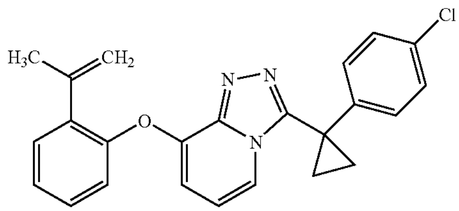 | 402 | 95 |
| 123 | 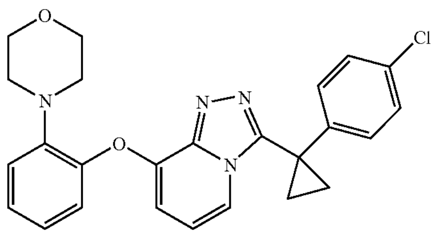 | 447 | 95 |
| 124 | 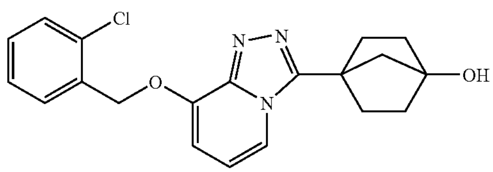 | 370 | 100 |
| 125 | 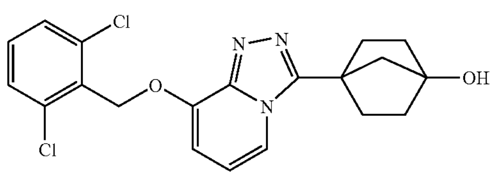 | 404 | 100 |
| 126 | 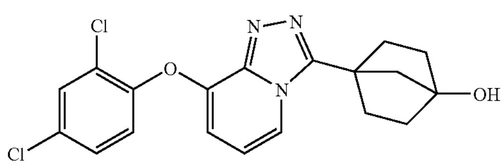 | 390 | 95 |
| 127 | 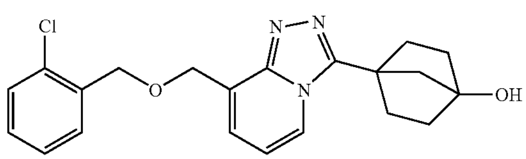 | 384 | 90 |
| 128 | 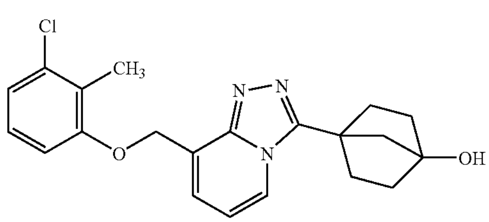 | 384 | 97 |
| 129 | 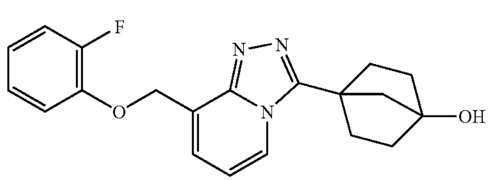 | 354 | 97 |

TABLE 1-continued

| Example | Structure | LC/MS Mass (M + H) | HPLC purity (%) |
|---|---|---|---|
| 130 | 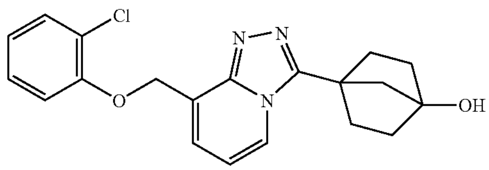 | 370 | 97 |
| 131 | 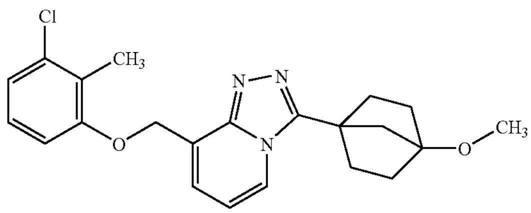 | 398 | 95 |
| 132 | 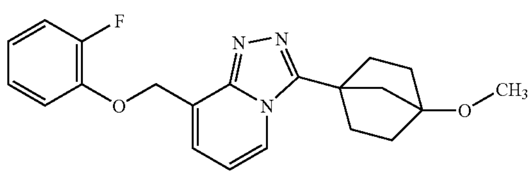 | 368 | 95 |
| 133 | 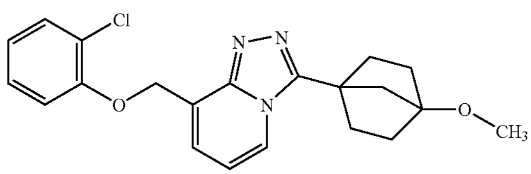 | 384 | 95 |
| 134 | 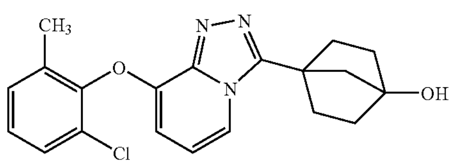 | 370 | 94 |
| 135 | 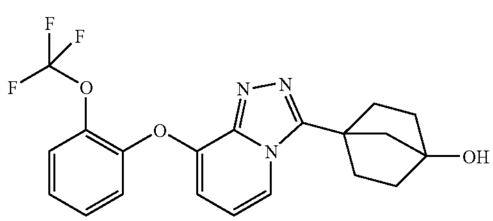 | 406 | 97 |
| 136 | 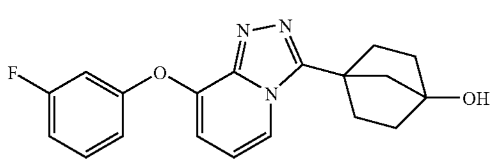 | 340 | 96 |
| 137 | 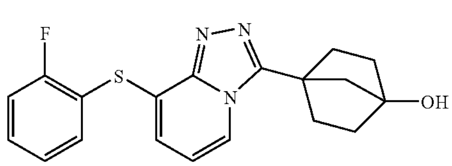 | 356 | 97 |

TABLE 1-continued

| Example | Structure | LC/MS Mass (M + H) | HPLC purity (%) |
| --- | --- | --- | --- |
| 138 | 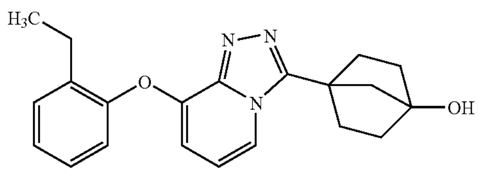 | 350 | 97 |
| 139 | 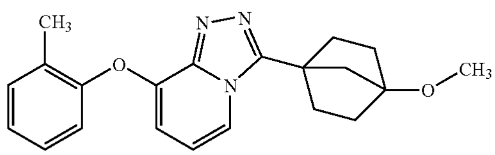 | 350 | 98 |
| 140 | 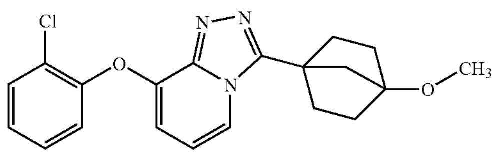 | 370 | 95 |
| 141 | 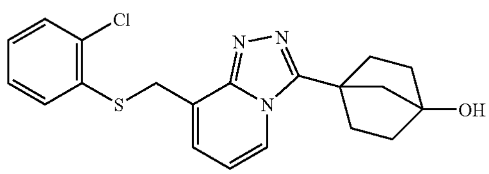 | 386 | 96 |
| 142 | 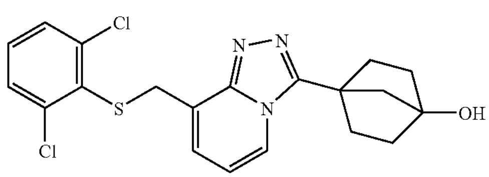 | 420 | 95 |
| 143 | 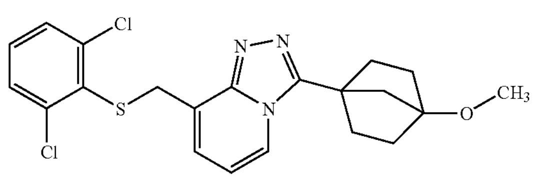 | 434 | 96 |
| 144 | 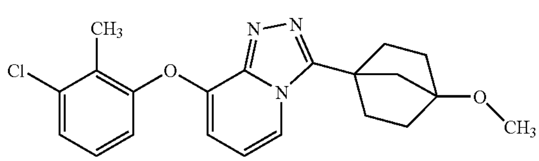 | 384 | 99 |
| 145 | 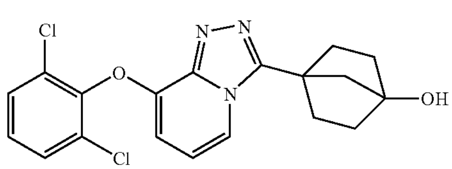 | 390 | 95 |

TABLE 1-continued

| Example | Structure | LC/MS Mass (M + H) | HPLC purity (%) |
| --- | --- | --- | --- |
| 146 | 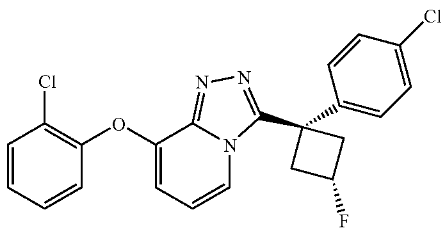 | 428 | 96 |
| 147 | 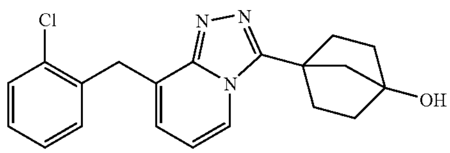 | 200 | 98 |
| 148 | 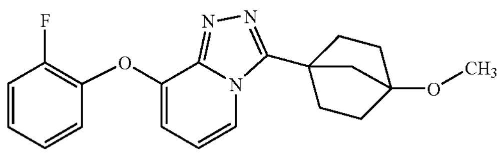 | 353 | 97 |
| 149 | 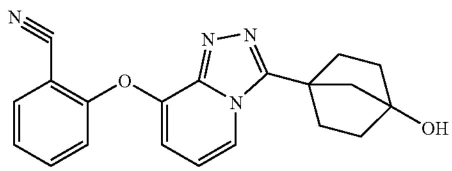 | 347 | 95 |
| 150 | 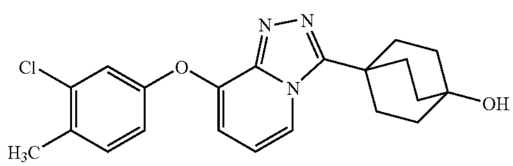 | 384 | 99 |
| 151 | 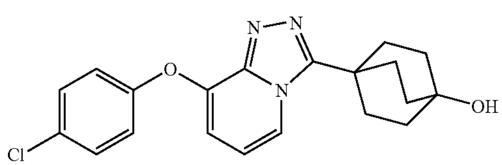 | 370 | 99 |
| 152 | 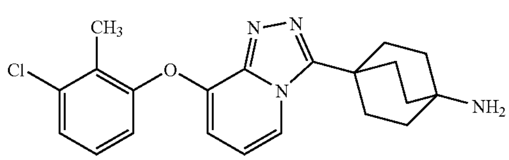 | 383 | 97 |
| 153 | 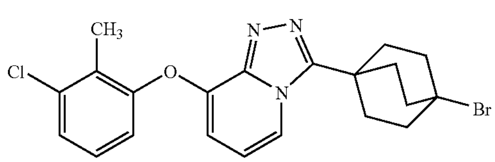 | 446 | 99 |
| 154 | 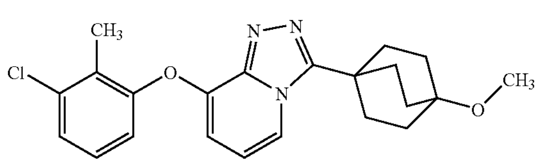 | 398 | 99 |

TABLE 1-continued

| Example | Structure | LC/MS Mass (M + H) | HPLC purity (%) |
|---------|-----------|---------------------|------------------|
| 155 | 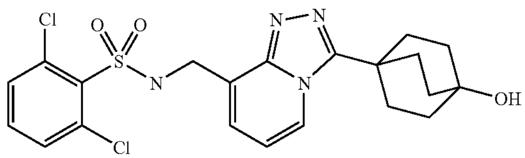 | 481 | 97 |
| 156 | 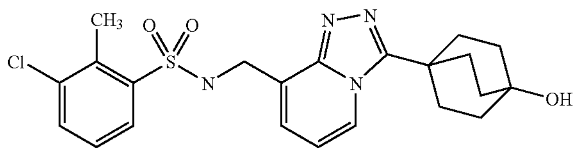 | 461 | 95 |
| 157 | 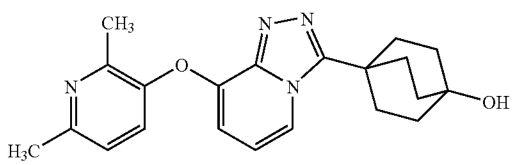 | 365 | 98 |
| 158 | 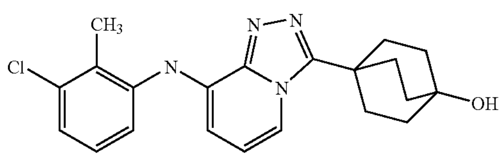 | 383 | 98 |
| 159 | 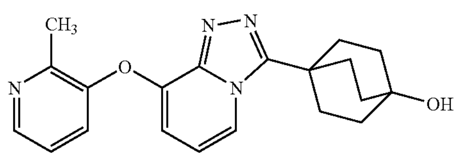 | 351 | 98 |
| 160 | 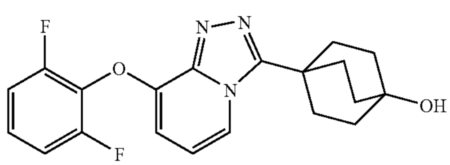 | 372 | 95 |
| 161 | 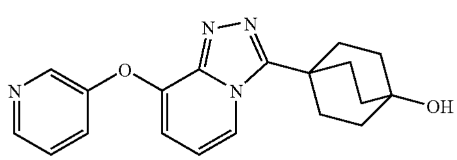 | 337 | 97 |
| 162 | 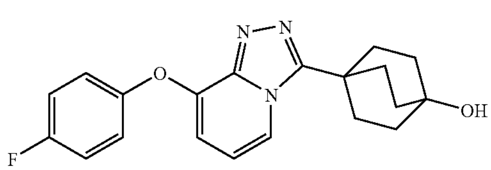 | 354 | 97 |
| 163 | 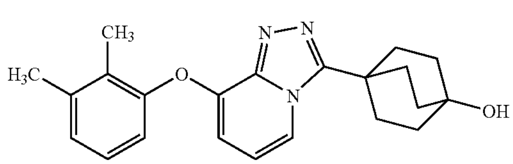 | 364 | 98 |

TABLE 1-continued

| Example | Structure | LC/MS Mass (M + H) | HPLC purity (%) |
|---|---|---|---|
| 164 | 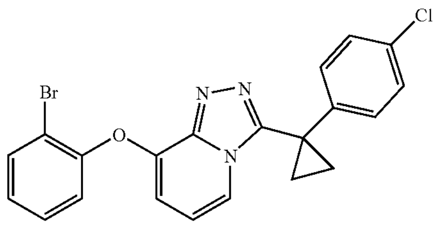 | 440 | 90 |
| 165 | 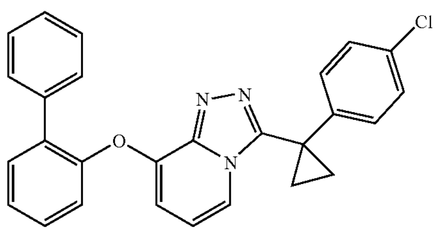 | 438 | 95 |
| 166 | 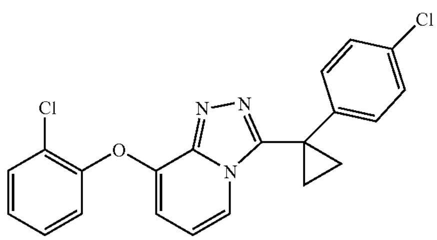 | 396 | 95 |
| 167 | 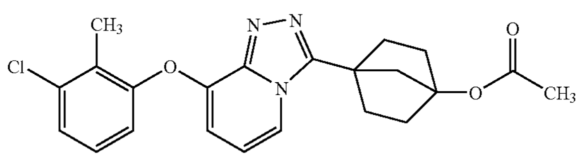 | 412 | 96 |
| 168 | 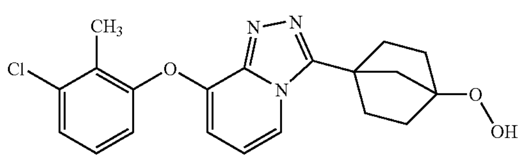 | 384 | 95 |
| 169 | 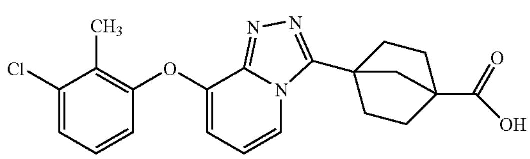 | 398 | 95 |
| 170 | 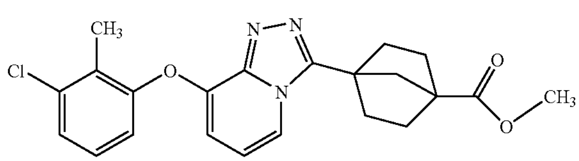 | 412 | 96 |
| 171 | 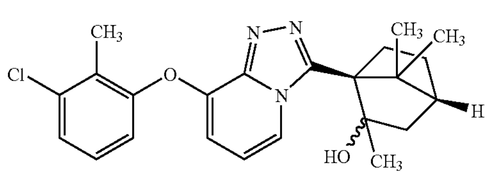 | 412 | 95 |

TABLE 1-continued

| Example | Structure | LC/MS Mass (M + H) | HPLC purity (%) |
|---|---|---|---|
| 172 | 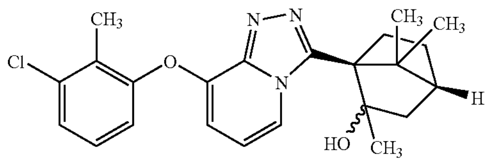 | 412 | 95 |
| 173 | 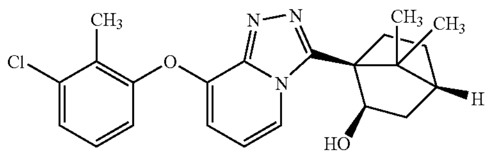 | 398 | 96 |
| 174 | 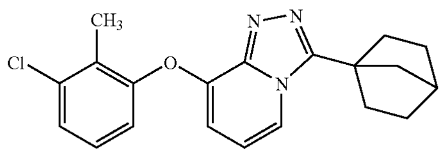 | 354 | 95 |
| 175 | 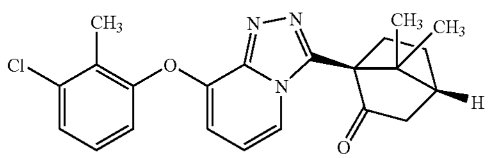 | 396 | 97 |
| 176 | 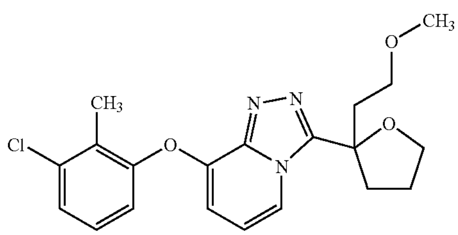 | 388 | 95 |
| 177 | 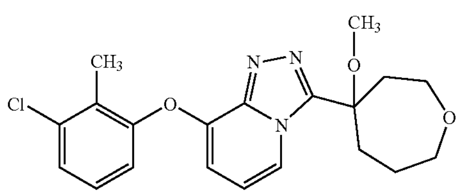 | 388 | 96 |
| 178 | 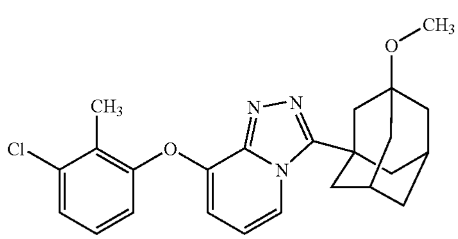 | 424 | 97 |
| 179 | 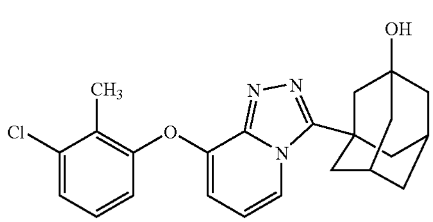 | 410 | 95 |

TABLE 1-continued

| Example | Structure | LC/MS Mass (M + H) | HPLC purity (%) |
|---|---|---|---|
| 180 | 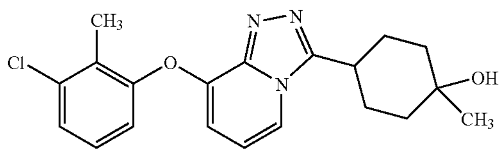 | 372 | 97 |
| 181 | 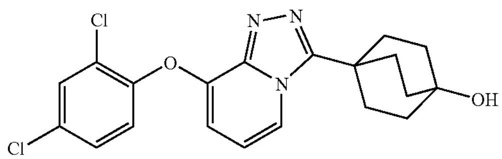 | 404 | 97 |
| 182 | 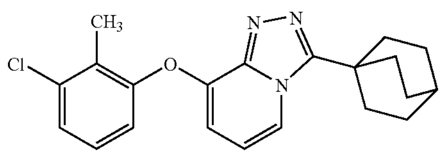 | 368 | 97 |
| 183 | 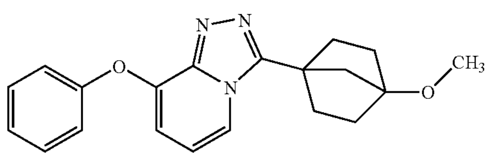 | 336 | 98 |

What is claimed is:

1. A compound of formula (I)

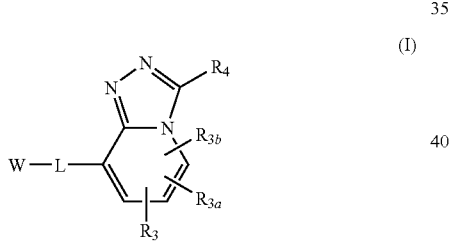

enantiomers, diastereomers, or salts thereof wherein:

W is aryl, which may be optionally substituted with $R_1$, $R_{1a}$, $R_{1b}$, $R_{1c}$ and $R_{1d}$;

$R_1$, $R_{1a}$, $R_{1b}$, $R_{1c}$ and $R_{1d}$ are independently hydrogen, halogen, —OH, —CN, —NO$_2$, —CO$_2$R$_{2a}$, —CONR$_2$R$_{2a}$, —SO$_2$NR$_2$R$_{2a}$, —SOR$_{2a}$, —SO$_2$R$_{2a}$, —NR$_2$SO$_2$R$_6$, —NR$_2$CO$_2$R$_6$, alkyl, haloalkyl, cycloalkyl, alkoxy, aryloxy, alkenyl, haloalkoxy, alkylthio, arylthio, arylsulfonyl, alkylamino, aminoalkyl, arylamino, heteroarylamino, aryl, heteroaryl or heterocyclyl, wherein the aryl, heteroaryl or heterocyclyl may be optionally substituted with R$_7$, R$_{7a}$, R$_{7b}$, and R$_{7c}$;

or alternatively any two $R_1$, $R_{1a}$, $R_{1b}$, $R_{1c}$, and $R_{1d}$ can be taken together to form a fused aryl, heteroaryl, heterocyclyl ring or spiro heterocyclyl ring;

L is O;

$R_2$ and $R_{2a}$ are independently hydrogen, halogen, alkyl or haloalkyl;

or alternatively $R_2$ and $R_{2a}$ can be taken together with the atom to which they are attached to form a cycloalkyl, halogen substituted cycloalkyl or heterocyclyl ring;

$R_3$, $R_{3a}$ and $R_{3b}$ are independently hydrogen, halogen, —OH, —CN, —NO$_2$, —CO$_2$R$_{2a}$, —CONR$_2$R$_{2a}$, —SO$_2$NR$_2$R$_{2a}$, —SOR$_{2a}$, —SO$_2$R$_{2a}$, —NR$_2$SO$_2$R$_6$, —NR$_2$CO$_2$R$_6$, alkyl, haloalkyl, cycloalkyl, alkoxy, aryloxy, alkenyl, haloalkoxy, alkylthio, arylthio, arylsulfonyl, alkylamino, aminoalkyl, arylamino, heteroarylamino, aryl, heteroaryl or heterocyclyl, wherein the aryl, heteroaryl or heterocyclyl may be optionally substituted with R$_7$, R$_{7a}$, R$_{7b}$, and R$_{7c}$;

$R_4$ is bicyclo[2,2,2]octyl or bicyclo[2,2,1]heptyl, both of which may be optionally substituted with one or more substituents selected from halogen, —OH, —OR$_6$, —SR$_6$, —OCOR$_6$, —CN, —NR$_5$COR$_6$, —NR$_5$SO$_2$R$_6$, —COR$_6$, —CO$_2$R$_6$, —CO$_2$H, —OCONR$_2$R$_{2a}$, —CONR$_2$R$_{2a}$, —NR$_5$CO$_2$R$_6$, —SO$_2$R$_6$, alkyl, alkoxy, aryl, amino, heterocyclyl or heteroaryl, wherein the alkyl, alkoxy, aryl, heteroaryl or heterocyclyl may be optionally substituted with R$_7$, R$_{7a}$, R$_{7b}$, and R$_{7c}$; or $R_4$ is cycloalkyl, other than bicyclo[2,2,2]octyl or bicyclo [2,2,1]heptyl, which may be optionally substituted with one or more substituents selected from halogen, —OH, —OR$_6$, —SR$_6$, —OCOR$_6$, —CN, —NR$_5$COR$_6$, —NR$_5$SO$_2$R$_6$, —COR$_6$, —CO$_2$R$_6$, —CO$_2$H, —OCONR$_2$R$_{2a}$, —CONR$_2$R$_{2a}$, —NR$_5$CO$_2$R$_6$, —SO$_2$R$_6$, alkyl, alkoxy, aryl, amino, heterocyclyl or heteroaryl, wherein the alkyl, alkoxy, aryl, heteroaryl or heterocyclyl may be optionally substituted with R$_7$, R$_{7a}$, R$_{7b}$, and R$_{7c}$; or $R_4$ is heterocyclyl, which may be optionally substituted with one or more substituents selected from halogen, —OH, —OR$_6$, —SR$_6$, —OCOR$_6$, —CN, —NR$_5$COR$_6$, —NR$_5$SO$_2$R$_6$, —COR$_6$, —CO$_2$R$_6$, —CO$_2$H, —OCONR$_2$R$_{2a}$, —CONR$_2$R$_{2a}$, —NR$_5$CO$_2$R$_6$, —SO$_2$R$_6$, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$;

$R_5$, at each occurrence, is independently hydrogen, alkyl, cycloalkyl, aryl, haloalkyl, $COR_{2a}$, $CO_2R_{2a}$, $SO_2NR_2R_{2a}$, or $SO_2R_{2a}$;

$R_6$, at each occurrence, is independently alkyl, cycloalkyl, aryl or heteroaryl, all of which may be optionally substituted with $R_7$, $R_{7a}$, $R_{7b}$, and $R_{7c}$; and $R_7$, $R_{7a}$, $R_{7b}$, and $R_{7c}$, at each occurrence, are independently halo, alkyl, haloalkyl, alkoxy, aryl, aryloxy, arylaryl, arylalkyl, arylalkyloxy, alkenyl, cycloalkyl, cycloalkylalkyl, cycloalkylalkyloxy, amino, —OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —$NO_2$, —CN or thiol.

2. The compound of claim 1, wherein W is phenyl, which is optionally substituted with $R_1$, $R_{1a}$, $R_{1b}$, $R_{1c}$ and $R_{1d}$.

3. The compound of claim 1, wherein:

W is aryl, which may be optionally substituted with $R_1$, $R_{1a}$, $R_{1b}$, $R_{1c}$ and $R_{1d}$;

$R_1$, $R_{1a}$, $R_{1b}$, $R_{1c}$ and $R_{1d}$ are independently hydrogen, halogen, —OH, —CN, —$NO_2$, —$CO_2R_{2a}$, —$CONR_2R_{2a}$, —$SO_2NR_2R_{2a}$, —$SOR_{2a}$, —$SO_2R_{2a}$, —$NR_2SO_2R_6$, —$NR_2CO_2R_6$, alkyl, haloalkyl, cycloalkyl, alkoxy, aryloxy, alkenyl, haloalkoxy, alkylthio, arylthio, arylsulfonyl, alkylamino, aminoalkyl, arylamino, heteroarylamino, aryl, heteroaryl or heterocyclyl, wherein the aryl, heteroaryl or heterocyclyl may be optionally substituted with $R_7$, $R_{7a}$, $R_{7b}$, and $R_{7c}$;

L is O;

$R_2$ and $R_{2a}$ are independently hydrogen, halogen, alkyl or haloalkyl;

$R_3$, $R_{3a}$ and $R_{3b}$ are independently hydrogen, halogen, —OH, —CN, —$NO_2$, —$CO_2R_{2a}$, —$CONR_2R_{2a}$, —$SO_2NR_2R_{2a}$, —$SOR_{2a}$, —$SO_2R_{2a}$, —$NR_2SO_2R_6$, —$NR_2CO_2R_6$, alkyl, haloalkyl, cycloalkyl, alkoxy, aryloxy, alkenyl, haloalkoxy, alkylthio, arylthio, arylsulfonyl, alkylamino, aminoalkyl, arylamino, heteroarylamino, aryl, heteroaryl or heterocyclyl, wherein the aryl, heteroaryl or heterocyclyl may be optionally substituted with $R_7$, $R_{7a}$, $R_{7b}$, and $R_{7c}$;

$R_4$ is bicyclo[2,2,2]octyl or bicyclo[2,2,1]heptyl, both of which may be optionally substituted with one or more substituents selected from halogen, —OH, —$OR_6$, —$SR_6$, —$OCOR_6$, —CN, —$NR_5COR_6$, —$NR_5SO_2R_6$, —$COR_6$, —$CO_2R_6$, —$CO_2H$, —$OCONR_2R_{2a}$, —$CONR_2R_{2a}$, —$NR_5CO_2R_6$, —$SO_2R_6$, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$; or $R_4$ is cycloalkyl, other than bicyclo[2,2,2]octyl or bicyclo[2,2,1]heptyl, which may be optionally substituted with one or more substituents selected from halogen, —OH, —$OR_6$, —$SR_6$, —$OCOR_6$, —CN, —$NR_5COR_6$, —$NR_5SO_2R_6$, —$COR_6$, —$CO_2R_6$, —$CO_2H$, —$OCONR_2R_{2a}$, —$CONR_2R_{2a}$, —$NR_5CO_2R_6$, —$SO_2R_6$, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$; or $R_4$ is heterocyclyl, which may be optionally substituted with one or more substituents selected from halogen, —OH, —$OR_6$, —$SR_6$, —$OCOR_6$, —CN, —$NR_5COR_6$, —$NR_5SO_2R_6$, —$COR_6$, —$CO_2R_6$, —$CO_2H$, —$OCONR_2R_{2a}$, —$CONR_2R_{2a}$, —$NR_5CO_2R_6$, —$SO_2R_6$, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$;

$R_5$, at each occurrence, is independently hydrogen, alkyl, cycloalkyl, aryl, haloalkyl, $COR_{2a}$ or $CO_2R_{2a}$;

$R_6$, at each occurrence, is independently alkyl, cycloalkyl, aryl or heteroaryl, all of which may be optionally substituted with $R_7$, $R_{7a}$, $R_{7b}$, and $R_{7c}$; and $R_7$, $R_{7a}$, $R_{7b}$, and $R_{7c}$, at each occurrence, are independently halo, alkyl, haloalkyl, alkoxy, aryl, aryloxy, arylaryl, arylalkyl, arylalkyloxy, alkenyl, cycloalkyl, cycloalkylalkyl, cycloalkylalkyloxy, amino, —OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —$NO_2$, —CN or thiol.

4. The compound of claim 1, wherein:

W is aryl, which may be optionally substituted with $R_1$, $R_{1a}$, $R_{1b}$, $R_{1c}$ and $R_{1d}$;

$R_1$, $R_{1a}$, $R_{1b}$, $R_{1c}$ and $R_{1d}$ are independently hydrogen, halogen, —OH, —CN, —$NO_2$, —$CO_2R_{2a}$, —$CONR_2R_{2a}$, —$SO_2NR_2R_{2a}$, —$SOR_{2a}$, —$SO_2R_{2a}$, alkyl, haloalkyl, cycloalkyl, alkoxy, aryloxy, haloalkoxy, alkylthio, arylthio, arylsulfonyl, alkylamino, aminoalkyl, arylamino, heteroarylamino, aryl, heteroaryl or heterocyclyl, wherein the aryl, heteroaryl or heterocyclyl may be optionally substituted with $R_7$, $R_{7a}$, $R_{7b}$, and $R_{7c}$;

L is O;

$R_2$ and $R_{2a}$ are independently hydrogen, halogen, alkyl or haloalkyl;

$R_3$, $R_{3a}$ and $R_{3b}$ are independently hydrogen, halogen, —OH, —CN, —$NO_2$, —$CO_2R_{2a}$, —$CONR_2R_2$, —$SO_2NR_2R_{2a}$, —$SOR_{2a}$, —$SO_2R_{2a}$, alkyl, haloalkyl, cycloalkyl, alkoxy, aryloxy, haloalkoxy, alkylthio, arylthio, arylsulfonyl, alkylamino, aminoalkyl, arylamino, heteroarylamino, aryl, heteroaryl or heterocyclyl, wherein the aryl, heteroaryl or heterocyclyl may be optionally substituted with $R_7$, $R_{7a}$, $R_{7b}$, and $R_{7c}$;

$R_4$ is bicyclo[2,2,2]octyl or bicyclo[2,2,1]heptyl, both of which may be optionally substituted with one or more substituents selected from halogen, —OH, —$OR_6$, —$SR_6$, —$OCOR_6$, —CN, —$COR_6$, —$CO_2R_6$, —$CO_2H$, —$OCONR_2R_{2a}$, —$CONR_2R_{2a}$, —$SO_2R_6$, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$; or $R_4$ is cycloalkyl, other than bicyclo[2,2,2]octyl or bicyclo[2,2,1]heptyl, which may be optionally substituted with one or more substituents selected from halogen, —OH, —$OR_6$, —$SR_6$, —$OCOR_6$, —CN, —$COR_6$, —$CO_2R_6$, —$CO_2H$, —$OCONR_2R_{2a}$, —$CONR_2R_{2a}$, —$SO_2R_6$, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$; or $R_4$ is heterocyclyl, which may be optionally substituted with one or more substituents selected from halogen, —OH, —$OR_6$, —$SR_6$, —$OCOR_6$, —CN, —$COR_6$, —$CO_2R_6$, —$CO_2H$, —$OCONR_2R_{2a}$, —$CONR_2R_{2a}$, —$SO_2R_6$, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$;

$R_6$, at each occurrence, is independently alkyl, cycloalkyl, aryl or heteroaryl, all of which may be optionally substituted with $R_7$, $R_{7a}$, $R_{7b}$, and $R_{7c}$; and $R_7$, $R_{7a}$, $R_{7b}$, and $R_{7c}$, at each occurrence, are independently halo, alkyl, haloalkyl, alkoxy, aryl, aryloxy, arylaryl, arylalkyl, arylalkyloxy, alkenyl, cycloalkyl, cycloalkylalkyl, cycloalkylalkyloxy, amino, —OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —NO$_2$, —CN or thiol.

5. The compound of claim 1, wherein:

W is aryl which may be optionally substituted with $R_1$, $R_{1a}$, $R_{1b}$, $R_{1c}$ and $R_{1d}$;

$R_1$, $R_{1a}$, $R_{1b}$, $R_{1c}$ and $R_{1d}$ are independently hydrogen, halogen, —OH, —CN, —NO$_2$, —CO$_2R_{2a}$, —CONR$_2R_{2a}$, —SO$_2$NR$_2R_{2a}$, alkyl, haloalkyl, cycloalkyl, alkoxy, aryloxy, haloalkoxy, alkylthio, arylthio, arylsulfonyl, alkylamino, aminoalkyl, arylamino, heteroarylamino, aryl, heteroaryl or heterocyclyl, wherein the aryl, heteroaryl or heterocyclyl may be optionally substituted with $R_7$, $R_{7a}$, $R_{7b}$, and $R_{7c}$;

L is O;

$R_2$ and $R_{2a}$ are independently hydrogen, halogen, alkyl or haloalkyl;

$R_3$, $R_{3a}$ and $R_{3b}$ are independently hydrogen, halogen, —OH, —CN, —NO$_2$, —CO$_2R_{2a}$, —CONR$_2R_2$, —SO$_2$NR$_2R_{2a}$, alkyl, haloalkyl, cycloalkyl, alkoxy, aryloxy, haloalkoxy, alkylthio, arylthio, arylsulfonyl, alkylamino, aminoalkyl, arylamino, heteroarylamino, aryl, heteroaryl or heterocyclyl, wherein the aryl, heteroaryl or heterocyclyl may be optionally substituted with $R_7$, $R_{7a}$, $R_{7b}$, and $R_{7c}$;

$R_4$ is bicyclo[2,2,2]octyl or bicyclo[2,2,1]heptyl, both of which may be optionally substituted with one or more substituents selected from halogen, —OH, —OR$_6$, —SR$_6$, —OCOR$_6$, —CN, —COR$_6$, —CO$_2R_6$, —CO$_2$H, —OCONR$_2R_{2a}$, —CONR$_2R_{2a}$, —SO$_2R_6$, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$; or $R_4$ is cycloalkyl, other than bicyclo[2,2,2]octyl or bicyclo[2,2,1]heptyl, which may be optionally substituted with one or more substituents selected from halogen, —OH, —OR$_6$, —SR$_6$, —OCOR$_6$, —CN, —COR$_6$, —CO$_2R_6$, —CO$_2$H, —OCONR$_2R_{2a}$, —CONR$_2R_{2a}$, —SO$_2R_6$, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$; or $R_4$ is heterocyclyl, which may be optionally substituted with one or more substituents selected from halogen, —OH, —OR$_6$, —SR$_6$, —OCOR$_6$, —CN, —COR$_6$, —CO$_2R_6$, —CO$_2$H, —OCONR$_2R_{2a}$, —CONR$_2R_{2a}$, —SO$_2R_6$, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$;

$R_6$, at each occurrence, is independently alkyl, cycloalkyl, aryl or heteroaryl, all of which may be optionally substituted with $R_7$, $R_{7a}$, $R_{7b}$, and $R_{7c}$; and $R_7$, $R_{7a}$, $R_{7b}$, and $R_{7c}$, at each occurrence, are independently halo, alkyl, haloalkyl, alkoxy, aryl, aryloxy, arylaryl, arylalkyl, arylalkyloxy, alkenyl, cycloalkyl, cycloalkylalkyl, cycloalkylalkyloxy, amino, —OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —NO$_2$, —CN or thiol.

6. The compound of claim 1, wherein:

W is aryl which may be optionally substituted with $R_1$, $R_{1a}$, $R_{1b}$, $R_{1c}$ and $R_{1d}$;

$R_1$, $R_{1a}$, $R_{1b}$, $R_{1c}$ and $R_{1d}$ are independently hydrogen, halogen, —OH, —CN, —NO$_2$, —CO$_2R_{2a}$, alkyl, haloalkyl, cycloalkyl, alkoxy, aryloxy, haloalkoxy, alkylthio, arylthio, arylsulfonyl, alkylamino, aminoalkyl, arylamino, heteroarylamino, aryl, heteroaryl or heterocyclyl, wherein the aryl, heteroaryl or heterocyclyl may be optionally substituted with $R_7$, $R_{7a}$, $R_{7b}$, and $R_{7c}$;

L is O;

$R_2$ and $R_{2a}$ are independently hydrogen, halogen, alkyl or haloalkyl;

$R_3$, $R_{3a}$ and $R_{3b}$ are independently hydrogen, halogen, —OH, —CN, —NO$_2$, —CO$_2R_{2a}$, alkyl, haloalkyl, cycloalkyl, alkoxy, aryloxy, haloalkoxy, alkylthio, arylthio, arylsulfonyl, alkylamino, aminoalkyl, arylamino, heteroarylamino, aryl, heteroaryl or heterocyclyl, wherein the aryl, heteroaryl or heterocyclyl may be optionally substituted with $R_7$, $R_{7a}$, $R_{7b}$, and $R_{7c}$;

$R_4$ is bicyclo[2,2,2]octyl or bicyclo[2,2,1]heptyl, both of which may be optionally substituted with one or more substituents selected from halogen, —OH, —OR$_6$, —SR$_6$, —CN, —COR$_6$, —CO$_2R_6$, —CO$_2$H, —CONR$_2R_{2a}$, —SO$_2R_6$, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$; or $R_4$ is cycloalkyl, other than bicyclo[2,2,2]octyl or bicyclo[2,2,1]heptyl, which may be optionally substituted with one or more substituents selected from halogen, —OH, —OR$_6$, —SR$_6$, —CN, —COR$_6$, —CO$_2R_6$, —CO$_2$H, —CONR$_2R_{2a}$, —SO$_2R_6$, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$; or $R_4$ is heterocyclyl, which may be optionally substituted with one or more substituents selected from halogen, —OH, —OR$_6$, —SR$_6$, —CN, —COR$_6$, —CO$_2R_6$, —CO$_2$H, —CONR$_2R_{2a}$, —SO$_2R_6$, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$;

$R_6$, at each occurrence, is independently alkyl, cycloalkyl, aryl or heteroaryl, all of which may be optionally substituted with $R_7$, $R_{7a}$, $R_{7b}$, and $R_{7c}$; and $R_7$, $R_{7a}$, $R_{7b}$, and $R_{7c}$, at each occurrence, are independently halo, alkyl, haloalkyl, alkoxy, aryl, aryloxy, arylaryl, arylalkyl, arylalkyloxy, alkenyl, cycloalkyl, cycloalkylalkyl, cycloalkylalkyloxy, amino, —OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —NO$_2$, —CN or thiol.

7. The compound of claim 1, wherein:

W is aryl, which is optionally substituted with $R_1$, $R_{1a}$, $R_{1b}$, $R_{1c}$ and $R_{1d}$;

$R_1$, $R_{1a}$, $R_{1b}$, $R_{1c}$ and $R_{1d}$ are independently hydrogen, halogen, —OH, —CN, —NO$_2$, alkyl, haloalkyl, cycloalkyl, alkoxy, aryloxy, haloalkoxy, alkylthio, arylthio, arylsulfonyl, alkylamino, aminoalkyl, arylamino, heteroarylamino, aryl, heteroaryl or heterocyclyl, wherein the aryl, heteroaryl or heterocyclyl may be optionally substituted with $R_7$, $R_{7a}$, $R_{7b}$, and $R_{7c}$;

L is O;

$R_2$ and $R_{2a}$ are independently hydrogen, halogen, alkyl or haloalkyl;

$R_3$, $R_{3a}$ and $R_{3b}$ are independently hydrogen, halogen, —OH, —CN, —NO$_2$, alkyl, haloalkyl, cycloalkyl, alkoxy, aryloxy, haloalkoxy, alkylthio, arylthio, arylsulfonyl, alkylamino, aminoalkyl, arylamino, heteroarylamino, aryl, heteroaryl or heterocyclyl, wherein the aryl, heteroaryl or heterocyclyl may be optionally substituted with $R_7$, $R_{7a}$, $R_{7b}$, and $R_{7c}$;

$R_4$ is bicyclo[2,2,2]octyl or bicyclo[2,2,1]heptyl, both of which may be optionally substituted with one or more substituents selected from halogen, —OH, —OR$_6$, —SR$_6$, —CN, —COR$_6$, —CO$_2$R$_6$, —CO$_2$H, —CONR$_2$R$_{2a}$, —SO$_2$R$_6$, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$; or $R_4$ is cycloalkyl, other than bicyclo[2,2,2]octyl or bicyclo[2,2,1]heptyl, which may be optionally substituted with one or more substituents selected from halogen, —OH, —OR$_6$, —SR$_6$, —CN, —COR$_6$, —CO$_2$R$_6$, —CO$_2$H, —CONR$_2$R$_{2a}$, —SO$_2$R$_6$, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$;

$R_6$, at each occurrence, is independently alkyl, cycloalkyl, aryl or heteroaryl, all of which may be optionally substituted with $R_7$, $R_{7a}$, $R_{7b}$, and $R_{7c}$; and $R_7$, $R_{7a}$, $R_{7b}$, and $R_{7c}$, at each occurrence, are independently halo, alkyl, haloalkyl, alkoxy, aryl, aryloxy, arylaryl, arylalkyl, arylalkyloxy, alkenyl, cycloalkyl, cycloalkylalkyl, cycloalkylalkyloxy, amino, —OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —NO$_2$, —CN or thiol.

8. The compound of claim 1, wherein:

W is aryl, which is optionally substituted with $R_1$, $R_{1a}$, $R_{1b}$, $R_{1c}$, and $R_{1d}$;

$R_1$, $R_{1a}$, $R_{1b}$, $R_{1c}$ and $R_{1d}$ are hydrogen, halogen, —OH, —CN, —NO$_2$, alkyl, haloalkyl, cycloalkyl, alkoxy, aryloxy, haloalkoxy, alkylthio, arylthio, arylsulfonyl, alkylamino, aminoalkyl, aryl, heteroaryl or heterocyclyl, wherein the aryl, heteroaryl or heterocyclyl may be optionally substituted with $R_7$, $R_{7a}$, $R_{7b}$, and $R_{7c}$;

L is O;

$R_3$, $R_{3a}$ and $R_{3b}$ are independently hydrogen, halogen, —OH, —CN, —NO$_2$, alkyl, haloalkyl, cycloalkyl, alkoxy, aryloxy, haloalkoxy, alkylthio, arylthio, arylsulfonyl, alkylamino, aminoalkyl, aryl, heteroaryl or heterocyclyl, wherein the aryl, heteroaryl or heterocyclyl may be optionally substituted with $R_7$, $R_{7a}$, $R_{7b}$, and $R_{7c}$;

$R_4$ is bicyclo[2,2,2]octyl or bicyclo[2,2,1]heptyl, both of which may be optionally substituted with one or more substituents selected from halogen, —OH, —OR$_6$, —SR$_6$, —CN, —COR$_6$, —CO$_2$R$_6$, —CO$_2$H, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$; or $R_4$ is cycloalkyl, other than bicyclo[2,2,2]octyl or bicyclo[2,2,1]heptyl, which may be optionally substituted with one or more substituents selected from halogen, —OH, —OR$_6$, —SR$_6$, —CN, —COR$_6$, —CO$_2$R$_6$, —CO$_2$H, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$;

$R_6$, at each occurrence, is independently alkyl, cycloalkyl, aryl or heteroaryl; and $R_7$, $R_{7a}$, $R_{7b}$, and $R_{7c}$, at each occurrence, are independently halo, alkyl, haloalkyl, alkoxy, aryl, aryloxy, arylaryl, arylalkyl, arylalkyloxy, alkenyl, cycloalkyl, cycloalkylalkyl, cycloalkylalkyloxy, amino, —OH, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, —NO$_2$, —CN or thiol.

9. The compound of claim 1, wherein:

W is phenyl, which is optionally substituted with $R_1$, $R_{1a}$, $R_{1b}$, $R_{1c}$ and $R_{1d}$;

$R_1$, $R_{1a}$, $R_{1b}$, $R_{1c}$ and $R_{1d}$ are independently hydrogen, halogen, —OH, —CN, —NO$_2$, alkyl, haloalkyl, cycloalkyl, alkoxy, aryloxy, haloalkoxy, alkylthio, arylthio, arylsulfonyl, alkylamino, aminoalkyl, aryl, heteroaryl or heterocyclyl;

L is O;

$R_3$, $R_{3a}$ and $R_{3b}$ are independently hydrogen, halogen, —OH, —CN, —NO$_2$, alkyl, haloalkyl, cycloalkyl, alkoxy, aryloxy, haloalkoxy, alkylthio, arylthio, arylsulfonyl, alkylamino, aminoalkyl, aryl, heteroaryl or heterocyclyl;

$R_4$ is bicyclo[2,2,2]octyl or bicyclo[2,2,1]heptyl, all which may be optionally substituted with one or more substituents selected from halogen, —OH, —OR$_6$, —SR$_6$, —CN, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$;

$R_6$, at each occurrence, is independently alkyl, cycloalkyl, aryl or heteroaryl; and $R_7$, $R_{7a}$, $R_{7b}$, and $R_{7c}$, at each occurrence, are independently halo, alkyl, haloalkyl, alkoxy, aryl, aryloxy, arylalkyl, cycloalkyl, amino, —OH, hydroxyalkyl, heteroaryl, heteroaryloxy, heteroarylalkyl, alkylthio, arylalkylthio, —NO$_2$, or —CN.

10. The compound of claim 1, wherein:

$R_4$ is bicyclo[2,2,2]octyl or bicyclo[2,2,1]heptyl, both of which may be optionally substituted with one or more substituents selected from halogen, —OH, —OR$_6$, —SR$_6$, —OCOR$_6$, —CN, —NR$_5$COR$_6$, —NR$_5$SO$_2$R$_6$, —COR$_6$, —CO$_2$R$_6$, —CO$_2$H, —OCONR$_2$R$_{2a}$, —CONR$_2$R$_{2a}$, —NR$_5$CO$_2$R$_6$, —SO$_2$R$_6$, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$.

11. The compound of claim 1 having the formula IA:

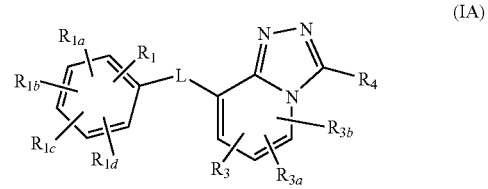

(IA)

wherein:

L is O; and $R_3$, $R_{3a}$ and $R_{3b}$ are independently selected from hydrogen, halogen, —CF$_3$, OCF$_3$, alkyl or alkoxyl.

12. The compound of claim 1 having the formula IA:

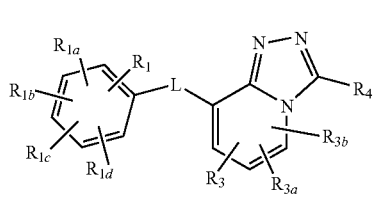
(IA)

wherein:

$R_1$, $R_{1a}$, $R_{1b}$, $R_{1c}$ and $R_{1d}$ are independently hydrogen, halogen, alkyl, haloalkyl, cycloalkyl, alkoxy, haloalkoxy, aryl, heteroaryl or heterocyclyl;

L is O;

$R_3$, $R_{3a}$ and $R_{3b}$ are independently selected from hydrogen or halogen;

$R_4$ is bicyclo[2,2,2]octyl or bicyclo[2,2,1]heptyl, both of which may be optionally substituted with one or more substituents selected from halogen, —OH, —OR$_6$, —OCOR$_6$, haloalkyl, haloalkoxy, aryl or heterocyclyl; and $R_6$, at each occurrence, is independently alkyl, or cycloalkyl.

13. The compound of claim 1 having the formula IA:

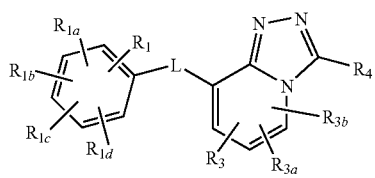
(IA)

wherein:

L is O;

$R_4$ is bicyclo[2,2,2]octyl or bicyclo[2,2,1]heptyl, both of which may be optionally substituted with one or more substituents selected from halogen, —OH, —OR$_6$, —SR$_6$, —OCOR$_6$, —CN, —NR$_5$COR$_6$, —NR$_5$SO$_2$R$_6$, —COR$_6$, —CO$_2$R$_6$, —CO$_2$H, —OCONR$_2$R$_{2a}$, —CONR$_2$R$_{2a}$, —NR$_5$CO$_2$R$_6$, —SO$_2$R$_6$, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$; or $R_4$ is cycloalkyl, other than bicyclo[2,2,2]octyl or bicyclo [2,2,1]heptyl, which may be optionally substituted with one or more substituents selected from halogen, —OH, —OR$_6$, —SR$_6$, —OCOR$_6$, —CN, —NR$_5$COR$_6$, —NR$_5$SO$_2$R$_6$, —COR$_6$, —CO$_2$R$_6$, —CO$_2$H, —OCONR$_2$R$_{2a}$, —CONR$_2$R$_{2a}$, —NR$_5$CO$_2$R$_6$, —SO$_2$R$_6$, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$; and $R_6$, at each occurrence, is independently alkyl or cycloalkyl.

14. The compound of claim 1 having the formula IA:

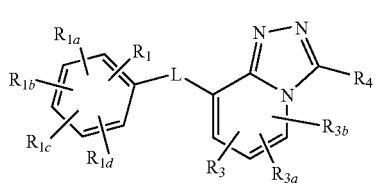
(IA)

wherein:

L is O;

$R_4$ is a fused or bridged cycloalkyl, other than bicyclo[2,2,2]octyl or bicyclo[2,2,1]heptyl, which may be optionally substituted with one or more substituents selected from halogen, —OH, —OR$_6$, —SR$_6$, —OCOR$_6$, —CN, —NR$_5$COR$_6$, —NR$_5$SO$_2$R$_6$, —COR$_6$, —CO$_2$R$_6$, —CO$_2$H, —OCONR$_2$R$_{2a}$, —CONR$_2$R$_{2a}$, —NR$_5$CO$_2$R$_6$, —SO$_2$R$_6$, alkyl, alkoxy, aryl, amino, heterocyclyl or heteroaryl, wherein the alkyl, alkoxy, aryl, heteroaryl or heterocyclyl may be optionally substituted with $R_7$, $R_{7a}$, $R_{7b}$, and $R_{7c}$; and $R_6$, at each occurrence, is independently alkyl or cycloalkyl.

15. A compound, enantiomer, diastereomer, or salt thereof, having the following formula:

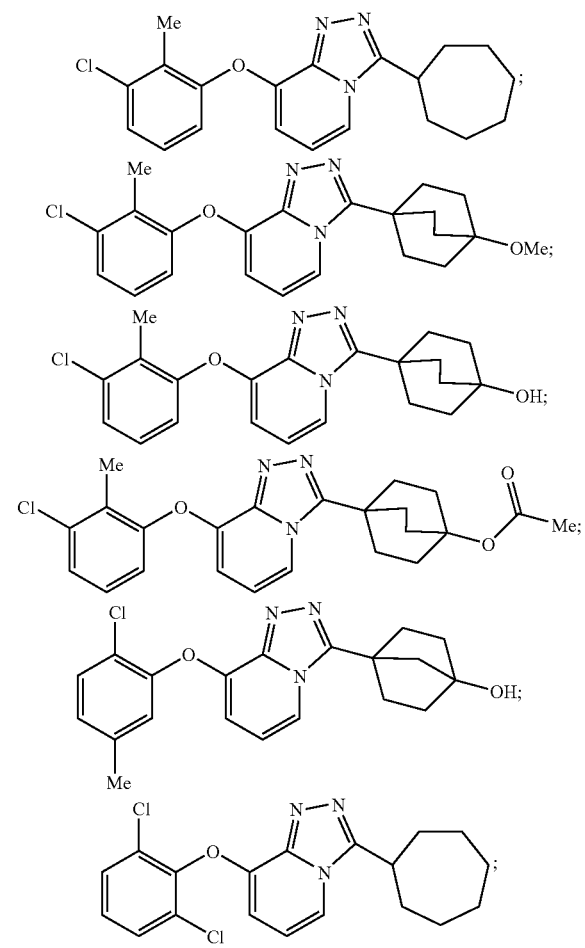

-continued
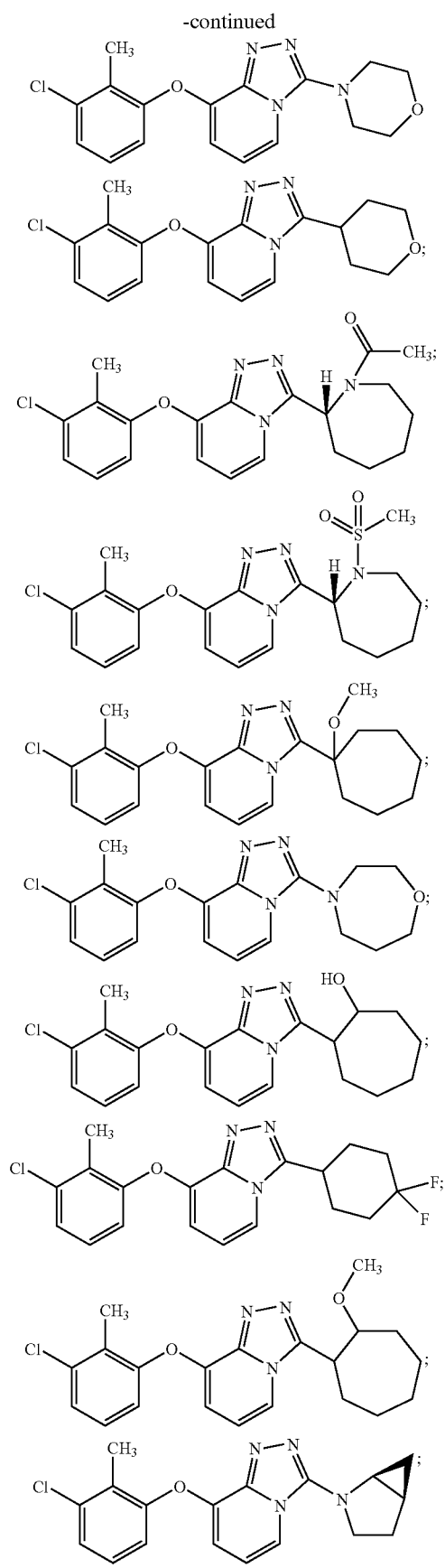
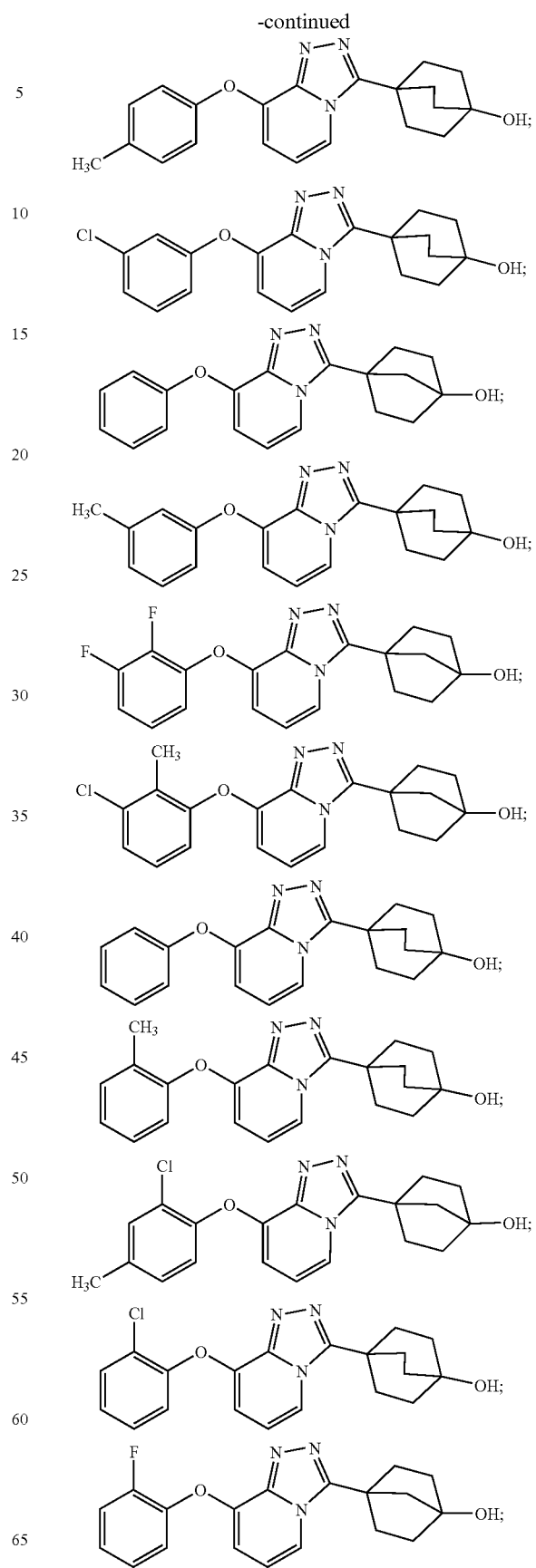

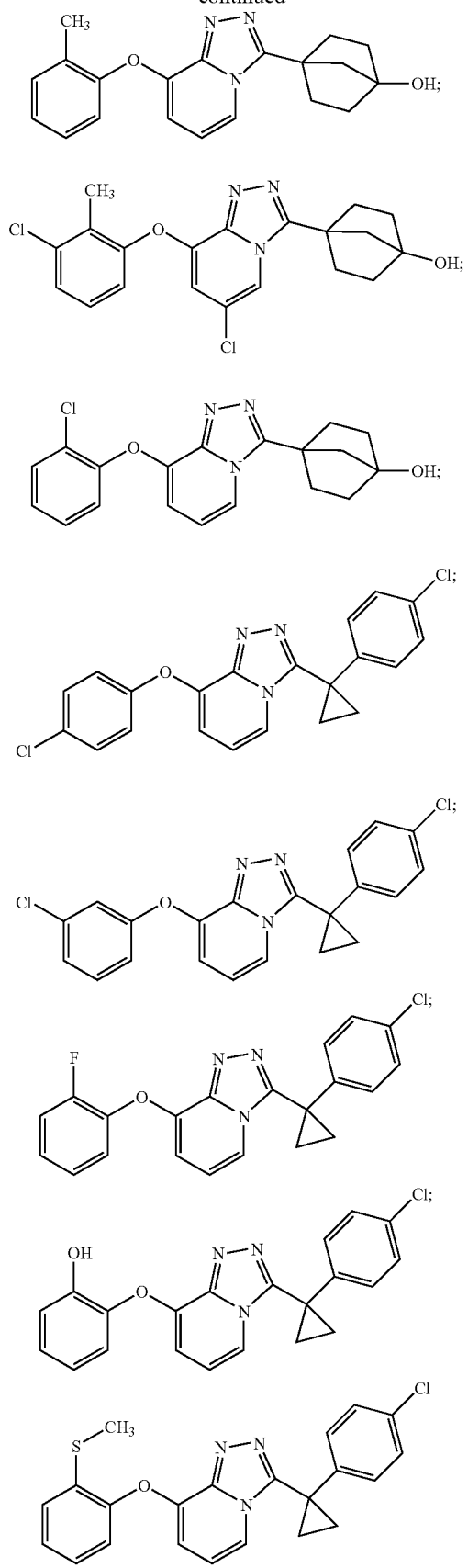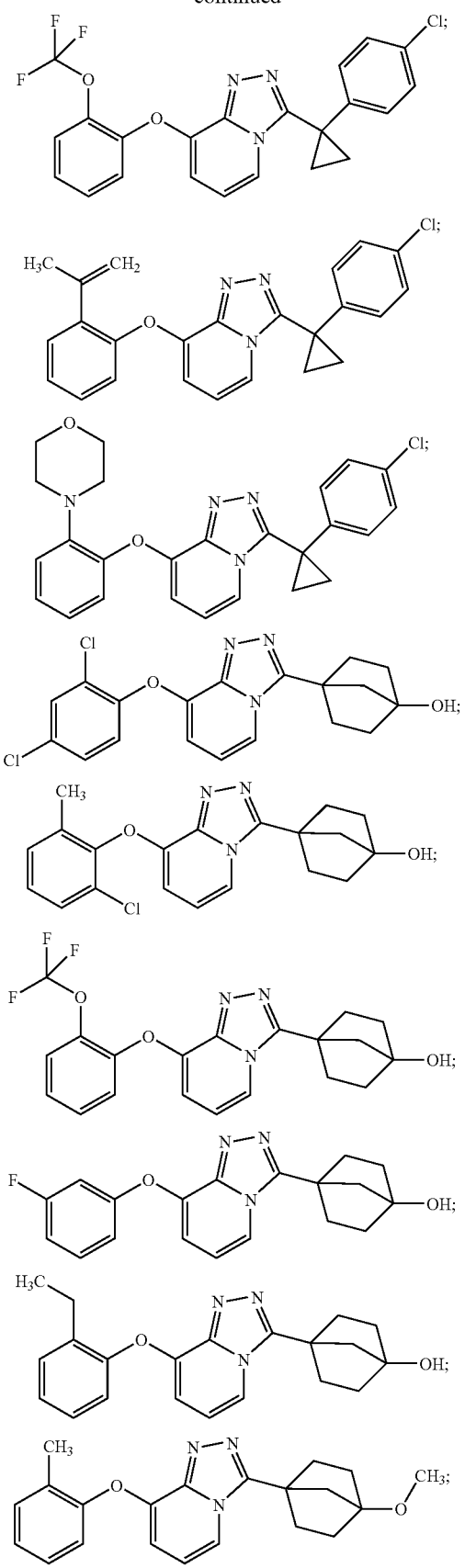

-continued
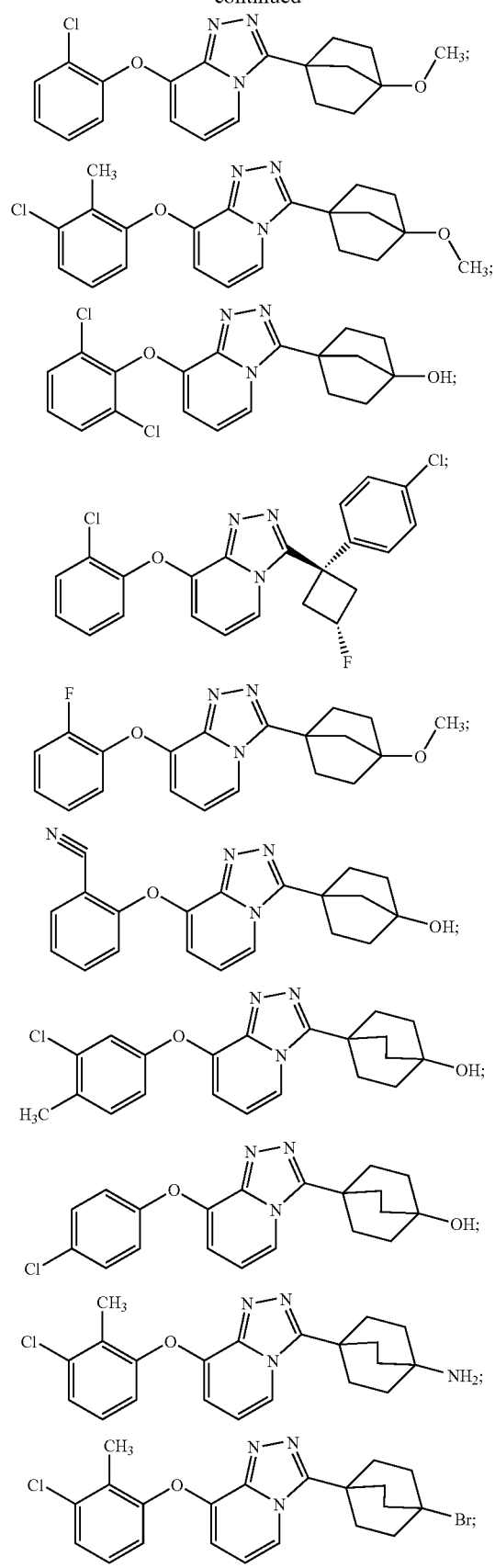
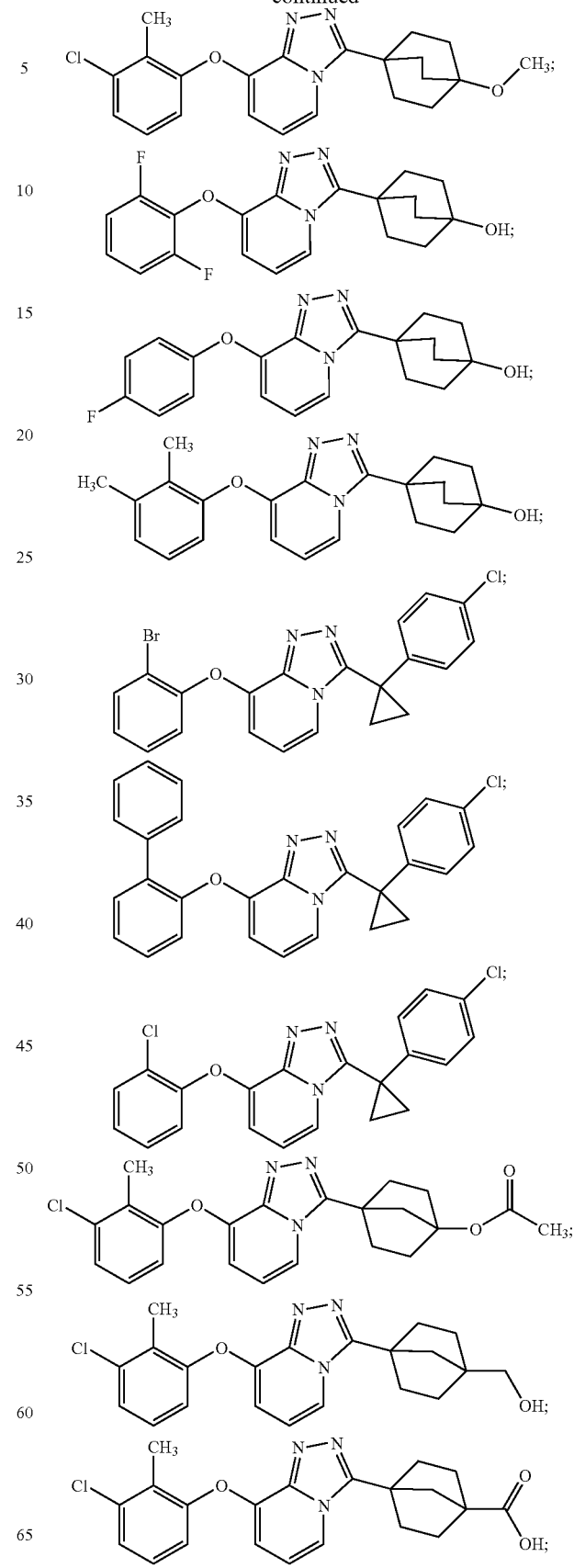

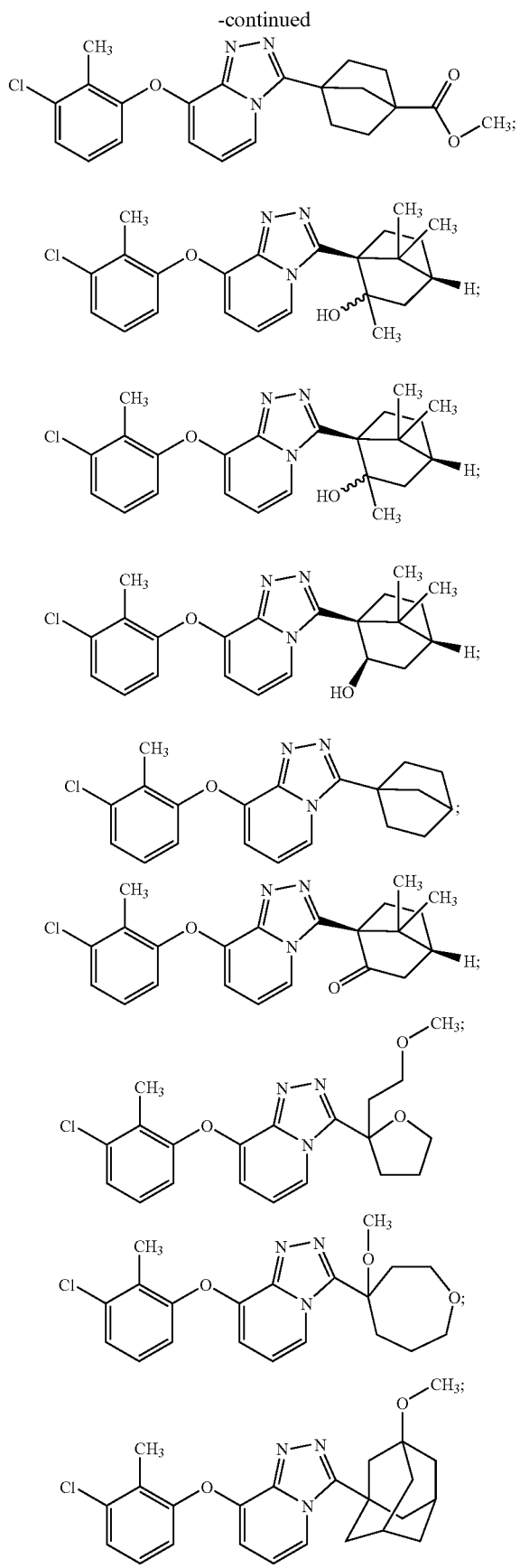
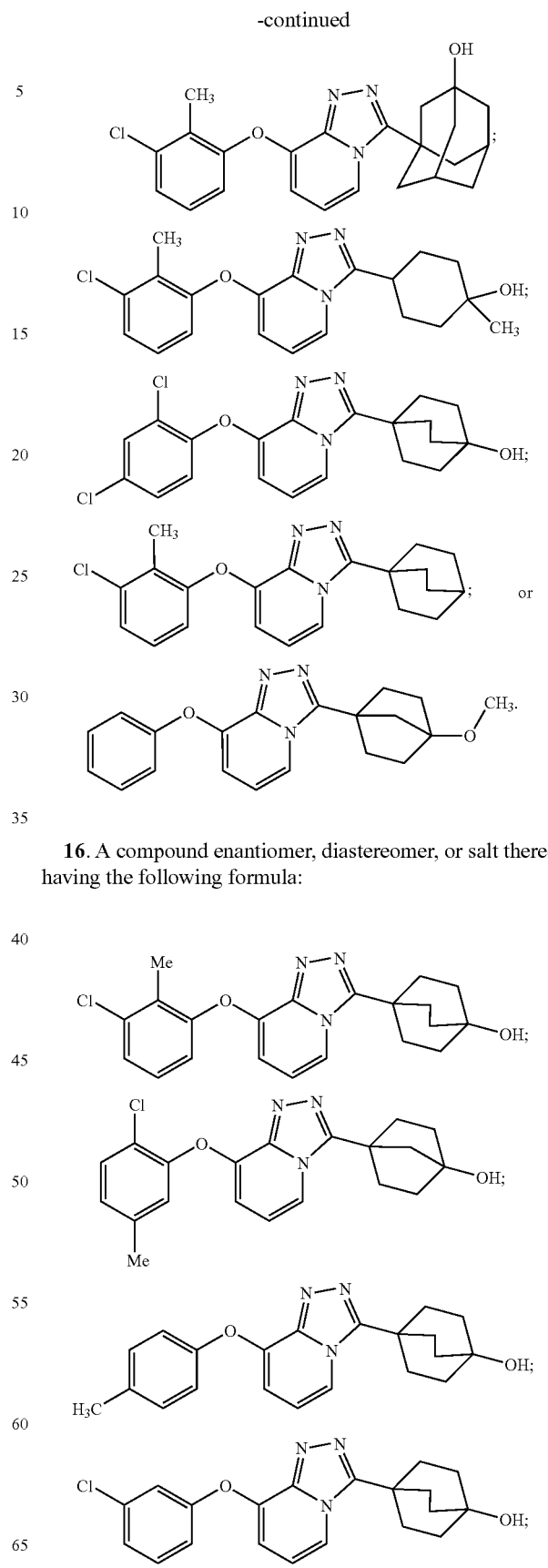
16. A compound enantiomer, diastereomer, or salt thereof having the following formula:

-continued

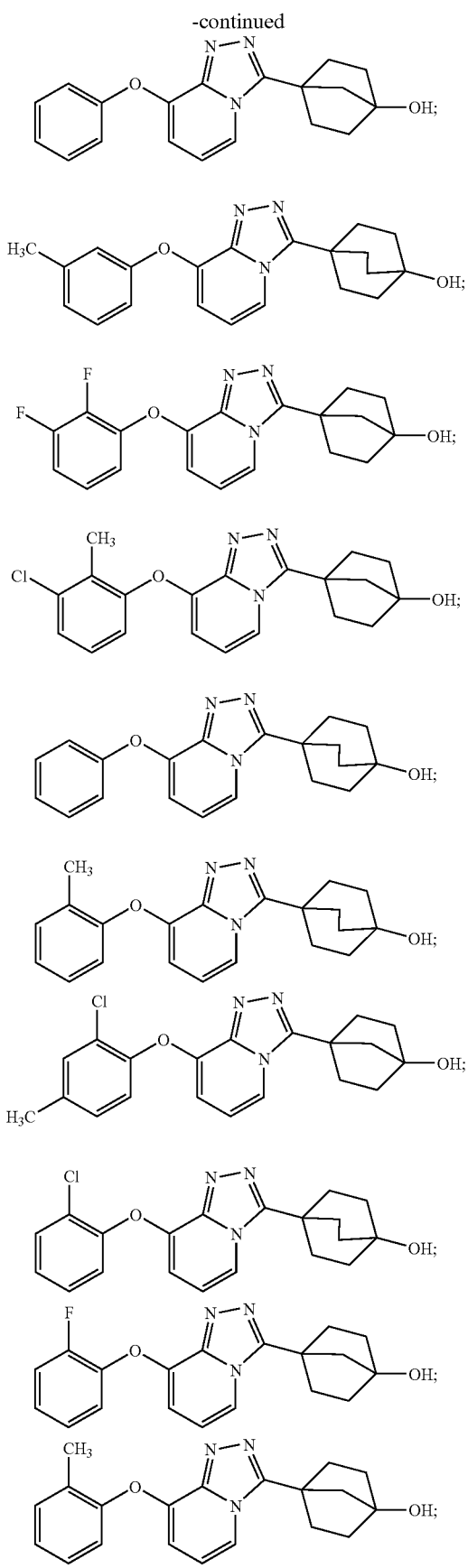

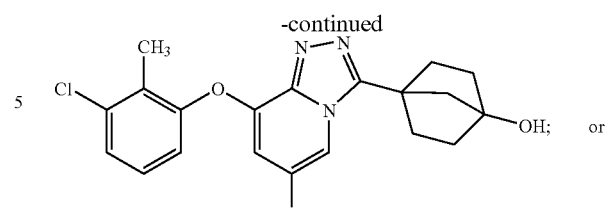

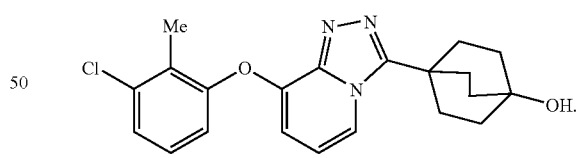

17. A pharmaceutical composition comprising a compound of claim 1.

18. The pharmaceutical composition of claim 17 further comprising a pharmaceutically acceptable carrier.

19. The pharmaceutical composition of claim 17 further comprising at least one additional therapeutic agent.

20. The pharmaceutical composition of claim 17, wherein the compound of Formula (I) is present in a therapeutically effective amount.

21. A method for inhibiting 11-beta-hydroxysteroid dehydrogenase in a patient has diabetes, hyperglycemia, obesity, dyslipidemia, hypertension, cognitive impairment, rheumatoid arthritis, osteoarthritis, glaucoma and Metabolic Syndrome, which comprises administering to a mammalian patient in need of treatment a therapeutically effective amount of a compound of claim 1.

22. The method according to claim 21 further comprising administering, concurrently or sequentially, a therapeutically effective amount of at least one additional therapeutic agent selected from the group consisting of other compounds of formula I, an anti-diabetic agent, an anti-hyperglycemic agent, anti-obesity agents, an anti-dislipidemic agent, a cognition promoting agent and an anti-inflammatory agent.

23. A compound, enantiomer, diastereomer or salt thereof, having the following formula:

24. The compound of claim 16 having the following formula:

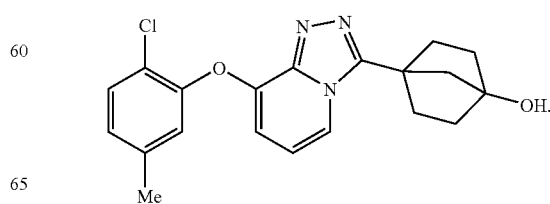

25. A compound, enantiomer, diastereomer or salt thereof, having the following formula:

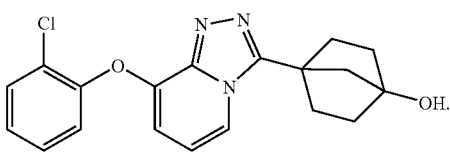

26. The compound of claim 16 having the following formula:

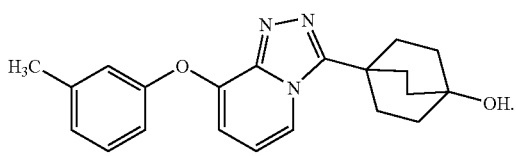

27. A compound, enantiomer, diastereomer or salt thereof, having the following formula:

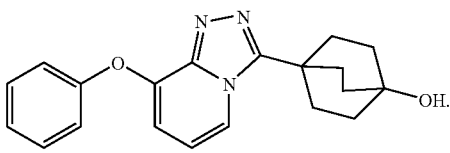

28. A pharmaceutical composition comprising a compound of claim 16.

29. The pharmaceutical composition of claim 28 further comprising a pharmaceutically acceptable carrier.

30. The pharmaceutical composition of claim 28 further comprising at least one additional therapeutic agent.

31. A method for inhibiting 11-beta-hydroxysteroid dehydrogenase in a patient has diabetes, hyperglycemia, obesity, dyslipidemia, hypertension, cognitive impairment, rheumatoid arthritis, osteoarthritis, glaucoma and Metabolic Syndrome, which comprises administering to a mammalian patient in need of treatment a therapeutically effective amount of a compound of claim 16.

32. A pharmaceutical composition comprising a compound of claim 25.

33. The pharmaceutical composition of claim 32 further comprising a pharmaceutically acceptable carrier.

34. The pharmaceutical composition of claim 32 further comprising at least one additional therapeutic agent.

35. A method for inhibiting 11-beta-hydroxysteroid dehydrogenase in a patient has diabetes, hyperglycemia, obesity, dyslipidemia, hypertension, cognitive impairment, rheumatoid arthritis, osteoarthritis, glaucoma and Metabolic Syndrome, which comprises administering to a mammalian patient in need of treatment a therapeutically effective amount of a compound of claim 25.

36. A pharmaceutical composition comprising a compound of claim 27.

37. The pharmaceutical composition of claim 36 further comprising a pharmaceutically acceptable carrier.

38. The pharmaceutical composition of claim 36 further comprising at least one additional therapeutic agent.

39. A method for inhibiting 11-beta-hydroxysteroid dehydrogenase in a patient has diabetes, hyperglycemia, obesity, dyslipidemia, hypertension, cognitive impairment, rheumatoid arthritis, osteoarthritis, glaucoma and Metabolic Syndrome, which comprises administering to a mammalian patient in need of treatment a therapeutically effective amount of a compound of claim 27.

40. A compound, enantiomer, diastereomer or salt thereof, having the following formula:

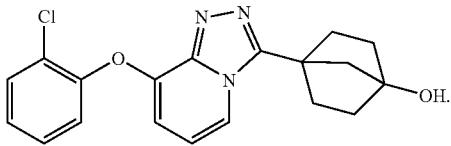

41. A pharmaceutical composition comprising a compound of claim 40.

42. The pharmaceutical composition of claim 41 further comprising a pharmaceutically acceptable carrier.

43. The pharmaceutical composition of claim 40 further comprising at least one additional therapeutic agent.

44. A method for treating or slowing the progression of diabetes, hyperglycemia, obesity, dislipidemia, hypertension, cognitive impairment, rheumatoid arthritis, osteoarthritis, glaucoma and Metabolic Syndrome, which comprises administering to a mammalian patient in need of treatment a therapeutically effective amount of a compound of claim 40.

45. A compound, enantiomer, diastereomer or salt thereof, having the following formula:

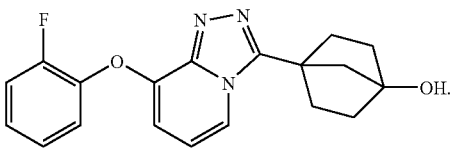

46. A pharmaceutical composition comprising a compound of claim 45.

47. The pharmaceutical composition of claim 46 further comprising a pharmaceutically acceptable carrier.

48. The pharmaceutical composition of claim 46 further comprising at least one additional therapeutic agent.

49. A method for treating or slowing the progression of diabetes, hyperglycemia, obesity, dislipidemia, hypertension, cognitive impairment, rheumatoid arthritis, osteoarthritis, glaucoma and Metabolic Syndrome, which comprises administering to a mammalian patient in need of treatment a therapeutically effective amount of a compound of claim 45.

* * * * *

UNITED STATES PATENT AND TRADEMARK OFFICE
CERTIFICATE OF CORRECTION

PATENT NO.      : 7,579,360 B2                           Page 1 of 4
APPLICATION NO. : 11/448947
DATED           : August 25, 2009
INVENTOR(S)     : Li et al.

It is certified that error appears in the above-identified patent and that said Letters Patent is hereby corrected as shown below:

Column 1
Line 4, Please insert the following heading under the title of the invention:
-- CROSS-REFERENCE TO RELATED APPLICATION --.

Column 93
Line 59, "$R_{1c}$," should read -- $R_{1c}$ --.

Column 96
Line 35, "—$CONR_2R_2$" should read -- —$CONR_2R_{2a}$, --.

Column 97
Line 13, "aryl" should read -- aryl, --; and
Line 27, "—$CONR_2R_2$" should read -- —$CONR_2R_{2a}$, --.

Column 98
Line 5, "aryl" should read -- aryl, --.

Column 99
Line 41, "$R_{1c}$," should read -- $R_{1c}$ --.

Column 104

Line 66, after " 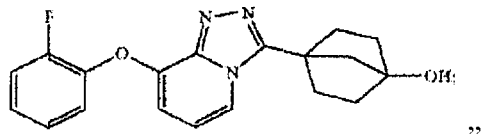  "

insert

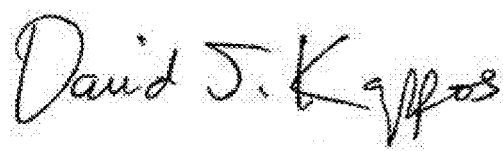

Signed and Sealed this
Eighteenth Day of January, 2011

David J. Kappos
*Director of the United States Patent and Trademark Office*

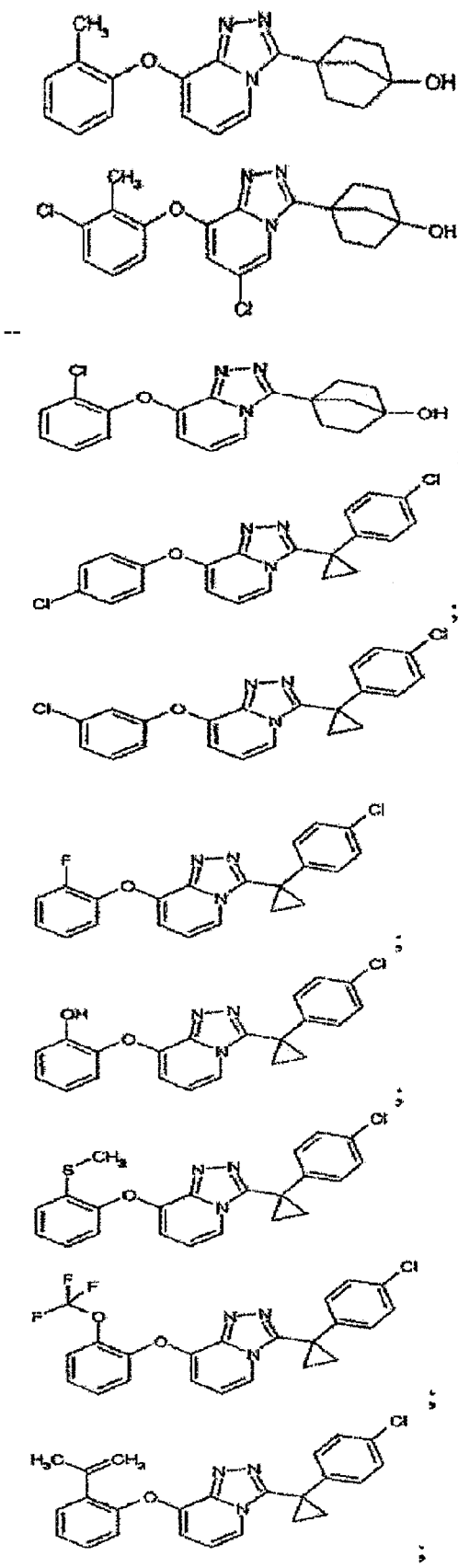

CERTIFICATE OF CORRECTION (continued)

U.S. Pat. No. 7,579,360 B2

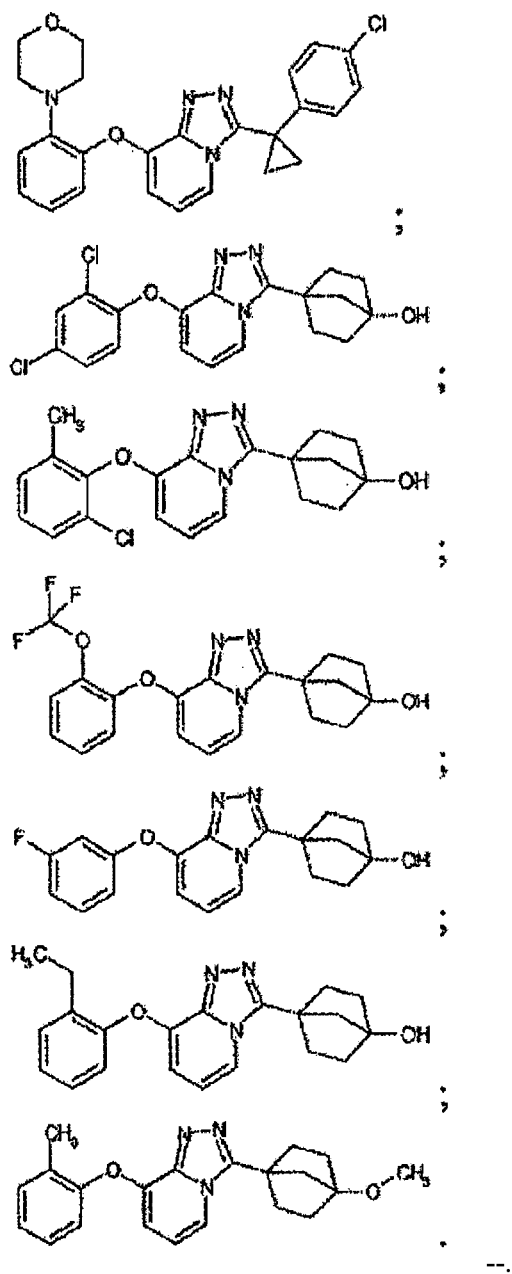

Column 112
Line 41, "anti-dislipidemic" should read -- anti-dyslipidemic --.

CERTIFICATE OF CORRECTION (continued)
U.S. Pat. No. 7,579,360 B2

Column 114

Lines 17-24, delete " 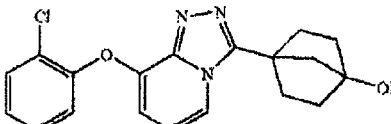 " and insert

-- 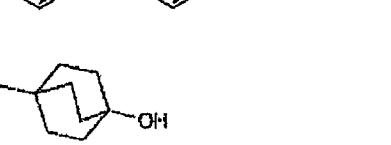 --.

Line 32, "dislipdemia," should read -- dyslipidemia, --; and
Line 55, "dislipdemia," should read -- dyslipidemia, --.